US010867706B2

(12) United States Patent
Hillis et al.

(10) Patent No.: US 10,867,706 B2
(45) Date of Patent: *Dec. 15, 2020

(54) MULTI-SCALE COMPLEX SYSTEMS TRANSDISCIPLINARY ANALYSIS OF RESPONSE TO THERAPY

(71) Applicants: Applied Invention, LLC, Glendale, CA (US); University of Southern California, Los Angeles, CA (US)

(72) Inventors: William Daniel Hillis, Encino, CA (US); David B. Agus, Beverly Hills, CA (US)

(73) Assignees: APPLIED INVENTION, LLC, Glendale, CA (US); UNIVERSITY OF SOUTHERN CALIFORNIA, Los Angeles, CA (US)

(*) Notice: Subject to any disclaimer, the term of this patent is extended or adjusted under 35 U.S.C. 154(b) by 937 days.

This patent is subject to a terminal disclaimer.

(21) Appl. No.: 14/826,049

(22) Filed: Aug. 13, 2015

(65) Prior Publication Data

US 2016/0103971 A1 Apr. 14, 2016

Related U.S. Application Data

(62) Division of application No. 13/187,115, filed on Jul. 20, 2011, now Pat. No. 9,141,756.

(60) Provisional application No. 61/366,028, filed on Jul. 20, 2010.

(51) Int. Cl.
*G16H 50/50* (2018.01)
*G16B 5/00* (2019.01)
*G16B 99/00* (2019.01)
*G16B 20/00* (2019.01)
*G16H 70/60* (2018.01)

(52) U.S. Cl.
CPC .............. *G16H 50/50* (2018.01); *G16B 5/00* (2019.02); *G16B 20/00* (2019.02); *G16B 99/00* (2019.02)

(58) Field of Classification Search
CPC .......... G16H 50/50; G06F 19/30; G16B 5/00; G16B 99/00; G16B 20/00
See application file for complete search history.

(56) References Cited

U.S. PATENT DOCUMENTS

| | | | |
|---|---|---|---|
| 5,674,753 A | 10/1997 | Harvey et al. | |
| 5,736,343 A | 4/1998 | Landry | |
| 5,786,158 A | 7/1998 | Artavanis-Tsakonas et al. | |
| 5,800,347 A | 9/1998 | Skates et al. | |
| 5,983,211 A | 11/1999 | Heseltine et al. | |
| 6,224,865 B1 | 5/2001 | Brünner et al. | |
| 6,316,208 B1 | 11/2001 | Roberts et al. | |
| 6,589,745 B2 | 7/2003 | Kaufmann | |
| 7,153,700 B1 | 12/2006 | Pardee et al. | |
| 7,526,387 B2 | 4/2009 | Baker et al. | |
| 7,807,379 B2 | 10/2010 | Holten-Andersen et al. | |
| 7,939,261 B2 | 5/2011 | Baker et al. | |
| 8,114,604 B2 | 2/2012 | Robertson et al. | |
| 9,141,756 B1 | 9/2015 | Hillis et al. | |
| 2003/0096755 A1 | 5/2003 | Brunner et al. | |
| 2003/0186248 A1 | 10/2003 | Erlander et al. | |
| 2006/0040306 A1 | 2/2006 | Leiby et al. | |
| 2008/0161420 A1 | 7/2008 | Shuber | |
| 2008/0255764 A1 | 10/2008 | Ritchie et al. | |
| 2008/0286801 A1 | 11/2008 | Arjol et al. | |
| 2009/0035801 A1 | 2/2009 | Goldknopf et al. | |
| 2009/0142332 A1 | 6/2009 | Ried et al. | |
| 2009/0150315 A1 | 6/2009 | Wirtz et al. | |
| 2009/0155842 A1 | 6/2009 | Baak et al. | |
| 2010/0055724 A1 | 3/2010 | Taylor et al. | |
| 2010/0261221 A1 | 10/2010 | Lee | |
| 2010/0304410 A1 | 12/2010 | Kijanka et al. | |
| 2011/0014204 A1 | 1/2011 | Feinberg et al. | |
| 2011/0104256 A1 | 5/2011 | Wang et al. | |
| 2011/0182879 A1 | 7/2011 | Meyers et al. | |
| 2011/0236916 A1 | 9/2011 | Zou et al. | |
| 2011/0294134 A1 | 12/2011 | Livneh et al. | |
| 2011/0294148 A1 | 12/2011 | Holten-Andersen et al. | |
| 2011/0315552 A1 | 12/2011 | Stults et al. | |
| 2013/0165340 A1 | 6/2013 | Watanabe et al. | |
| 2014/0170242 A1 | 6/2014 | Wagner et al. | |
| 2017/0285033 A1 | 10/2017 | Blume | |
| 2017/0370937 A1 | 12/2017 | Blume | |

FOREIGN PATENT DOCUMENTS

| | | |
|---|---|---|
| CN | 101971033 A | 2/2011 |
| CN | 103140760 A | 6/2013 |
| EP | 0712312 B1 | 4/2004 |
| EP | 1171771 B1 | 6/2005 |
| EP | 1078264 B1 | 12/2005 |
| EP | 0892809 B1 | 5/2006 |
| EP | 1499896 B1 | 8/2006 |
| EP | 1931995 A2 | 6/2008 |
| EP | 1335981 B1 | 6/2010 |
| EP | 2195658 A2 | 6/2010 |
| EP | 2111550 B1 | 11/2011 |
| EP | 2171465 B1 | 12/2011 |
| EP | 1430145 B1 | 1/2013 |

(Continued)

OTHER PUBLICATIONS

Anderson et al. (Nature Reviews (2008) vol. 8, pp. 227-234).

(Continued)

*Primary Examiner* — Lori A. Clow
(74) *Attorney, Agent, or Firm* — Wilson Sonsini Goodrich & Rosati

(57) ABSTRACT

Described herein are methods and systems to measure dynamics of disease progression, including cancer growth and response, at multiple scales by multiple techniques on the same biologic system. Methods and systems according to the invention permit personalized virtual disease models. Moreover, the invention allows for the integration of previously unconnected data points into an in silico disease model, providing for the prediction of disease progression with and without therapeutic intervention.

10 Claims, 37 Drawing Sheets

Specification includes a Sequence Listing.

(56) References Cited

FOREIGN PATENT DOCUMENTS

| | | |
|---|---|---|
| WO | WO-9502413 A1 | 1/1995 |
| WO | WO-9958978 A2 | 11/1999 |
| WO | WO-0206330 A2 | 1/2002 |
| WO | WO-02076280 A2 | 10/2002 |
| WO | WO-02077233 A2 | 10/2002 |
| WO | WO-03083141 A1 | 10/2003 |
| WO | WO-03097872 A2 | 11/2003 |
| WO | WO-2005008213 A2 | 1/2005 |
| WO | WO-2006047787 A2 | 5/2006 |
| WO | WO-2006102526 A2 | 9/2006 |
| WO | WO-2007016367 A2 | 2/2007 |
| WO | WO-2007030928 A2 | 3/2007 |
| WO | WO-2007060420 A1 | 5/2007 |
| WO | WO-2007130629 A1 | 11/2007 |
| WO | WO-2007144606 A2 | 12/2007 |
| WO | WO-2008073858 A2 | 6/2008 |
| WO | WO-2008116178 A2 | 9/2008 |
| WO | WO-2009015299 A1 | 1/2009 |
| WO | WO-2009025920 A2 | 2/2009 |
| WO | WO-2009040782 A2 | 4/2009 |
| WO | WO-2009040785 A1 | 4/2009 |
| WO | WO-2009099651 A1 | 8/2009 |
| WO | WO-2009138392 A1 | 11/2009 |
| WO | WO-2010009368 A2 | 1/2010 |
| WO | WO-2011119934 A2 | 9/2011 |
| WO | WO-2012013931 A1 | 2/2012 |
| WO | WO-2013162368 A1 | 10/2013 |
| WO | WO-2015149030 A1 | 10/2015 |

OTHER PUBLICATIONS

AU Application No. 11201504241Q Search Report and Written Opinion dated Apr. 25, 2016.
Bearer, et al. Multiparameter computational modeling of tumor invasion. Cancer Res. May 15, 2009;69(10):4493-501. Epub Apr. 14, 2009.
Bellomo et al. (Physics of Life Reviews (2008) vol. 5, pp. 183-206).
Butcher et al. (Nature Biotechnology (2004) vol. 22, pp. 1253-1259).
Cristini, et al. Morphologic instability and cancer invasion. Clin Cancer Res. Oct. 1, 2005;11(19 Pt 1):6772-9.
Cristini, et al. Nonlinear simulation of tumor growth. J Math Biol. Mar. 2003;46(3):191-224. Epub Dec. 18, 2002.
Deisboeck et al. (Nature Clinical Practice Oncology (2009) vol. 6, pp. 34-42).
Frieboes, et al. An integrated computational/experimental model of tumor invasion. Cancer Res. Feb. 1, 2006;66(3):1597-604.
Frieboes, et al. Computer simulation of glioma growth and morphology. Neuroimage. 2007; 37(Suppl 1):s59-s70.
Frieboes, et al. Three-dimensional multispecies nonlinear tumor growth-II: Tumor invasion and angiogenesis. J Theor Biol. Jun. 21, 2010;264(4):1254-78. Epub Mar. 18, 2010.
Henry L. R. et al., Clinical implications of fibroblast activation protein in patients with colon cancer. Clinical Cancer Research, 13(6); 1736-1741 (Mar. 18, 2007).
Kirana C. et al., Cathepsin D expression in colorectal cancer: from proteomic discovery through validation using western blotting, immunohistochemistry, and tissue microarrays. International Journal of Proteomics, 2012(245819); 1-10: (Jun. 24, 2012).
Levi Z., et al. A higher detection rate for colorectal cancer and advanced adenomatous polyp for screening with immunochemical fecal occult blood test than guaiac fecal occult blood test, despite lower compliance rate. A prospective, controlled, feasibility study. Int J Cancer. May 15, 2011 ;128(10):2415-24.
Macklin, et al. Agent-based modeling of ductal carcinoma in situ: application to patient-specific breast cancer modeling. Applied Bioinformatics and Biostatistics in Cancer Research, 2010, 77-111.
Macklin, et al. Nonlinear simulation of the effect of microenvironment on tumor growth. J Theor Biol. Apr. 21, 2007;245(4):677-704. Epub Dec. 12, 2006.
Martins et al. (Current Opinion in Colloid and Interface Science (2010) vol. 15, pp. 18-23).
Notice of allowance dated May 8, 2015 for U.S. Appl. No. 13/187,115.
Office action dated Jan. 2, 2014 for U.S. Appl. No. 13/187,115.
Office action dated Jun. 12, 2014 for U.S. Appl. No. 13/187,115.
Office action dated Aug. 15, 2014 for U.S. Appl. No. 13/187,115.
Office action dated Sep. 4, 2013 for U.S. Appl. No. 13/187,115.
Quaranta et al. (Seminars in Cancer Biology (2008) vol. 18, pp. 338-348.
Rubinow, et al. A mathematical model of the chemotherapeutic treatment of acute myeloblastic leukemia. Biophys J. Nov. 1976;16(11):1257-71.
Siegmund, et al. Many colorectal cancers are "flat" clonal expansions. Cell Cycle. Jul. 15, 2009;8(14):2187-93. Epub Jul. 1, 2009.
Slovac, et al. Karyotypic analysis predicts outcome of preremission and postremission therapy in adult acute myeloid leukemia: a Southwest Oncology Group/Eastern Cooperative Oncology Group Study. Blood. Dec. 15, 2000;96(13):4075-83.
U.S. Appl. No. 14/526,282 Advisory Office Action dated May 12, 2016.
Wise, et al. Three-dimensional multispecies nonlinear tumor growth—I model and numerical method. J Theor Biol. Aug. 7, 2008;253(3):524-43. Epub Mar. 28, 2008.
Database Medline [Online] US National Library of Medicine (NLM), Bethesda, MD, US; Aug. 1990 (Aug. 1990), Yuan M: "[Value of fecal detection of cancer-associated antigens using monoclonal antibodies in the diagnosis of colorectal cancel].", XP002690733, Database accession No. NLM2086118 & Zhonghua Wai Ke Za Zhi [Chinese Journal of Surgery] Aug. 1990, vol. 28, No. 8, Aug. 1990 (Aug. 1990), pp. 497-500 , 511, ISSN: 0529-5815.
Deug-Chan Lee et al. Protein Profiling underscores immunological functions of uterine cervical mucus plug in human pregnancy, Journal of Proteomics, 74(6); 817-828 (2011).
Di Marzio, L. Detection of Alkaline Sphingomyelinase Activity in Human Stool; Proposed Role as a New Diagnostic and Prognostic Marker of Colorectal Cancer. Cancer Epidemiology, Biomarkers & Prevention, 14(4); 856-862 (2005).
European Application No. 13 858410.7 Extended European Search Report dated Aug. 11, 2016.
He, Z. et al. The Potential of carcinoembryonic antigen, p53, Ki-67 and glutathion Stransferase-π as clinico-histopathological markers for colorectal cancer. Journal of Biomedical Research 2010 24(1):51-57.
International Application No. PCT/US2015/023187 International Preliminary Report on Patentability dated Oct. 4, 2016.
International Application No. PCT/US2016/026773 International Search Report and Written Opinion dated Jul. 19, 2016.
Kopetz, Scott et al. Phase II Trial of Infusional Fluorouracil, Irinotecan, and Bevacizumab for Metastatic Colorectal Cancer: Efficacy and Circulating Angiogenic Biomarkers Associated with Therapeutic Resistance. Journal of Clinical Oncology 28(3); 453-459 (Jan. 20, 2010).
Thorsen, Stine Buch et al. Detection of serological biomarkers by proximity extension assay for detection of colorectal neoplasias in symptomatic individuals. Journal of Translanational Medicine 11(253): 1-13 (2013).
U.S. Appl. No. 14/526,265 Office Action dated Aug. 16, 2016.
U.S. Appl. No. 15/094,767 Office Action dated Sep. 27, 2016.
U.S. Appl. No. 15/094,767 Restriction Requirement dated Aug. 15, 2016.
Volmer, Martin W. et al. Differential proteome analysis of conditioned media to detect Smad4 regulated secreted biomarkers in colon cancer, Proteomics, 5(10); 2587-2601 (2005).
Xiaoyang, L. et al. A High-quality secretome of A549 cells aided the discovery of C4b-binding protein as a novel serum biomarker for non-small cell lung cancer. Journal of Proteomics, 74(4);528-538 (2011).
Zimmermann-Nielsen, E. et al. Complement activation mediated by mannan-binding lectin in plasma from healthy individuals and from patients with SLE, Crohn's disease and colorectal cancer. Suppressed activation by SLE plasma. Scandinavian Journal of Immunology, 55;105-110 (2002).

(56) References Cited

OTHER PUBLICATIONS

Abbatiello, S.E. et al. Automated Detection of Iaccurate and Imprecise Transitions in peptide Quantification by Multiple Reaction Monitoring Mass Spectrometry, Clinical Chemistry 56(2):291-305 Dec. 18, 2009.

Abu-Rabie, Paul et al. Method of Applying Internal Standard to Dried Matrix Spot Samples for Use in Quantitative Bioanalysis. Analytical Chemistry, 83(22):8779-8786 (Nov. 15, 2011) [Abstract Only].

Bringans, S.D. et al. Comprehensive mass spectrometry based biomarker discovery and validation platform as applied to diabetic kidney disease. EuPA Open Proteomics, 14:1-10 (Jan. 1, 2017).

Chambers, M.C. et al. A cross-platform toolkit for mass spectrometry and proteomics, Nature Biotechnology 30(10):918-920 (Oct. 10, 2012).

Chen, et al. Identification of biomarkers to improve diagnostic sensitivity of sporadic colorectal cancer in patients with low preoperative serum carcinoembryonic antigen by clinical proteomic analysis. Clinica Chimica Acta 412: 636-641 (2011).

Chinese Application No. 201580028098.4 Office Action dated Nov. 27, 2018.

Cordero, OJ et al. Preoperative serum CD26 levels: diagnostic efficiency and predictive value for colorectal cancer. British Journal of Cancer 83(9); 1139-1146 (2000).

Coutsoftides, T. et al. Colonoscopy and the Management of Polyps Containing Invasive Carcinoma. Ann. Surg. 188(5):638-641 (1978).

Denkert et al. Metabolite profiling of human colon carcinoma-deregulation of TCA cycle and amino acid turnover, Molecular Cancer 7(72); 1-15 (2008).

Etzioni, et al. The Case for Early Detection. Nature Reviews—Cancer, 3:1-10 (Apr. 2003).

European Application No. 13858410.7 Office Action dated Nov. 21, 2018.

European Application No. 16717530.6 Office Action dated Dec. 20, 2018.

Ferroni, P. et al. Prognostic Value of Soluble P-Selectin Levels in Colorectal Cancer, Int. J. Cancer, 111:404-408 (2004).

Gaissmaier, Tanja et al. Therapeutic drug monitoring in dried blood spots using liquid microjunction surface sampling and high resolution mass spectrometry. Analyst, 141(3):892-901 (Jan. 1, 2016).

Hill, J. E. et al. Measurement of Diabetes-Predictive Amino Acids from Dried Blood. URL:http://www/spotonsciences.com/wp-content/uploads/Spot-On-Sciences-poster-MSACL.pdf p. 1, Jan. 1, 2012 [Retrieved from the internet Sep. 6, 2017]. 1 page.

International Application No. PCT/US2016/026773 International Preliminary Report on Patentability dated Oct. 19, 2017.

International Application No. PCT/US2017/025580 International Search Report and Written Opinion dated Aug. 23, 2017.

International Application No. PCT/US2017/055659 International Search Report and Written Opinion dated Jan. 18, 2018.

Lee, H. et al. Macrophage Migration Inhibitory Factor May Be Used as an Early Diagnostic Marker in Colorectal Carcinomas. Anm. J. Clin. Pathol. 129-772-779 (2008).

MacLean, B. et al. Skyline: an open source document editor for creating and analyzing targeted proteomics experiments, Bioinformatics 26(7):966-968 (Feb. 9, 2010).

Meng, W. et al. Serum M2-pyruvate kinase: A promising non-invasive biomarker for colorectal cancer mass screening. World J. Gastrointest. Oncol. 4(6):145-151 (Jun. 15, 2012).

Mercer, D.W. Use of Multiple Markers to Enhance Clinical Utility, Immunor Ser. 53:39-54 (1990).

Minicozzi, P. et al. Disease presentation, treatment and survival for Italian colorectal cancer patients: a EUROCARE high resolution study. European Journal of Public Health, vol. 24, No. 1, pp. 98-100 (2014) (E-Pub. May 31, 2013).

Pinczower, G.D., et al. Characterisation of the Tumour-Associated Carbohydrate Epitope Recognised by Monoclonal Antibody 4D3, Int. J. Cancer: 66: 636-644 (1996).

Pinczower, G.D. et al. Monoclonal Antibody 4D3 Detects Small Intestinal Mucin Antigen (SIMA)—Glycoprotein in the Serum of Patients with Colorectal Cancer, Int. J. Cancer: 54; 391-396 (1993).

SG Application No. 11201504241Q Search Report and Written Opinion dated Apr. 25, 2016.

Chinese Application No. 201380071930X Office Action dated Nov. 30, 2018.

Talieri, Maroulio et al. Cathepsin B and cathepsin D expression in the progression of colorectal adenoma to carcinoma, Cancer Letters 205;97-106 (2004).

Teleman, J. et al. Automated Selected Reaction Monitoring Software for Accurate Label-Free Protein Quantification, Journal of Proteome Research, 11(7):3766-3773 (Jul. 6, 2012.

U.S. Appl. No. 14/526,181 Office Action dated Dec. 12, 2016.

U.S. Appl. No. 14/526,221 Advisory Office Action dated Mar. 6, 2017.

U.S. Appl. No. 14/526,221 Final Office Action dated Dec. 15, 2016.

U.S. Appl. No. 14/526,282 Final Office Action dated Dec. 2, 2016.

U.S. Appl. No. 15/414,456 Final Office Action dated Dec. 21, 2017.

U.S. Appl. No. 15/414,456 Non-Final Office Action dated Jul. 6, 2018.

U.S. Appl. No. 15/414,456 Non-Final Office Action dated May 26, 2017.

U.S. Appl. No. 15/629,593 Final Office Action dated Apr. 10, 2018.

U.S. Appl. No. 15/629,593 Non-Final Office Action dated Oct. 16, 2017.

Vokes, E.E. et al. Concomitant Chemoradiotherapy: Rationale and Clinical Experience in Patients with Solid Tumors. Journal of Clinical Oncology, 8(5): 911-934 (May 1990).

Young, et al Fecal Tests: From Blood to Molecular Markers, Curr Colorectal Cancer Rep, 7;62-70 (2011).

Zakaria, R. et al. Advantages and challenges of dried blood spot analysis by mass spectrometry across the total testing process. The electronic Journal of the International Federation of Clinical Chemistry and Laboratory Medicine, 27(4): 288-317 (Dec. 1, 2016).

Zhang, X. et al. Automated Method for the Analysis of Stable Isotope Labeling Data in Proteomics. Journal for the American Society for Mass Spectrometry, 16(7): 1181-1191 (Jul. 1, 2005).

FIG. 11A
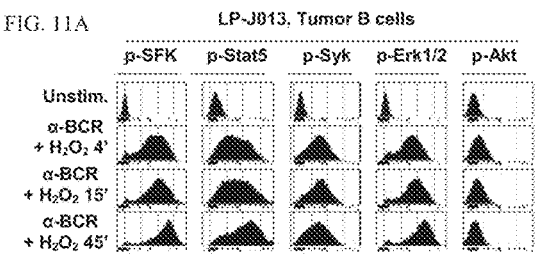
LP-J013, Tumor B cells
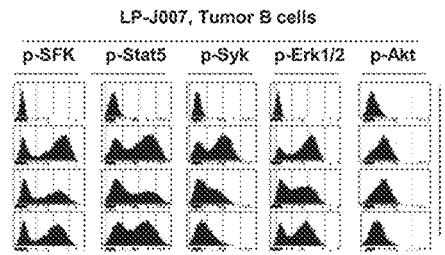
LP-J007, Tumor B cells
FIG. 11B
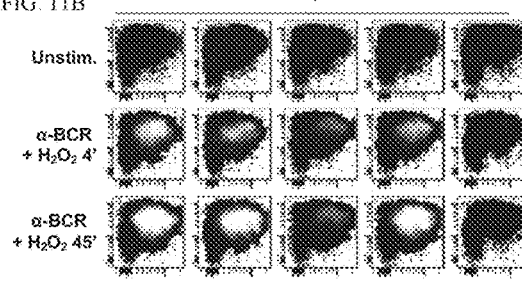
LP-J013, All Cells
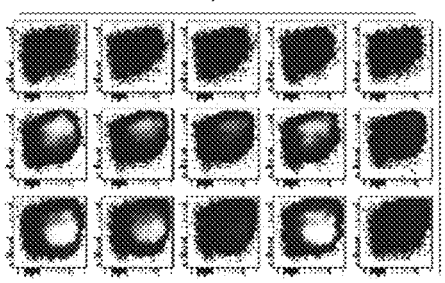
LP-J007, All Cells
FIG. 11C
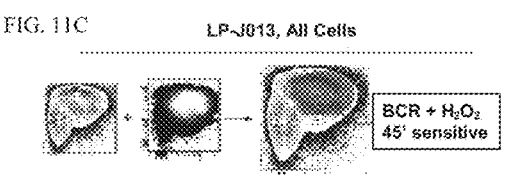
LP-J013, All Cells
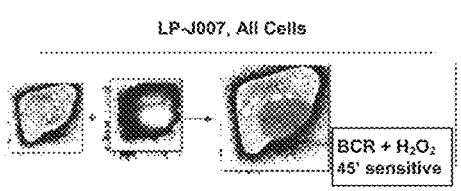
LP-J007, All Cells FIGURE 15
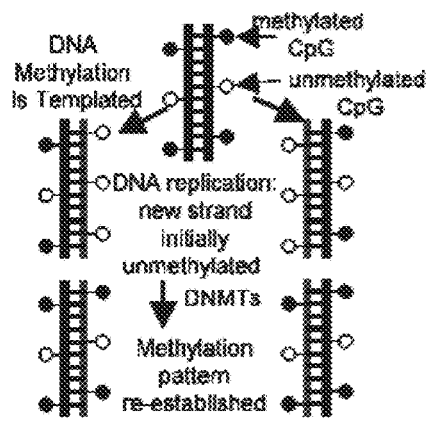
Methylation Patterns May Drift From Replication Errors
(clock hypothesis---the great the number of divisions since a common ancestor, the greater the difference between two epialleles (here a Hamming or pairwise distance))
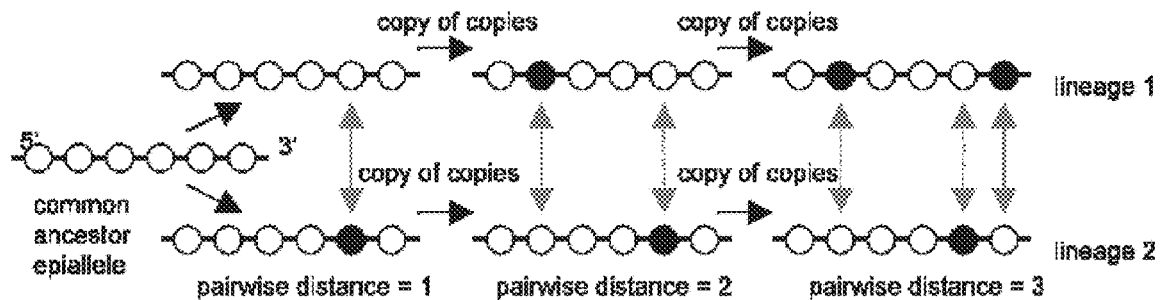

FIGURE 18

CSX (8 CpG sites, Chr 5q34)

ggagaTTtaggaacttttttTtgtTTTaCGCGCGtttgttTttgCGTaCGggagagtttgtggCGgCGattatgTagCGtgTa
atgagtgatTTtgTagTTtggtgtT <div align="right">SEQ ID NO: 1</div>

BGN (9 CpG sites, Chr Xq28)

TTTaggagtgagtagTtgTtttCGgtTCGTCGgaTaTaTCGgaTagatagaCGtgCGgaCGgTTTaTTaTTTTag
TTCGTTaaTtagtTagTTtgCGTTtggCGTTtTTTTtTtTTaggtagggTtggT <div align="right">SEQ ID NO: 2</div>

MULTI-SCALE COMPLEX SYSTEMS TRANSDISCIPLINARY ANALYSIS OF RESPONSE TO THERAPY

CROSS-REFERENCE TO RELATED APPLICATION

This application is a divisional application of U.S. patent application Ser. No. 13/187,115, filed on Jul. 20, 2011, which application claims the benefit of U.S. Provisional Patent Application No. 61/366,028, filed Jul. 20, 2010, each of which is incorporated herein by reference in its entirety.

STATEMENT AS TO FEDERALLY SPONSORED RESEARCH

This invention was made with the support of the United States government under Contract number CA143907 by the National Cancer Institute of the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Sep. 20, 2011, is named 40001701.txt and is 1,042 bytes in size.

FIELD OF THE INVENTION

Described herein are methods and systems to measure dynamics of disease progression such as cancer growth and response at multiple scales by multiple techniques on the same biologic system. Methods and systems according to the invention permit personalized virtual disease models, such as cancer models. Moreover, the invention allows for the integration of previously unconnected data points into an in silico disease model, providing for the prediction of progression of a disease such as cancer with and without therapeutic intervention.

BACKGROUND OF THE INVENTION

Clinical tools to accurately describe, evaluate and predict an individual's response to cancer therapy are a field-wide priority. For example, the adjuvant treatment of women with early stage breast cancer will subject a significantly larger number of women to chemotherapy than who can benefit from it, or in the case of advanced cancers only 10-20 percent of individuals will have a clinical benefit from therapy, yet we treat the entire population. Furthermore, many therapies are initially effective, but lose effectiveness over time. Under the current paradigm, diseases are first classified into one of a small number of groups and then an indicated treatment is attempted. These groups have poor resolution and frequently poor predictive power leaving oncologists with limited means to assess or predict a patient's response to a given therapy. Instead, patients must undergo therapy that is often not optimal for their disease only to have it fail so that yet another therapeutic regimen must be attempted.

An integrative, multi-scale approach is necessary to develop accurate, useable models to study complex diseases such as cancer. Combining diverse perspectives and techniques developed by physical and quantitative sciences with that of biological sciences can make a significant impact on cancer management and treatment in revolutionary ways. Subtle molecular-scale perturbations (e.g. mutation in a gene) can produce dramatic, tumor-scale (e.g. invasiveness) and organism scale (e.g. responsiveness to therapy) affects. To generate a model of cancer that can be used to predict the behavior of cancers during emergence and in response to perturbation, diverse physical measurements at multiple scales from molecular to organismic level need to be integrated with sophisticated and diverse modeling approaches. Multi-scale measurement and modeling would allow specific cases of cancer to be modeled with sufficient fidelity to estimate the relative probable efficacy of alternative therapies (e.g., by rationally integrating genotype, tumor environment and treatment parameters to predict outcome). When integrated in an appropriate modeling framework, analyses of specific properties at the molecular-cell, tumor and host levels can inform therapeutic response.

SUMMARY OF THE INVENTION

In one aspect, the invention is directed to a method of treating cancer in an individual. Such methods according to the invention may comprise obtaining at least one molecular-scale measurement, at least one organ-scale measurement, and at least one organism-scale measurement from said individual; correlating the measurements of the individual to measurements from individuals with known outcomes; and determining the relative probabilities of the individual's outcomes. The method can be applied to any cancer, including solid tumors, leukemias and lymphomas. In various embodiments, the number of data points or measurements to be obtained may be very large, for example, at least one thousand data points or measurements.

In various aspects, the invention is directed to predicting the outcomes of cancer treatment, in individuals diagnosed with cancer. Such predictions are useful in determining a preferred course of treatment or therapy. Accordingly, the methods of the invention predicting cancer progression in response to a virtual perturbation may be used to select specific cancer treatments in patients. In iterative embodiments, the invention allows for the incorporation of responses to real treatments to improve the cancer model and guide future rounds of prediction and treatment selection. The virtual perturbation may be analogous to a real perturbation applied to the individual. Such perturbations relate to a change applied to the individual. In various embodiments, the perturbation is selected from an endogenous or exogenous substance, such as a growth factor, oxygen, a nutrient, a drug or drug combination, a mutation, a cytokine, and combinations thereof. For example, the perturbation may be the virtual administration of a drug or drug combination, such as cyclophosphamide, vincristine, doxorubicin, prednisone, prednisolone, and combinations thereof. Alternatively, the perturbation may be the virtual administration of a potential therapy, for example, a therapy that has not yet shown efficacy or is still in pre-clinical or clinical trials. Alternatively, the perturbation may be an environmental or nutritional change.

In one embodiment, the method according to the invention is applied to an individual undergoing treatment for cancer. In such an embodiment, the method further includes administration of treatment or therapy to the individual, followed by repetition of the steps of the method, i.e. obtaining measurements from the individual, correlating the measurements to a collection of measurements, and determining the relative probabilities of the individual's potential outcomes. In various embodiments, the method of treating cancer in an individual comprises modeling the progression of cancer in the individual with a multi-scale complex system as described herein in the presence of at least one virtual treatment; selecting a treatment based on the modeling; and administering the treatment to the individual.

In one aspect, the invention is directed to a method of predicting cancer emergence or progression in an individual. Such methods according to the invention may comprise obtaining at least one molecular-scale measurement, at least one organ-scale measurement, and at least one organism-scale measurement from said individual; correlating the measurements of the individual to measurements from individuals with known outcomes; and determining the relative probabilities of the individual's outcomes. The method can be applied to any cancer, including solid tumors, leukemias and lymphomas. In various embodiments, the number of data points or measurements to be obtained may be very large, for example, at least one thousand data points or measurements.

In various aspects, the invention is directed to predicting cancer emergence, for example in individuals not diagnosed with cancer, or alternatively, the invention may predict cancer progression in individuals where cancer has already emerged. In those individuals already experiencing cancer, the methods of the invention may be used to predict cancer progression in response to a virtual perturbation. Such predictions are useful in determining a preferred course of treatment or therapy. The perturbation may be selected from a growth factor, oxygen, a nutrient, a drug or drug combination, a mutation, a cytokine, environmental conditions, nutritional status, and combinations thereof. For example, the perturbation may be the virtual administration of a drug or drug combination, such as cyclophosphamide, vincristine, doxorubicin, prednisone, prednisolone, and combinations thereof. Alternatively, the perturbation may be the virtual administration of a potential therapy, for example, a therapy that has not yet shown efficacy or is still in pre-clinical or clinical trials.

In addition to the methods described herein, the invention is directed to a multi-scale complex system for modeling cancer emergence or progression. The system according to the invention includes i) a first module modeling cellular behavior based on cellular or molecular-scale measurements; ii) a second module modeling tissue or organ behavior based on organ-scale measurements; iii) a third module modeling host behavior based on organism-scale measurements; and iv) a computer-readable logic applying a feedback loop receiving and forwarding data from and to the modules to refine the system. In various embodiments, the modules are stored on a computer-readable medium.

In certain embodiments, the system models cancer progression, and the cellular or molecular-scale measurements are taken from a tumor. The cancer progression may be modeled with one or more parameters for cell adhesion, tissue invasion, and/or microenvironmental substrate gradients.

In various embodiments, the system is used to test the efficacy of perturbations in one or more individuals. Multi-scale complex systems (MSCSs) described herein are useful as integrated virtual cancer models. The virtual cancer models can be specific to a particular tumor in a single subject or a group of tumors in one or more subjects with shared characteristics. In some embodiments, the shared characteristic is a molecular-scale characteristic. In some embodiments, the characteristic is a tissue- or organ-scale characteristic. In some embodiments, the characteristic is an organism-scale characteristic. In certain embodiments, the characteristic results from one or more measurements in real subjects. In certain embodiments, an output from a virtual cancer model is used to direct experimental or established therapies with tested perturbations.

In various embodiments, cellular or molecular-scale measurements can be selected from gene expression patterns, genetic mutation patterns, genetic methylation patterns and/or heterogeneity, apoptosis patterns, molecular phylogeny, cell history patterns, phosphorylation patterns, oxidation patterns, molecular signaling pathways, microenvironmental conditions, and combinations of these measurements. In addition, cellular or molecular-scale measurements may be epigenetic somatic cell clock data measured by tracing methylation pattern or copy number variation. Moreover, microenvironmental conditions may be selected from oxygen levels, nutrient levels, growth factor levels, and combinations thereof. In various embodiments, organ-scale measurements are selected from vasculature structure, three-dimensional physical parameters of an organ such as a lymph node, blood flow rate, ECM degradation rate, ECM secretion rate, tissue density, drug extravasation rate, spatial and/or statistical distribution of cells within a tumor, tumor size, response of a cancer to treatment, and combinations of these measurements. Organism-scale measurements can be selected from dietary history, individual medical history, family medical history, geographic history, body-mass index, environmental exposure history, educational history, economic history, behavioral history, and combinations of these measurements, or the like.

The system may be applicable to any complex disease such as cancer. In certain embodiments, the disease for which response to treatment is measured is selected from a solid and hematologic tumor. In certain embodiments, the disease is a leukemia or lymphoma, such AML, NHL, and primary follicular lymphoma.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11A, FIG. 11B, and FIG. 11C illustrate Flow cytometry analysis of BCR signaling in FL tumor cell subsets is shown for patients representing two contrasting signaling profiles (LP-J013 and LP-J007).

FIG. 15 illustrates DNA methylation and its drift from replication errors.

FIG. 18 illustrates an example of epigenetic somatic cell clock. FIG. 18 discloses SEQ ID NOS 1-2, respectively, in order of appearance.

DETAILED DESCRIPTION OF THE INVENTION

Described herein are methods and systems to measure dynamics of disease progression such as cancer growth and response at multiple scales by multiple techniques on the same biologic system. Methods and systems according to the invention permit personalized virtual disease models, such as cancer models. Moreover, the invention allows for the integration of previously unconnected data points into an in silico disease model, providing for the prediction of progression of a disease such as cancer with and without therapeutic intervention.

For complex diseases including cancer, integrated information from multiple analytic strategies would provide information of greater value than any one test alone. For example, by combining results of observed cellular mutations that predispose towards sensitivity towards hypoxia with observed tumor vascular structures, the level of successful anti-angiogenic therapies can be postulated for a specific cancer that is measured.

As described herein, measurements are performed while maintaining a dual focus on clinical relevance and experimental validations of measured variables to gauge potential of each measured variable and verify its weight on the power of prediction. A multi-scale complex system (MSCS) described herein comprises multiple subcomponents wherein each subcomponent comprises a modeling module. MSCSs described herein are useful as integrated virtual cancer models. In one embodiment, a module is a molecular-cellular model (RP1). In another embodiment, a module is a cancer cell evolutionary model of tumor heterogeneity (RP2). In another embodiment, a module is a whole tumor model with physically relevant spatial parameters to model tumor micro-environment and interaction with vasculature (RP3). In another embodiment, a module is a host model that resembling physiological, immune and metabolic responses to tumor growth in the host (RP4). These modules are built upon a unique set of synchronized data. Synchronization is achieved by standardizing protocols and utilizing a suite of common measurement platforms applied to a common set of samples.

Figure 1:
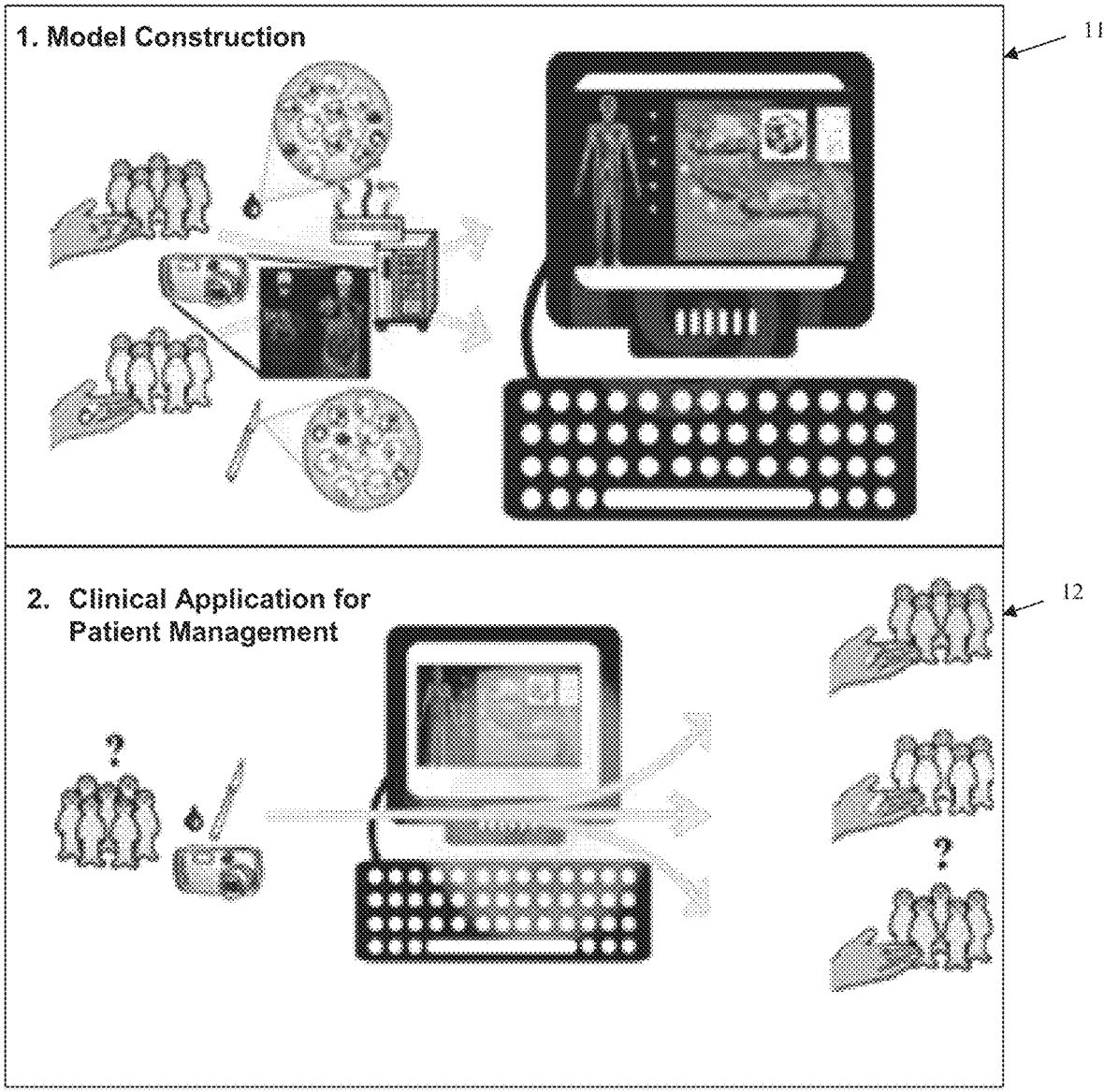
FIG. 1 illustrates the concept of a multi-scale complex system (MSCS).

Accurate methods for simulating cancer behavior can lead to dramatic improvements in cancer management as these simulations can be used to predict and characterize response and outcome. MSCSs described herein are virtual cancer models able to accurately predict the steady state growth and response to therapy of a cancer in a human host. FIG. 1 illustrates the concept of an MSCS. Shown in the upper panel (11) illustrates where sets of model subject (e.g., patients, animal, healthy volunteers) with known outcomes are analyzed by a variety of sophisticated techniques at multiple scales including imaging, biopsies of their tumor, and blood/plasma analysis by a variety of technologies. The outcome of the analysis is incorporated into an integrated multi-scale virtual cancer model of response to therapy. Once an initial model is constructed, it is used to simulate therapy courses for subjects (12). Samples from these subjects are used to calibrate the model so the simulation has a frame of reference with which to begin. Using the simulation, optimal courses of treatment is defined and also measurements are used to monitor treatment response.

MSCSs described herein are helpful for addressing fundamental questions about cancer mechanism, complexity and evolution, which will enable a paradigm in treatment. In MSCSs described herein, it is possible to take a small number of measurements from a subject, at a variety of scales ranging from genetic to organismic, input those measurements as calibrants to virtual cancer and then simulate the growth and response to therapy of the patient. MSCSs allow, for example, understanding of the disease, its progression and how it responds to therapy, and to choose a course of treatment that is most likely to lead to a favorable outcome. In addition, MSCSs allow trying out hundreds of therapeutics virtually before ever having to inflict treatments on a patient. Lastly, MSCSs allow identifying signals (e.g. changes in a tumor or serum protein) indicating if a subject is truly responding to therapy, which will lead to an improved standard of care.

Described herein are methods of building a virtual cancer model. In one embodiment, a virtual cancer model is an MSCS. In one embodiment, an MSCS is built by integrating techniques and tools available in various fields of sciences including, but are not limited to, mathematics, physics, chemical engineering, computer science, proteomic technology, chemistry/biochemistry, bioinformatics & metrology, and biology. In one embodiment, building an MSCS comprises obtaining input from multiple fields of sciences. In another embodiment, building an MSCS comprises collecting experimental, clinical or other health-related data and processing the data through quantitative, statistical, or other mathematical methods. In another embodiment, said processing is performed by computer-readable logic and the output is stored in a computer-readable medium.

In various embodiments, MSCSs described herein provide information on therapeutic response. In some embodiments, the information is a prediction that is associated with a probability of at least 20%, 30%, 40%, 50%, 60%, 70%, 80%, 90%, 95%, 98%, 99%, 99.5%, 99.9%, or higher. In some embodiments, the information is a prediction of low or non-responsiveness of host. In some embodiments, prediction of low or non-responsiveness comprises synthesizing predictive value with genetic background information.

In some embodiments, a method of building MSCS comprises utilizing known genetic information. In one embodiment, genetic information is mouse genetic information. In another embodiment, genetic information is clinical genetic information. In another embodiment, genetic information is utilized to elucidate how particular lesions affect disease progression and therapeutic response. In another embodiment, genetic information is utilized to produce a more personalized and effective approach towards treatment. In certain embodiments, specific cytogenetic abnormalities are associated with defined outcomes.

In various embodiments, MSCSs described herein provide models of disease such as cancer in heterogeneous organs. In some embodiments, models comprising heterogenous organs are capable of showing the impact of levels of endogenous variables and perturbations on cancer. In some embodiments, these models show the impact of endogenous variables and perturbations on response to therapy or cancerous cell motion in specific organ geometry. In some embodiments, the models show the impact of oxygen on response to therapy or cancerous cell motion in specific organ geometry. In some embodiments, the models show the impact of one or more drug gradients on response to therapy, or cancerous cell motion in specific organ geometry.

In certain embodiments, MSCSs described herein provide models of cancer capable of predicting whole-tumor evolution or understanding the spatiotemporal dynamics. In some embodiments, MSCSs described herein utilize spatial modeling which models extravasation, diffusion, and binding of monoclonal antibodies in tumors of various geometries. In some embodiments the tumors are spherically-symmetric.

Resources for Building a Multi-Scale Complex System (MSCS)

Building a virtual cancer model correctly predicting a response to a therapeutic intervention requires access to large amount of resources. In one embodiment, a method of building MSCS comprises having access to resources. In one embodiment, a resource is a hospital where clinical trial or clinical data collection can be performed. Such hospital can be a hospital equipped with cancer pharmaceutical and infusional capacities. Other examples of hospitals useful for building an MSCS include, but are not limited to, a hospital with dedicated resources for molecular genetics, epigenetics and regulation, tumor microenvironment, cancer epidemiology, cancer control research, translational research programs for genitinary cancers, gastrointestinal cancers, women's cancers, or hematologic and viral-associated malignancies. Such hospitals are capable of handling about 2,000, 5,000, 8,000, 10,000, 15,000, 18,000, or 20,000 patient visits per year.

In one embodiment, a resource is a large computing facility. A large computing facility includes, but is not limited to a supercomputer center. In one embodiment, a supercomputer center comprises over 1000 CPU's on Sun Fire V20Z, X4200, and X2100 server platforms. In another embodiment, a computing facility comprises over 1 TB of distributed RAM and 40 TB of disk memory available on networked servers or similar level of computing power sufficient to enable rapid parallel computations on massive datasets.

In one embodiment, a resource is a research facility capable of applying existing proteomics and nanotechnology techniques to clinical and biological samples and capable of developing technologies for extracting more information from collected or existing biological and clinical samples. In one embodiment, a research facility is equipped with sufficient computing facility enabling reliable and reproducible data extraction, quality assurance and quantitative information from high-resolution mass spectrometric proteomics and nanosensor data. In another embodiment, a facility is equipped with capabilities to utilize computational linguistics methods for comparison of clinical annotations from multiple datasets.

In one embodiment, a resource is a modeling work resource. In one embodiment, a modeling work resource comprises genomics and systems biology tools. Genomics and systems biology tools include, but are not limited to, tools used in systems biology, comparative functional genomics & bioinformatic analysis focusing on model organisms and phylogenetically related species.

Handling of large numbers of sample requires facilities equipped with systematic sample processing capabilities. Examples of systematic processing equipment include, but are not limited to, microarray facility, massively parallel sample processors and other supportive equipments such as Agilent LC MSD Ultratrap™, SPR Flexichip and Symphony 12 channel Peptide Synthesizer, Biomek FX Robotic System™, NanoDrop™ Fluorescent plate readers, Typhoon™ image reader, Animal and Plate barcoding equipment, Hygro Culture™ system, Gene guns, high-throughput mass spectrometric immunoassay systems including Beckman™ Multimek 96 parallel robotics and Bruker Autoflex III™ linear MALDI-TOFMS, and Bruker Ultraflex III™ MALDI-TOF/TOFMS, a Bruker Microflex™ linear MALDI-TOFMS, ESI/qTOF-MS (Bruker micrO-TOF-Q™), nano-HPLC (Eksigent™), research-grade immunoaffinity extraction platform (Intrinsic Bioprobes, Inc. MASSAY™) refrigerators and freezers capable of holding for up to 5,000 samples, and other common laboratory equipment (e.g., centrifuges, analytical balances, Milli-Q water) and supplies/reagents. In some embodiments, the facilities are equipped with laboratories at biological safety level 2 (BL2+) or above for handling biological samples. In one embodiment, a method of building MSCS comprises conducting sample measurement in a facility capable of systematic sample processing. In another embodiment, a method of building MSCS comprises conducting sample measurement in a BL2+ laboratory.

MSCSs described herein may utilize animal models in their model-building stage. In one embodiment, a method of building MSCS comprises having access to a fully operational mouse facility equipped with about 3,000 or more cages. In another embodiment, a method of building MSCS comprises having access to DNA sequencing facility, microscopy facility, microarray facility, flow cytometry facility, bioinformatics facility, gamma-irradiator, tissue culture facility and virus-handling room.

Stochastic-Simulation modeling

The standard paradigm for medicine is to diagnose the patient's condition and to apply a treatment that has been determined to be effective in treating the diagnosed condition. This diagnosis-centric approach works well when patients can be assigned to categories for which there exist proven treatments. For example, the diagnosis-centric approach is highly successful in treating infectious diseases. The speciation of the underlying pathogens naturally divides the patients into equivalence classes of individuals who are likely to respond in similar ways to similar treatments. This notion of equivalent diagnosis is so fundamental to notion of effective treatment that it is the basis of most of protocols for establishing the effectiveness of treatments.

The diagnosis-centric approach is less successful in the treatment of cancer because cancer is an emergent behavior of the complex adaptive system of an animal's own body. Cancer can be viewed, without bound by a theory, an interaction between mutated and normal cells that has the potential of disrupting the broader pattern of interaction that we call health. Viewing cancer form this perspective, the problem is not an external agent, but the state of the system itself. Because the system is complex and adaptive, there is no a-priori reason to believe these bad states will group in natural categories. It is difficult to define meaningful equivalence classes for cancer that group individuals that are likely to respond in similar ways to similar treatments (for example, the difficulty in determining sub-type or response to therapy for NHL). It is necessary, therefore, to look beyond the diagnosis-centric approach.

Physical science has a paradigm for understanding and controlling complex adaptive systems. This is the dynamical systems paradigm in which the state of a system is considered as point in a multidimensional state space and the time evolution as a path through that space. This approach has been successfully applied to many complex physical systems in physical chemistry, astronomy, quantum physics, and engineering problems in telecommunications, aerodynamics, and finance. In many cases the number and complexity of components in these systems approaches that of mammalian cells Taking the dynamical systems paradigm approach, cancer can be viewed as an unstable region of the space. A cancer model built on such paradigm can prescribe new ways of selecting a treatment regime. In one embodiment, an MSCS produces a new treatment regime based on stochastic simulation following specification of initial states.

The stochastic simulation approach assumes that a system starts with incomplete knowledge of the state of the system. Rather than studying the evolution of the exact state, observation is made on the evolution of the probability density function. This enables predicting, probabilistically, the regions of the space towards which the system is likely to evolve. If specific regions of the space can be assigned a level of desirability, then conditions can be selected that is likely to increase the probability of a favorable outcome, by guiding the probability density toward the stable, healthy region.

In one aspect, stochastic simulation comprises three elements: i) a means of measuring relevant state variables and building a model of the state-evolution function of the system (e.g., modeling steps described in RP 1,2,3 and 4), ii) a means controlling variables that influence the evolution of state (e.g., therapy, intervention, experimental design centered on cell lines), and iii) a means of assigning desirability to regions of the state space (e.g., a clinical understanding of prognosis and pathology).

Cancer disrupts tissue morphology and function not only at the point of origin, but also in organs throughout the body. The host responds to the evolving cancer both locally, via the vasculature and stroma, and globally, via the immune system and secreted factors. While the disease manifests at these tissue and organism levels, it is frequently attacked at the cellular and molecular level using therapeutic agents targeting molecular linchpins of the disease, such as protein kinases responsible for growth cascades.

Bridging these scales from the molecular to the organismal remains a unique, but critical challenge. At the molecular level, tremendous advances have been made identifying the multiple mutations and epigenetic events that drive cancer progression (within an individual tumor). How these molecular events map onto cellular, tissue and organismal level disruptions is unclear. At the other end of the scale, the histological manifestations of cancer at the level of tissue morphology are used daily in the clinic to stage the disease and gauge prognosis. But, the precise molecular underpinnings of the aberrant tissue morphology are unclear.

To enable rational therapeutic strategies, MSCSs described herein interconnect these events at different length scales into an integrative platform that predicts how molecular-level interventions translate into organismal-level outcomes. In one embodiment, an MSCS is used to interrogate biological events such as how the heterogeneity of a tumor impacts drug response. In another embodiment, an MSCS is used to benchmark the accessibility of a drug to a given cell within a tumor as a function of vascularity and outputs predicted impacts of vascularity on drug's effectiveness.

Interrogating Mechanism of Therapeutic Response with Model Systems

Factors that influence chemosensitivity are typically evaluated in tumor-derived cell lines treated in culture or as ectopic grafts in nude mice, implicitly making the assumption that therapeutic response is intrinsically linked solely to a drug's impact on a particular cell, or on a near homogenous cell population. To overcome consequences stemmed from the assumption, an MSCS may utilize well-controlled, well-designed genetically defined mouse models. In some instances, cell lines explicitly coupled to those models are utilized in a complementary manner. In one embodiment, controllable variables are introduced to the model system via mouse models. Controllable variables are, for example, individual genes that can be altered or manipulated in the mouse to initiate and direct tumors to certain tissues; genetically controlled derivatives that can be generated by gene transfer into primary tumors; or a series of genetically defined yet spontaneous tumors that can be treated at their natural site with identical treatment regimens.

Genetically defined mouse models, such as acute myeloid leukemia (AML) mouse models, are a tractable experimental system that bridge cell culture and animal analysis. Mouse models represent physiological systems for testing agents or drug combinations in a way that is unfeasible in clinical trials. In one embodiment, genetically defined mouse models are used to define variable responses to conventional and targeted drug therapies. In another embodiment, treatment variables are tested and scored in terms of treatment sensitivity or the number of lesions responding to a therapy. In another embodiment, a correlation variable is generated between drug action and tumor genotype. In another embodiment, mouse model systems are used for recapitulation of typical genetic and pathologic features of human cancer. In another embodiment, mouse model systems are used for observing tumors with a benefit of a relatively short latency and high penetrance. In another embodiment, mouse model systems are used for monitoring tumor burden by non-invasive means. In another embodiment, mouse model systems are used for isolating large numbers of pure tumor cells before or after implantations for molecular and biochemical studies. In another embodiment, mouse model systems are used for performing therapy in immune competent mice.

System Applicability

In one embodiment, an MSCS comprises a virtual model for a complex disease such as cancer, including solid tumors, leukemias and lymphomas. In one embodiment, the cancer is acute myelogenous leukemia (AML). In another embodiment, the cancer is non-Hodgkins lymphoma (NHL). In another embodiment, the cancer is acute promyelotic leukemia. In another embodiment, the cancer is Burkitt's lymphoma. In another embodiment, diffuse large-B-cell lymphoma.

In one aspect, MSCSs described herein are applied to other cancers sharing characteristics with either AML or NHL. In one embodiment, an MSCS modeled on AML is applied to other primarily non-solid tumors. In one embodiment, an MSCS modeled on NHL is applied to other primarily solid tumors.

Acute Leukemia

Leukemias are neoplastic proliferations of hematopoietic cells. Most broadly, acute leukemias can be divided into lymphoblastic or myelogenous type based on phenotypic and histologic criteria. Notably, both types are composed of a large number of subtypes with radically different response to therapy. For example, development of therapy resistance is a major clinical problem encountered in treating AML. Some distinct genetic subsets responding well to targeted chemotherapy have been identified. In most cases, however, correlations between distinct molecular subtypes and differences in therapeutic response and long-term outcome have not been clearly elucidated.

MSCSs described herein provide information on therapeutic response. In one embodiment, the information is a prediction of low or non-responsiveness of host. In one embodiment, prediction of low or non-responsiveness comprises synthesizing predictive value with genetic background information. Specific cytogenetic abnormalities, including inv(16), t(15;17), t(8,21), are associated with a favorable outcome of approximately 30% risk of relapse. However, other cytogenetic abnormalities, including -5(q), -7(q) and t(11q23), are associated with over 70% of relapse. Specific genetic changes associated with some of these cytogenetic events have been identified. For example, translocation t(8;21) was found to involve a fusion of AML1 with ETO. Translocation t(11q23) was found to involve the AML gene with multiple partners, most commonly fused to AF9.

Studies suggest that AML leukemogenesis requires mutations that impair differentiation and enhance proliferation. The former often results from chromosomal rearrangements producing dysfunctional transcription factors that prevent myeloid differentiation (AML1/ETO, MLL/AF9, PML/RARalpha). The latter is often associated with hyperactivation of Ras signaling (N- or Kras, FLT3, SHP-2, Kit or NF-1). In addition to mutations described herein, other mutations such as loss of p53 or deletions chromosomes 5q and 7q can impact prognosis to varying degrees. In one embodiment, a method of building MSCS comprises utilizing known genetic information. In one embodiment, genetic information is mouse genetic information. In another embodiment, genetic information is clinical genetic information. In another embodiment, genetic information is utilized to elucidate how particular lesions affect disease progression and therapeutic response. In another embodiment, genetic information is utilized to produce a more personalized and effective approach towards treatment.

Genetically Defined Experimental Model for Leukemia

Experimental murine models for AML are used for building an MSCS. Murine strains listed in Table 1 are utilized for building an MSCS. These murine models both mimic the clinical phenotype and allow fine control of cellular machinery. In one embodiment, AML murine models are used for transplantation into syngeneic hosts for collection of data on expansion of the same disease in multiple recipients. In one embodiment, AML murine models are labeled with imaging agents for collection of imaging data. In one embodiment, AML murine models are used for monitoring response to therapy. In one embodiment, a large number of AML murine models are used for isolating cells from spleens of the affected animals and culturing cells to collect data on genotypic diversity. In one embodiment, AML murine models are used for establishing a subset of the genotypes through long term culture.

In some instances, RNAi knockdowns are employed to further analyze AML murine models. In one embodiment, a mouse model used for RNAi knockdown mimics one of the genotypes of human AML. In another embodiment, a mouse model is mosaic animal where the reconstituted hematopoietic compartment is derived from transgenic hematopoietic stem cells. In another embodiment, murine models are used for testing the impact of genetic background on responses to various therapeutics, and the efficacy of different treatment regimens in a given genotype. In another embodiment, RNAi methods are utilized to test for dysfunction of individual tumor suppressor genes in AML. In another embodiment, RNAi methods are utilized for screening applications to identify cooperating genetic events in leukemogenesis.

TABLE 1

Murine strains.

| Genotype | Phenotype |
| --- | --- |
| MLL/AF9 | aggressive AML; chemoresistant |
| MLL/AF9 + FLT3ITD | very aggressive AML; chemoresistant |
| MLL/AF9 + Nras | very aggressive AML; chemoresistant |
| MLL/ENL + Nras | very aggressive AML; chemoresistant |
| AML1/ETO9a | smoldering AML; chemosensitive |
| AML1/ETO9a + AML1/ETO | moderately aggressive AML; chemo untested (likely sensitive) |
| AML1/ETO9a + Nras | moderately aggressive AML; chemosensitive |
| AML1/ETO9a + Nras + p53null | aggressive AML; chemoresistant |
| Nras + p53null | moderately aggressive AML; chemo untested (likely resistant) |
| Kras + p53null | moderately aggressive AML; chemo untested (likely resistant) |
| FLT3ITD + p53null | moderately aggressive AML; chemo untested (likely resistant) |
| LSL-Kras + p53null | moderately aggressive AML; chemoresistant |

Aggressive Lymphoma

Lymphoma encompasses a diverse group of diseases which represent malignant growth of lymphocytes. There is tremendous heterogeneity across the disease spectrum. Some lymphomas are among the most rapidly growing tumors known. These variants of lymphoma can be rapidly fatal, but are also uniquely responsive to combinations of cytotoxic chemotherapy and radiotherapy. A particularly aggressive form of lymphoma is known as Burkitt's lymphoma. Burkitt's lymphoma was initially identified based on histologic criteria which included small cells with high mitotic and proliferative rates and the presence of apoptotic cells. Early application of cytogenetic analysis provided insight into the etiology of Burkitt's lymphoma as many cases were identified with dysregulation of the MYC oncogene via a translocation event involving the immunoglobulin heavy chain locus. The most common form of adult lymphoma is known as diffuse large-B-cell lymphoma which is curable in about half of patients with combination chemotherapy (CHOP, cyclophosphamide, vincristine, doxorubicin, vincristine)

Genetically Defined Experimental Model for Lymphoma

Murine strains listed in Table 2 are utilized for building an MSCS. Eµ-myc mice overexpress the c-myc oncogene in the B-cell lineage, and the resulting B-cell malignancies resemble human Non-Hodgkin's lymphomas. In one embodiment, murine models are used to recapitulate typical genetic and pathological features of human Non-Hodgkin's lymphomas. In one embodiment, murine models are used for collecting large amount of data within relatively short period of time by taking advantage of short latency and high penetrance. In one embodiment, murine models are used for monitoring tumor burden by lymph-node palpation or blood smears. In one embodiment, murine models are used for isolating large numbers of pure tumor cells from enlarged lymph-nodes for biochemical measurements. In one embodiment, murine models are used for performing therapy in immunocompetent mice. In one embodiment, murine models are used for culturing and transplanting lymphoma cells into syngenic, non-transgenic recipient mice. In one embodiment, Eµ-myc lymphomas are used for creating tumors with defined genetic lesions. These murine models are assessed for the relationship to treatment responses using procedures that parallel clinical trials. In one embodiment, murine models are used for tagging of tumor cells with fluorescent proteins and monitoring of tumor burden by in vivo imaging in live mice.

TABLE 2

Lymphoma Model Systems

| Genotype | Phenotype |
| --- | --- |
| Eµ-Myc | moderately aggressive B-cell lymphoma, variable response to CTX |
| Eµ-Myc/Bcl2 | very aggressive B-cell lymphoma, medium resistant to CTX |
| Eµ-Myc/Arf−/− | very aggressive B-cell lymphoma, slightly resistant to CTX |
| Eµ-Myc/p53−/− | very aggressive B-cell lymphoma, highly resistant to CTX |
| Eµ-Myc/Tsc2−/− | very aggressive B-cell lymphoma |
| Eµ-Myc/CyclinD1 | very aggressive B-cell lymphoma |
| Eµ-Myc/TRE-CyclinD1 | |
| Eµ-Myc/TRE-Akt | |
| Eµ-Myc/TRE-p53 shRNA | very aggressive B-cell lymphoma |
| p53−/− | T-cell lymphoma |
| PTEN−/− | T-cell lymphoma |
| TRE-PTEN shRNA | T-cell lymphoma |
| TRE-Akt | T-cell lymphoma |
| TRE-PTEN shRNA/p53−/− | |
| Bcr-Abl | aggressive B-ALL/B-Lymphoma |
| Bcr-Abl/Arf−/− | very aggressive B-ALL/B-Lymphoma |
| Bcr-Abl/p53−/− | very aggressive B-ALL/B-Lymphoma |
| TRE-PTEN shRNA/NotchIC | T-cell lymphoma (model in development) |
| TRE-p53 shRNA/PTEN−/+ | T-cell lymphoma (model in development) |

The Eµ-myc model is useful for identifying cancer genes (e.g., by insertional mutagenesis or RNAi screens) and other aspects of cancer biology. For example, either loss of the ARF or p53 tumor suppressor genes can cooperate with Myc to promote aggressive B cell lymphomas in mice. The response of the genotypes can be quite variable to conventional chemotherapy such as cyclophosphamide. For example, lymphoma lacking ARF responds particularly well to cyclophosphamide while those lacking p53 respond poorly. In one embodiment, murine models are used for collecting data on various perturbations, such as drug treatment, of an MSCS. In one embodiment, relation between genotypic variants and response to conventional (cyclophosphamide) and targeted (BCL2i) therapy are examined.

Mechanistic Modeling of AML and Lymphoma

Both acute and chronic myeloid leukemia may be modeled using population dynamic methods. In these methods, the cancer cell population is divided into multiple subpopulations or compartments (e.g., stem cells, progenitor cells, pre-malignant cells, tumor cells, chemoresistant tumor cells), with ordinary or stochastic differential equations governing the transitions of cells between these subpopulations. For example, ordinary differential equations may model apoptotic, quiescent, maturing, and proliferative pools in AML. In other models, the G, S, and M phases of the cell cycles are included to model lymphoblastic leukemia cell populations; a delay differential equation is used to build a population dynamic model of AML; an ODE model is used to relate single mutations to the age of AML incidence; and applied control theory is used to optimize therapy in population dynamic tumor models. However, in various embodiments, MSCSs as described herein differ in that the MSCSs provide models of leukemia in heterogeneous organs, capable of showing the impact of oxygen and drug gradients on response to therapy, or leukemia cell motion in specific organ geometry, such as the spleen.

Lymphoma modeling may focus primarily on population dynamic modeling governed by systems of differential equations, such as modeling immunotherapy in B-cell lymphoma, modeling the Knudson 2-hit hypothesis in lymphomagenesis and other lymphomagenesis hypotheses, and modeling cell cycle kinetics. A single-cell model may include p21-Myc dynamics in determining the apoptotic response of individual cells in B-cell lymphoma to therapy. A compartmental model of a single lymphoma cell (including growth medium, cytosol, and nucleus compartments) may be used to quantify the dynamics of drug response. However, in various embodiments, MSCSs as described herein differ by providing models of lymphoma capable of predicting whole-tumor evolution or understanding the spatiotemporal dynamics. In one embodiment, MSCSs described herein utilize spatial modeling which models extravasation, diffusion, and binding of monoclonal antibodies in spherically-symmetric lymphomas.

Modules of MSCS

Figure 4:
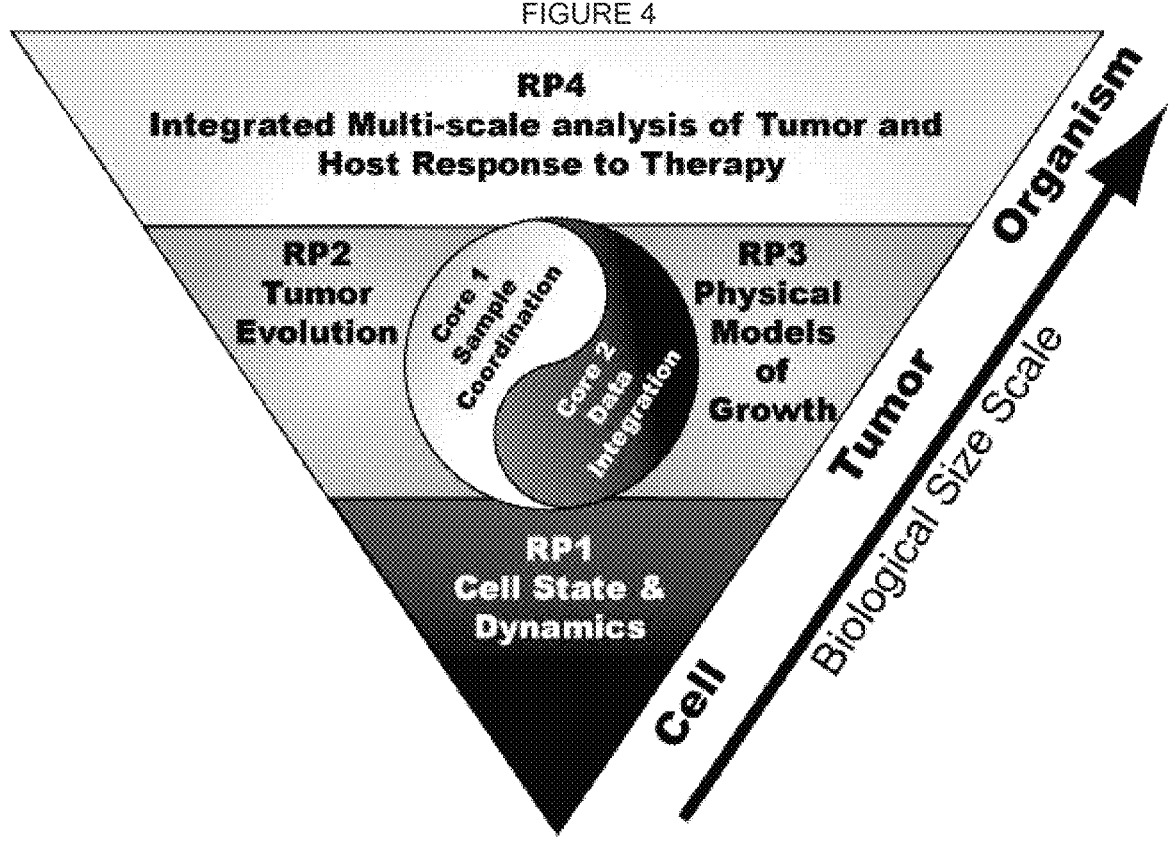
FIG. 4 illustrates relations among modules of an MSCS.

As illustrated in FIG. 4, an MSCS comprises multiple modules (e.g., RP1, RP2, RP3 or RP4). These modules interact with each other in a synergistic manner to create a virtual tumor able to accurately predict the steady state growth and response to therapy of a real tumor. In one embodiment, an MSCS comprises two or more modules described herein. In another embodiment, an MSCS further comprises evaluation and optimization components for each module and for the overall performance of an MSCS.

An RP1 module comprises data on cell- and molecular-scale phenomena. In one embodiment, RP1 module generates state space models of cellular behavior and response to therapy. In one embodiment, information from RP1 module is transmitted to RP2 and RP3 modules in the form of a cellular phenotype. In one embodiment, a cellular phenotype is a broad characterization of the current state of the cell. In another embodiment, a cellular phenotype is likely near-term trajectories of the current state of the cell as inferred by perturbations to the cellular network.

RP2 module comprises data on tumor-scale phenomena. RP3 module comprises data on organ-scale phenomena. In one embodiment, RP2 module models the evolutionary progression of a tumor. In another embodiment, RP2 module models in-host evolution of genetic heterogeneity of a tumor. An RP3 module comprises analytic components. In one embodiment, an analytic component is analysis of mechanical properties of a tumor. In another embodiment, an analytic component is analysis of microenvironmental properties of a tumor. In another embodiment, an analytic component is analysis of tumor's growth and response to therapy. In another embodiment, RP2 or RP3 modules collect sophisticated imaging data. In another embodiment, RP2 or RP3 modules collect cell and molecular-phenotypic information from Rpl. In another embodiment, RP3 module comprises an analytic function in which it characterizes phenomena such as growth of vasculature, distribution of nutrients and impact of environment on individual cells. In another embodiment, RP3 module comprises reductions or subsets of models derived from RP1 and embedded in tumor-level models.

An RP4 module comprises analytic and evaluative functions in which the module characterizes a host-scale response to a tumor. A host includes any mammal such as human, mouse, or monkey. In one embodiment, RP4 module integrates the data collected across the whole collection modules and generates a singular integrated virtual tumor model.

In some MSCSs, more than one RP1, RP2, RP3, or RP4 modules are used. In one embodiment, all modules are physically contained within single computer. In another embodiment, each module is located in geographically distant place but virtually connected via network servers.

Structure of the Virtual Tumor Model

Described herein are the structures of MSCS. In one embodiment, the system is a multi-scale complex system. In another embodiment, the multi-scale system is adaptive. A system is designed to be adaptive either by a set of feed-back logic, neural computing methods, or via user intervention. The adaptive process can be automatic, periodic, intermittent, continuous or non-continuous.

Figure 5:
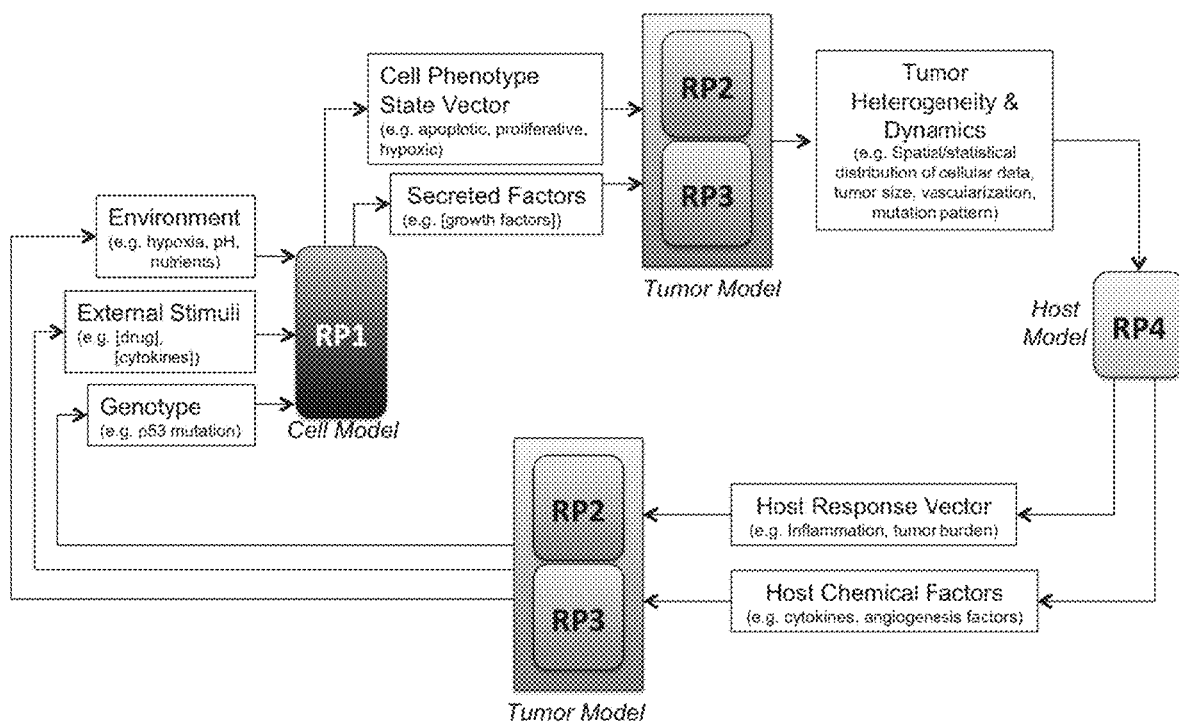
FIG. 5 illustrates an exemplary structure of an MSCS.

In one aspect, an MSCS has a hierarchical structure. In one embodiment, each of cellular, multicellular/tissue, multi-cell type (tissue with local vasculature and stroma), or organismal (tumor+entire host, e.g. immune) events are integrated as a separate module. In one embodiment, each module is assigned to a level corresponds to a rank in the hierarchy. In one embodiment, a lower level feeds data into a higher level. In another embodiment, two or more lower levels feed data into one top level. In another embodiment, levels are arranged in a tandem manner so that outcomes from one level (e.g., cell) serves as inputs to another level (e.g., multi-cell). An example of hierarchical structure is illustrated in FIG. 5.

In one aspect, an MSCS has a minimal model structure in which each level itself contains a subsystem. In one embodiment, a subsystem comprises a core subset of factors (inputs, parameters) that reliably map onto the relevant outcomes of the sub-system. Reliable mapping is enabled by, for example, placing weights on genes and proteins that are particularly active in the modeled cancer. In another embodiment, at the cell level, core subset of molecular signatures are determined based on collected data and utilized to predict cell level outcomes (e.g., division, motility, apoptotic, survival, etc.).

In one aspect, an MSCS has hybrid modeling framework. In one embodiment, both physical/mechanistic and statistical models are used to generate a hybrid computational framework. In another embodiment, functional mapping between input variables and outcomes are performed. This mapping is complemented with coarse-grain mechanistic models where mechanistic information is uncovered. In another embodiment, a hybrid modeling framework is used to generate a multi-scale framework that connects molecular components to organismal level progression of cancer.

In one aspect, an MSCS is used for systematic in silico evaluation of therapeutic strategies. In one embodiment, an MSCS is a self-learning system in which repeated use of the system for the in silico evaluation and continuous feed of experimental data leads to improved accuracy in prediction. In some embodiments, an initial hierarchical model is first built on current knowledge in the field. It may then be refined based on experimental findings to improve its predictability to perturbations, resulting in testable hypotheses of cancer mechanisms and treatment response. In some embodiments, the MSCS systems utilize Monte Carlo algorithms. In some embodiments, the MSCS systems utilize Metropolis-Hastings algorithms. In some embodiments, the MSCS systems utilize simulated annealing algorithms. In some embodiments, the MSCS systems utilize genetic algorithms.

Experimental Design

Experiments are performed in a unified manner, on the same system and frequently on the same sample, or samples from the same host.

Figure 6:
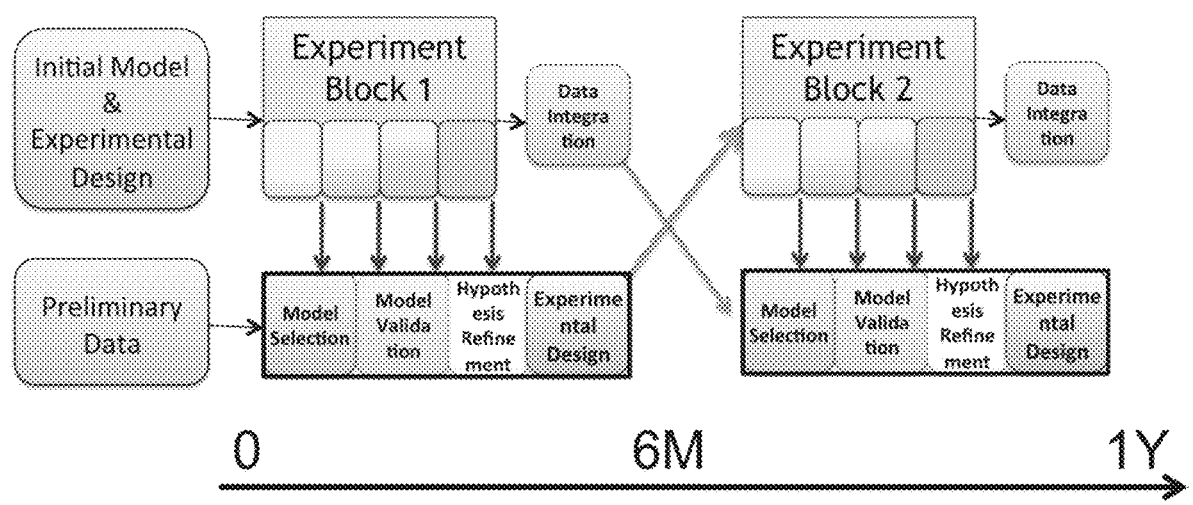
FIG. 6 illustrates iterative Experiment/Modeling Strategy.

FIG. 6 illustrates general iterative strategy. Experiments are conducted as guided by starting hypothesis and eventually by hypothesis derived from virtual model. An iterative strategy ensures that data are collected purposefully and that virtual tumor models are being developed and refined on a continuing basis with the data needed to progress the models to gradually more complex models. Experimental design includes a set of treatment parameters. The parameters include, but are not limited to a selection of treatment approach, e.g. one or more drugs, radiation treatment, nutritional component, treatments involving the delivery of thermal energy etc., as well as specific doses and time schedule of one or more selected treatment approaches. An experimental design may include any combination and sequence of treatment approaches with the selected parameters. In one embodiment, an iterative development cycle is about 4-6 months. In various other embodiments, an iterative development cycle is about 1-2 months, 2-3 months, 2-4 months, 2-6 months, 4-8 months, 4-12 months, 8-16 months, 8-24 months or any other range having any of these values as end points (e.g. 2-12 months). To minimize cycle time, experiments are planned in discrete sub-blocks, which are providing continual input to modelers. In one embodiment, as data is collected, they are organized to be immediately available to models. In one embodiment, a complete experimental block comprises 1, 2, 3, 4, 5, 6, 7, 8, 9, 10, 11, 12, 13, 14, 15, 18 or 20 experiments in which each of the pairings between sensitive models and resistant models treatment or non-treatment with a cytotoxic agent. In one embodiment, a sub-block is a single treatment condition in a single model. In one embodiment, subsequent iterations after the initial iteration are performed. In one embodiment, a subsequent iteration step is integrating the data collected on each of the different scales of inquiry. In one embodiment, computational models are refined and validated using the data, leading to a refined model. In one aspect, an MSCS is built on data collected from animal models and perturbations listed in Table 3.

TABLE 3

List of models and perturbations

| Disease | Model | Perturbation |
|---|---|---|
| AML | MLL/AF9 + Nras | None |
| AML | AML1/ETO9a + Nras | None |
| AML | MLL/AF9 + Nras | Cytarabine + Doxorubicin |
| AML | AML1/ETO9a + Nras | Cytarabine + Doxorubicin |
| NHL | Eμ-Myc/p53−/− | None |
| NHL | Eμ-Myc/Arf−/− | None |
| NHL | Eμ-Myc/p53−/− | Cyclophosphamide (CTX) |
| NHL | Eμ-Myc/Arf−/− | Cyclophosphamide (CTX) |
| AML | MLL/AF9 + Nras | Pathway Targeted Therapy (Nutlin-3a, Rapamycin) |
| AML | AML1/ETO9a + Nras | Pathway Targeted Therapy (Nutlin-3a, Rapamycin) |
| AML | MLL/AF9 + Nras | RNAi |
| AML | AML1/ETO9a + Nras | RNAi |
| NHL | Eμ-Myc/p53−/− | Pathway Targeted Therapy (oblimersen) |
| NHL | Eμ-Myc/Arf−/− | Pathway Targeted Therapy (oblimersen) |
| NHL | Eμ-Myc/p53−/− | RNAi |
| NHL | Eμ-Myc/Arf−/− | RNAi |
| AML | MLL/AF9 + Nras | Additional Mutations |
| AML | AML1/ETO9a + Nras | Additional Mutations |
| AML | MLL/AF9 + Nras | Additional Mutations + Cytarabine + Doxorubicin |
| AML | AML1/ETO9a + Nras | Additional Mutations + Cytarabine + Doxorubicin |
| AML | TBD System | None |
| AML | TBD System | RNAi |
| NHL | Eμ-Myc/p53−/− | Additional Mutations |
| NHL | Eμ-Myc/Arf−/− | Additional Mutations |
| NHL | Eμ-Myc/p53−/− | Additional Mutations + CTX |
| NHL | Eμ-Myc/Arf−/− | Additional Mutations + CTX |
| NHL | TBD System | None |
| NHL | TBD System | RNAi |
| AML | MLL/AF9 + Nras | bevacizumab |
| AML | AML1/ETO9a + Nras | bevacizumab |
| AML | TBD System | zoledronic acid |
| AML | TBD System | zoledronic acid |
| NHL | Eμ-Myc/p53−/− | bevacizumab |
| NHL | Eμ-Myc/Arf−/− | bevacizumab |
| NHL | TBD System | zoledronic acid |
| NHL | TBD System | zoledronic acid |
| AML | Human | CHOP |
| NHL | Human | CTX |
| AML | MLL/AF9 + Nras | combination therapy |
| AML | AML1/ETO9a + Nras | combination therapy |
| AML | TBD System | combination therapy |
| AML | TBD System | combination therapy |
| NHL | Eμ-Myc/p53−/− | combination therapy |
| NHL | Eμ-Myc/Arf−/− | combination therapy |
| NHL | TBD System | combination therapy |
| NHL | TBD System | combination therapy |

In one embodiment, the data obtained from these experiments are utilized to form an initial set of hypotheses about sensitivity and response. In subsequent experimental iterations, the same experimental design is used to challenge and/or validate initial physical model with sets of biologically derived data.

In one embodiment, a standard therapeutic induction regimen such as cytarabine and anthracycline combination chemotherapy is used for AML modeling. In one embodiment, an MLL/AF9+Nras− genotype, which is an aggressive, chemotherapy resistant animal model, is used For AML modeling systems. Data collected from the animal model is then contrasted to an AML1/ETO9a+Nras− animal model, which is moderately aggressive and responsive to chemotherapy. As a control, an AML1/ETO9a+Nras+p53− animal model, which is moderately aggressive; and resistant to chemotherapy, is used.

In another embodiment, therapy based on cyclophosphamide, anthracyclines, and other agents in various combinations are used for aggressive NHL modeling. In one embodiment, an Eμ-Myc/Arf−/− animal model, which is sensitive to cyclophosphamide, is used for aggressive lymphoma. The data is then contrasted to an Eμ-Myc/p53−/− animal model which is resistant.

In some instances, animal models described herein are challenged via RNAi or shRNAs targeting techniques to specifically inhibit key genes. In one embodiment, a key gene is VEGF or p53. In some instances, other perturbators are used including, but is not limited to, MDM2 inhibitors (Nutlin-3a), mTOR inhibitors (rapamycin), Mek inhibitors (U0126, PD0325901), Pi3K inhibitors (LY294002, PI103), Bcl2/Mcl1 inhibitors (ABT-737, Obatoclax), Proteasome inhibitors (Bortezomib), Histone deacetylase inhibitors (Vorinostat, Depsipeptide), Farnesyl transferase inhibitors (Zarnestra®), FLT-3 inhibitors (CEP-701, Sorafenib), Demethylating agents (Decitabine), bevacizumab and zoledronic acid.

Data Measurement

Table 4 details platforms, their measurement capabilities and how their data fit into MSCSs.

| Technology | Measurement | Sample | Data | Model component |
|---|---|---|---|---|
| Multiplex SPR | Protein interaction | Mutant and modified proteins | Protein kd vs mutation | Cellular interaction network |
| Phosphoflow | Protein phosphorylation | Cultured or captured cells | Single cell protein phosphorylation state | Cellular network dynamics |
| LC-LCMS/MS | Protein expression | Cultured cells | Cell surface/whole cell protein abundance | Cellular network dynamics |
| RNA microarray | Gene expression | Cultured or captured cells | Gene expression change | |
| MagnetoNanosensor | Protein abundance | Multiple | Expression by protein | Network, growth |
| Protein microarray | Antibodies/host response | Serum | Ab activity by protein | Network, host response, growth |
| CGH/oligonucleotide array | Gene copy number, epigenetics | Tumor | Copy number, loh, epigenetic markers (e.g. Methylation) by cytogenetic band | Chromosomal, growth |
| Intravital microscopy | Tumor imaging | Tumor | Tumor mass, vasculature, spatial distribution of markers | Morphology, growth |

| Technology | Measurement | Sample | Data | Model component |
|---|---|---|---|---|
| Basic pathology | Histology | Tumor | Tumor grade, phenotype | Morphology, growth |

Dynamic State Space Modeling of Cancer Cell Response to Therapy

To generate a dynamic state space model of cancer cell's response to therapy, modules are produced on experimental data ranging from measuring protein abundance, protein interactions to protein modification. In some embodiments, the experiments are performed in genetically defined animal models of specific cancers. In some embodiments, the cancer is AML or NHL. In certain embodiments, these measurements are integrated using computational methods to analyze the topology of regulatory and signaling networks and dynamic parameters of these networks. To facilitate this analysis, experiments are optionally performed as time series and different measurement technologies (e.g., measurements of protein modification, protein levels and protein interactions) are carried out on cells drawn from synchronized samples. In one embodiment, biochemically detailed, real-time protein interactions are measured. In another embodiment, the abundance and types of protein modifications are measured. In another embodiment, shotgun proteomics are used to collect data and computational methods are used to reconstruct regulatory networks.

Many of the measurable changes in a cell at the molecular level are likely to be insignificant from the perspective of the tumor due to, for example, the redundancy and extreme robustness of cellular networks. Small numbers of molecular-scale perturbations (e.g. mutation in a gene) can produce a dramatic, tumor-scale (e.g. invasiveness) or organism scale (e.g. positive outcome) effects. In one embodiment, techniques to reduce the complexity of molecular and cellular events are used. These techniques include, but are not limited to, mapping from a small set of inputs such as genetic background of a cell, environmental context to a small set of outputs cell physiology, cell state, or likelihood of state change.

In one aspect, a module comprises genomic datasets. In one embodiment, a module comprises synchronized measurements of regulation and signaling events critical to cancer progression and response to therapy. The module is useful for developing accurate mathematical models of cellular behavior, response to endogenous and exogenous perturbation or alteration to correlate molecular perturbations (environmental, genetic, physiological) with models of tumor and disease. In one embodiment, a module is built from experimental data collected on the response of acute myelogenous leukemia (AML) to cytosine arabinoside (cytarabine, AraC) with an anthracycline. In another embodiment, a module is built from data on the response of Burkitt's lymphoma to cyclophosphamide. In one embodiment, a module shows how genetic alterations lead to differences in responsiveness to chemotherapy. In one embodiment, data on specific cytogenetic events relevant to AML is incorporated into the module. Examples of specific cytogenetic events include, but are not limited to, translocations like t(8;21) that generates a fusion of AML1 with ETO and t(11q23) that fuses the MLL gene with multiple partners or any event conferring different sensitivity to chemotherapy. In another embodiment, effect of common deletions, such as P53 or ARF, are measured in modeling differential sensitivity in Burkitt's lymphoma. In one embodiment, integrate measurements are performed for protein interaction dynamics in a multiplex SPR instrument. In another embodiment, high-throughput measurements of single-cell protein phosphorylation are performed. In another embodiment, mRNA expression is measured. In another embodiment, cell-surface, intracellular and secretory events are measured by proteomes approach.

In one embodiment, both the topology and the kinetic parameters of the networks active in AML and NHL are reconstructed from data obtained through various measurements. In one embodiment, a module is built from the data with the Inferelator algorithm (Bonneau et al, Genome Biology, 7:R36, 2006). In another embodiment, the module is used to describe perturbations to multi-leveled network as alterations to rate. For example, it is expressed as the effect on protein A binding to protein B as a function of the level of protein C. Another example is effect of protein A binding to protein B as a function of the protein level and phosphorylation state of C, or the rate of transcription of D as a function of E and a complex between G and H. In deriving the module, synchronized multi-level data compendium and prior knowledge about pathways are used to generate a system of differential equations that describe the topology and multi-time scale dynamics of the regulatory and signaling networks active in the tumors. In one embodiment, the resulting dynamic network module is incorporated to an MSCS to predict future cell states. In another embodiment, the resulting dynamic network module is incorporated into tumor-scale.

Described herein is a method of building a reduced state space model of cellular dynamics in response to chemotherapeutic intervention and genetic alteration. In one embodiment, model building comprises in the step of: 1) constructing learn modules from a combination of relevant datasets; 2) parameterizing kinetic parameters of one or more known networks active in a studied cancer; 3) expanding known network learning directly from data, and 4) simulating the outcome of perturbations and compare to observations to design experiments. In another embodiment, the method further comprises design aspect in which experiments are designed to specifically improve model accuracy over proteins, genes, or interactions that are critical to tumor-level. In some embodiments, the studied cancer is AML or NHL.

In one aspect, data useful for a module measure critical cellular parameters at genome and proteome levels that impact cell physiology in cancer. In vitro primary culture and cell-line models can be used to define the quantitative changes in the transcriptome and in the intracellular, cell-surface and secretory proteomes of lymphoma and leukemia in response to different genetic alterations and perturbations. In addition, measurement is performed for dynamics of changes of phosphorylation status of up to 2, 3, 4, 5, 7, 10, 15, 20, 25, 30, 40, 50 or more proteins on a per cell basis across resistant and sensitive lines on a single-cell basis.

In one aspect, a module assesses the relationship between genotype and phenotype for key proteins in murine models for studied cancers. In some embodiments, the studied cancer is AML or Burkitt's lymphoma. Known clinical mutations in the genes for relevant proteins are selected for measurement. Measurement can be performed in an array format. The effect of one or more of these mutations on key relevant macromolecular interactions is measured for kinetic variables such as $K_D$, $K_{on}$, $K_{off}$.

Figure 7:
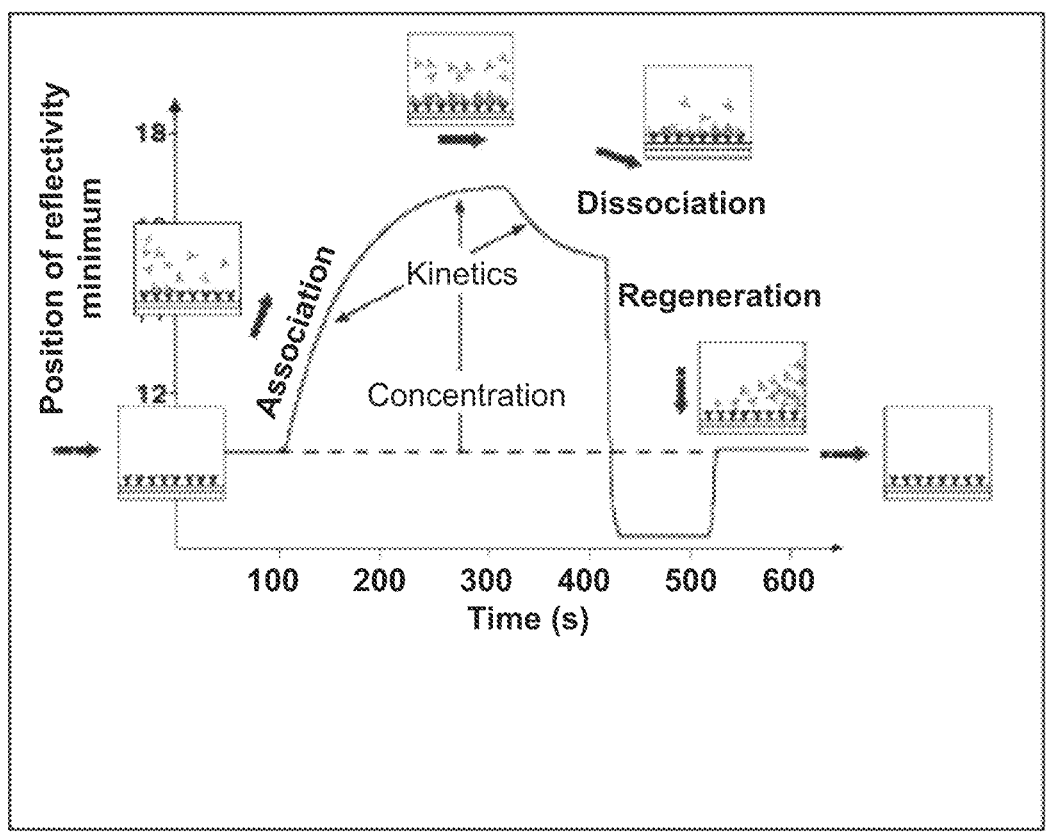
FIG. 7 illustrates a binding curve of various biochemical processes involved in bimolecular interactions.

Several mechanisms have evolved to regulate protein interactions, including post-translational modifications (PTMs), activator or inhibitor molecules, and modulation via protein abundance. Aberrant interactions lead to dysregulation of cellular function and ultimately diseases, such as cancer. A mechanistic understanding of the underlying biochemistry of these events is critical for the development of therapeutics and diagnostics. Understanding of these interactions in quantitative terms of kinetics and affinities are important to develop wiring diagrams that correctly model protein functional behavior. In one embodiment, binding parameters, protein modifications and protein levels are measured in real time to incorporate the effects of modification and other molecular factors on complex formation into models. In one embodiment, Surface Plasmon Resonance (SPR) is used to measure interactions among molecules of varying sizes and affinities. In another embodiment, interactions of proteins with other proteins, peptides, small molecules, and DNA with micromolar affinities are analyzed by flowing a query molecule over an immobilized target, and by monitoring changes in refractive index in real-time to generate binding profiles (FIG. 7). These profiles contain association kinetics of the initial binding phase (on rate, $K_{on}$) followed by an equilibrium phase (stochastic steady state) where the signals plateau. Dissociation kinetics (off rate, $K_{off}$) is measured by flowing wash buffer. SPR sensitivity depends on both the total mass of analyte that binds and the proximity of binding to the surface. In some instances, SPRi is used, which is a variant of SPR in which the angle of refraction is optimized and fixed in a linear range and the signal intensity of the refracted light is measured. Different capture proteins are printed in specific regions on the sensor surface and the query molecule is then flowed over the entire surface, allowing the scaling of SPR to thousands of proteins.

In one embodiment, flow cytometry is used to elucidate signaling at the single-cell level. Differences in signaling biology is revealed by responses of a representative group of signaling nodes to a set of environmental cues when these nodes are queried across a set of diverse tumor networks. In one embodiment, specific lymphoma cell subsets are compared with cancer cell function and host immune system function. In another embodiment, phosphorylation changes associated with transformation of follicular lymphoma (FL) B cells into more aggressive types of lymphoma (e.g., DLBCL) is measured by analysis of specific signaling networks.

In one embodiment, a method for producing proteins in situ called nucleic acid programmable protein array (NAPPA) is used to generate data. Full-length cDNAs corresponding to the proteins of interest are printed on the microarrays and then transcribed/translated in situ at the time of assay. The protein is produced using a cell-free, in vitro transcription and translation (IVTT) coupled rabbit reticulocyte lysate (avoiding type biases that a non-mammalian expression system could introduce) and captured on the array through a high-affinity reagent that recognizes an epitope tag appended to each cDNA. This procedure produces arrays that show little variation day-to-day. In one embodiment, up to about 10,000 different proteins are expressed using NAPPA. In one embodiment, proteins generated by NAPPA are used for displaying proteins for testing on SPRi devices.

Gene expression levels and protein composition in a particular cell represent valuable information about a therapeutically responsive state or a therapeutically non-responsive state. The modification of the proteins within the cell is also critically important to cellular regulation and dysregulation. In one embodiment, proteomic analysis is partitioned into a subset of data comprising intracellular, cell-surface and secretory proteomes. In one embodiment, protein affinity chromatography is used in concert with mass spectrometry to identify proteins differentially expressed on the cell surface in several disease models. In one embodiment, a cell-surface protein is Her-2.

The understanding of network cross-talk and other more global topological phenomena (and the differences in these topologies in disease or cells of varying phenotype) require a principled multivariate approach. Regulatory networks that accurately predict the time evolution of whole-genome transcript levels can be recognized as cells transitioning between distinct cell states. In one embodiment, a model comprises networks (e.g., systems of differential equations) that reproduce regulatory dynamics of cells as they transition between cell states and respond to environmental changes.

Three classes of proteins are used to define a cancer, (e.g. AML or NHL). First, host factors are used to serve as a proxy to tumor status, such as proteins involved in inflammation (e.g. TNF-alpha, IL-6, IL-1alpha, IL-1beta, beta-microglobulin), angiogenesis or cytokine markers (e. g. VEGF, FGF-2, MMP-9, IL-8, IL-6, HGH, sTr-2, VCAM-1, sVEGFR1). Second, proteins previously implicated in the cancer (e.g. lymphoma/leukemia) are used, including Myc, PI3K, PTEN, AKT, MTOR, P70SK, TP53, JAK, STAT, BCL2, XIAP or BAD. Third, genes known to have mutations that impact prognosis or response to therapy in the cancer (e.g. AML or NHL) are used, including key mutations found in MLL such as NRAS, the nucleophosmin gene (NPM1), the CCAAT/enhancer binding protein alpha gene (CEPBA), the fms-related tyrosine kinase 3 gene (FLT3), the Wilms tumor 1 genes (WT1) or RUNX1. In one embodiment, activation of RAF/MAPK/ERK pathway is monitored as it is frequently associated with various cancers, including both AML and lymphoma. In another embodiment, mutations in this pathway including those in NRAS (and other RAS family members), FLT3, PTPN11 and BRAF are examined.

Learn Modules

Modules are defined as the co-regulated groups, co-regulated complexes and co-regulated pathways active in two cancer models. Integrative biclustering algorithm such as cMonkey is used to learn these condition dependent biclusters. In one embodiment, first generations of data compendium is integrated with public microarray datasets, public proteomics datasets, and known signaling pathways and protein interactions using cMonkey. Literature-derived edges, such as bioGrid or bioNetBuilder can be used to constrain module construction. In one embodiment, biclusters (i.e., groupings of genes and the conditions the group is coherent over) produced by cMonkey and other tools are linked to the evidence for those groups (network edges and links back to annotations for component genes), creating biclusters supported by genetic association data, expression, known signaling and putative protein-protein interactions. In one embodiment, evidence-linked data are used to elucidate strongest regulatory controls on each biclusters. In one embodiment, validation methods for human cancer biclusters are developed by focusing on extracting a number of known, high-quality modules from the AML and NHL literature. In one embodiment, scoring functions are developed to integrate the SNP and copy number data-types into the module.

Parameterizing Kinetic Parameters of Known Networks Active in Models and Relevant Cell Types/Models Kinetic parameters are built by using a pre-specified topology. The topology of the starting model is taken from very large number of cancer relevant regulatory, signaling and protein-protein interactions already known to date. In A pre-specified topology based model is used for various purposes. In one embodiment, the model is used to explore and gauge the strengths and deficiencies of the model. In another embodiment, the model is used to design experiments. In another embodiment, the model is used to define a baseline of performance with respect to predicting the outcome of experiments.

True parameters are determined by main data input associated with RP1 module, a curated network representing known signaling, regulatory and protein-protein interactions between genes expressed in AML and NHL. In one embodiment, the Inferelator is used to find optimal kinetic parameters and return ensembles of differential equation-based models where the parameters are chosen such that they respect the input topology and optimally fit the initial data. In one embodiment, data fitting produces a system of equations that can be directly used to predict dynamics, determine incomplete parts of the model and design experiments to improve the model.

Phospho-Flow Signaling Analysis of Phospho-Protein Targets and Upstream Activators for Interrogation of Immune Signaling Complex combinations of FACS and quantitative measurements are used to classify and isolate cells of interest. Parameters associated with each cell are used as data pointing to the heterogeneity of individual malignant cells in a population where subsets of cells have acquired defined oncogenic signaling properties (e.g., activating mutation of a signaling molecule). In some embodiments, phospho-flow is used to investigate a number of proteins involved in oncogenic signaling. In various embodiments, the number of investigated proteins involved in oncogenic signaling is 2 to 5, 5 to 10, 5 to 15, 10 to 20, 15 to 30, 20 to 50 or any other range having these values as endpoints (e.g. 30 to 50). In some embodiments, the investigated proteins are involved in the AML signaling. Some of these proteins are listed in Table 5.

Antibody Validation, Protocol Optimization, and Quality Control

To accomplish synchronized measurement, appropriate protocols for fixation, permeabilization, blocking, and staining of all cell types are established. Different permeabilization and denaturation steps are optimized. Antibodies are tested on cell lines where the appropriate kinase or phospho-protein is known to exist as per published references. Antibodies are conjugated using standard procedures or by using protein-protein/protein-dye cross-linking kits. Quantitation of fluorescent probe conjugation is assessed by standard protocols to determine degree of labeling. siRNA or small molecule inhibitors can be used to validate antibody specificities.

The kinase substrates are chosen based on their known association with immune activation. Phospho-flow technology is used to measure the kinetics of phosphorylation of multiple substrates simultaneously. Using parallel measurements, the entire phospho-landscape is defined with kinetic constants. This analysis is used to define the dynamic crosstalk between the pathways as well as establish causality between the signaling pathways and transcriptional activation.

A device, such as the CyTOF™ mass spectrometer (a mass spec/flow cytometer hybrid), is used to perform 50-parameter flow cytometry. ICP-MS is used to determine the elemental composition of materials used for ultra-trace detection of metals and other elements. A high-temperature plasma (the fourth state of matter) is created through the coupling of radiofrequency (rf) energy into a flowing inert gas (usually argon). For detection, a quadrupole mass filter is used for which current technology provides approximately 7 orders of magnitude abundance sensitivity (resolution between adjacent mass channels) and 9 orders of dynamic range. Suitable element-tagging reagents were developed in order to demonstrate the detection technology. The prototype tags that are currently available employ an acrylate polymer backbone functionalized with chelators that bind lanthanide ions tightly (K is about $10^{-16}$). With an ICP-MS efficiency of 1 ion detected per $4 \times 10^4$ atoms introduced to the plasma, the current detection limit is of the order of 400 copies per cell.

Information gained through experiments is used to select proteins useful for cancer models. A series of mutant proteins based on clinically detected mutations in cancer is created. Quantitative functional consequences of these

TABLE 5

Example upstream activators of lymphoid signaling pathways

| Activator | Pathway(s) | Description |
|---|---|---|
| IL-2 | STAT | Mitogenic cytokine that signals through Stat1, Stat3, and Stat5. |
| IL-3 | STAT | Stimulator of Stat5 signaling as part of myeloid cell proliferation. |
| IL-4 | STAT | Signals through Stat6. Exhibits potent anti-tumor activity in lymphoma. |
| IL-6 | STAT | Stimulates B cell growth and plasma cell differentiation through Stat3 activity. |
| IL-10 | STAT | Upregulated by CD20 activity and involved in an anti-apoptotic feedback loop. |
| IFN-α | STAT, MAPK | Signals via Stat1, Stat2, Stat3, and Stat5, as well as p38. 146. |
| IFN-γ | STAT | Employs Jak1 and Jak2 and signaling primarily through Stat1. |
| CpG ODN | TLR/MAPK | Signals via TLR9 for innate immunity. |
| LPS | TLR/MAPK | Signals via TLR4 for innate immunity. |
| TNF-α | MAPK | Activator of p38 and JNK pathways in B cells 147-149. |
| a-IgM | ICS, MAPK | Stimulates BCR signaling through proteins in lipid rafts. |
| G-CSF | STAT, MAPK | Potent stimulus of myeloid cell proliferation and differentiation through Stat3. |
| GM-CSF | STAT, MAPK | Potent stimulus of myeloid cell proliferation and differentiation through Stat5. Also drives signaling via MAPK pathways. Receptor is a member of the gp140 family. |
| CD3/CD2 | TCR | Signaling reagent leading to TCR activation and activation of downstream Syk, |
| CD40L | ICS/STAT/NFκB | Implicated in activation of Lyn, NF-κB 150 Stat3 151, MAP, p38, and ERK. | mutants are measured as a function of protein interaction behavior using NAPPA-coupled SPR.

Cancer Evolution Space-Time Machine

Genomes are able to record ancestry because genomes are almost perfect copies of copies. The greater the numbers of divisions since a common ancestor, on average the greater the number of differences between genomes (a molecular clock hypothesis). In one embodiment, molecular phylogeny is used to reconstruct the past of species and populations to record variations in normal or neoplastic somatic human cells. In another embodiment, molecular phylogeny is used to reconstruct human somatic cell ancestry. In another embodiment, conventional cell fate markers are used in experimental systems.

Tumor genomes become polymorphic after transformation, and these variations record ancestry, or how fast it took for a single transformed cell to become the present day tumor population. In one embodiment, human acute myelogenous leukemia specimens are examined for variations. In another embodiment, epigenetic somatic cell molecular clocks based on DNA methylation patterns are examined. In another embodiment, ancestry information is provided in combination with mouse genetics information to translate the mouse studies to human diseases.

Figure 13A:
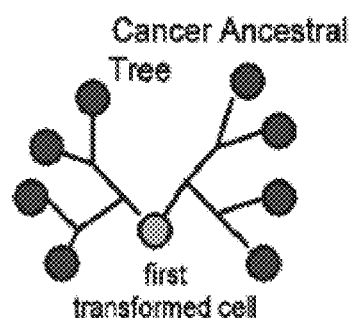
FIG. 13A and FIG. 13B illustrate clonal origin of a tumor.

Cancers are clonal populations: they start from a single transformed cell. Growth occurs by binary fission: a cancer cell divides to produce two nearly identical daughter cells. A visible tumor has billions of cells, each of which is related to the first transformed cell (FIG. 13A). Every tumor can be represented by a binary branching ancestral tree that starts with the first transformed cell and ends with present day cancer cells.

Something new (neoplasia) is created with a defined start at a single point in time. Cancers characteristically exhibit Gompertzian growth in which the inflation of cell numbers is initially exponential ($2^N$), but the growth rate progressively decreases as the size of tumor increases. Visible tumors (>1 cm$^3$) grow very slowly. Interestingly and as expected from an initially rapidly expanding population, many human cancers are circular or spherical.

Figure 13B:
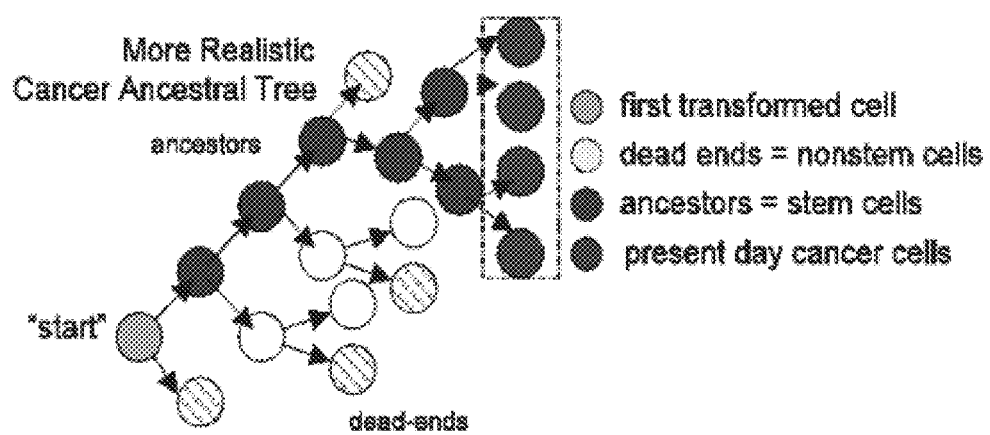

One possible consequence of such an "inflationary scenario" is that tumors are initially fairly homogeneous cell populations because they are only a few divisions removed from each other (FIG. 13A). However, most human cancers exhibit heterogeneity—different parts of the same tumor do not have identical properties. It is uncertain how this heterogeneity arises, but one likely source of tumor heterogeneity is that although tumor growth slows with expansion, cell division continues. Many cancer cells die such that cell division becomes balanced by cell death and ancestral trees become pruned (FIG. 13B). This pruning or cell extinction complicates modeling because a population may arise via a large number of possible trees.

Ancestral trees can be defined with just three types of cells (FIG. 13B): the start (first transformed cell), present-day cells, and no-longer-present-day cells. No-longer-present-day cells can be subdivided into ancestors (with present day progeny) and dead ends (no present day progeny). Ancestors are analogous to cancer stem cells (CSCs) and dead ends are non-stem cells.

A relevant biological time may differ from chronological time. For example, all cells in an adult have the same chronological age, i.e., time since conception, but some new cells have recently divided whereas other cells last divided decades ago. Time is defined thus as mitotic age or the number of divisions since conception. Every cell has a defined mitotic age, which may differ between cells and can change with chronological time. The mitotic age of a cancer is the number of divisions since the first transformed cell.

A tumor is subdivided into discrete biologically well-defined individual cells and their genomes. In the beginning, there is the first transformed cell and a specific genome. The present day cancer is composed of billions of transformed cells arrayed in space that are essentially almost perfect copies of the first transformed cell and its genome.

Methods described herein track ancestry to travel both forwards and backwards in time. Going forwards in time means starting from a single transformed cell, the number of cells increases exponentially and the simulation becomes progressively more complex. Going backwards means the numbers of cells and lineages become progressively smaller the further back in time, the simpler the situation, as shown in FIG. 14.

Figure 14A:
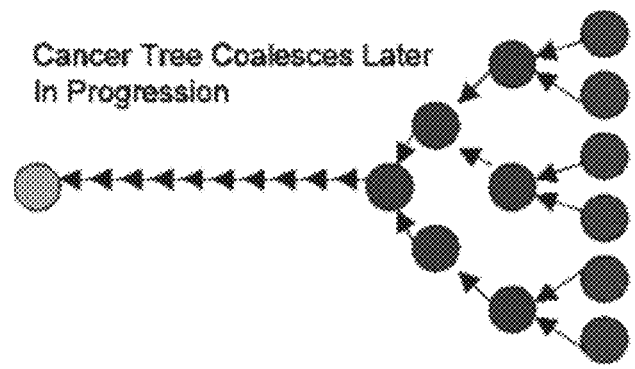
FIGS. 14A and 14B illustrate time traveling along the axis of tumor progression.
Figure 14B:
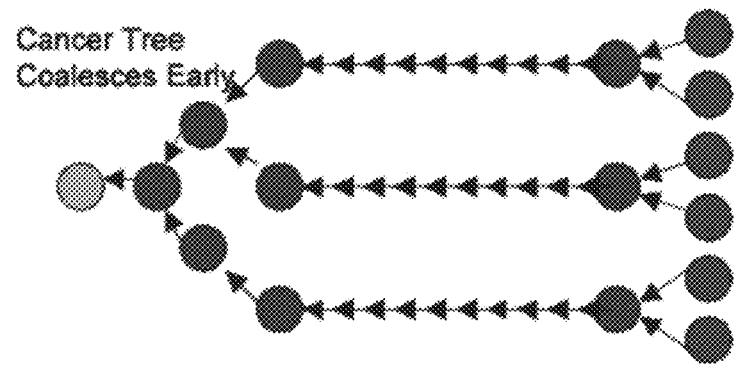

The structure shown in FIG. 14 is called the coalescent. Without being bound by theory, any two cells within a cancer should eventually share a common ancestor and subsequently share the same ancestry back to the first transformed cell. The problem becomes smaller and more tractable because one has to trace the behaviors of ancestors. The coalescent provides a computationally succinct architecture to simulate the biology of cancers in great detail.

Molecular phylogeny is a well-developed branch of biology and is routinely used to infer the structure of populations and the ancestry of species by comparing present day genomes. The idea is that all genomes are almost perfect copies of copies-the greater the differences between two genomes, on average the greater the times since a common ancestor (a molecular clock hypothesis). Genome differences can be described as pairwise distances (Hamming distance) or the number of differences at analogous sites.

Genomes also contain epigenetic information that is also copied and passed from generation to generation. For example, DNA cytosine methylation at CpG sites is usually copied after DNA replication by DNA methyltransferases (FIG. 15)

In one aspect, a model uses somatic cell molecular clocks based on methylation pattern variation. DNA methylation patterns are a 5' to 3' binary code (methylated or unmethylated at a CpG site) measurable by bisulfite sequencing. (After bisulfite treatment, methyl-C remains a C whereas C is converted to a T). DNA methylation pattern replication fidelity appears to be less than base replication fidelity and therefore it is very common to find methylation pattern heterogeneity in normal and cancer human tissues. At certain CpG rich regions, the replication error rate has been estimated to about 10,000-fold higher than the mutation rate ($10^{-5}$ versus $10^{-9}$ per division). This higher drift or replication infidelity allows for a practical somatic cell epigenetic molecular clock because somatic variation quickly accumulates in individual cancer cells, and their methylation patterns should also coalesce (FIG. 15). In one embodiment, a model uses epigenetic clock loci. In one embodiment, high throughput sequencers are used to measure methylation. In another embodiment, variation of methylation at a given CpG site is measured.

Figure 16:
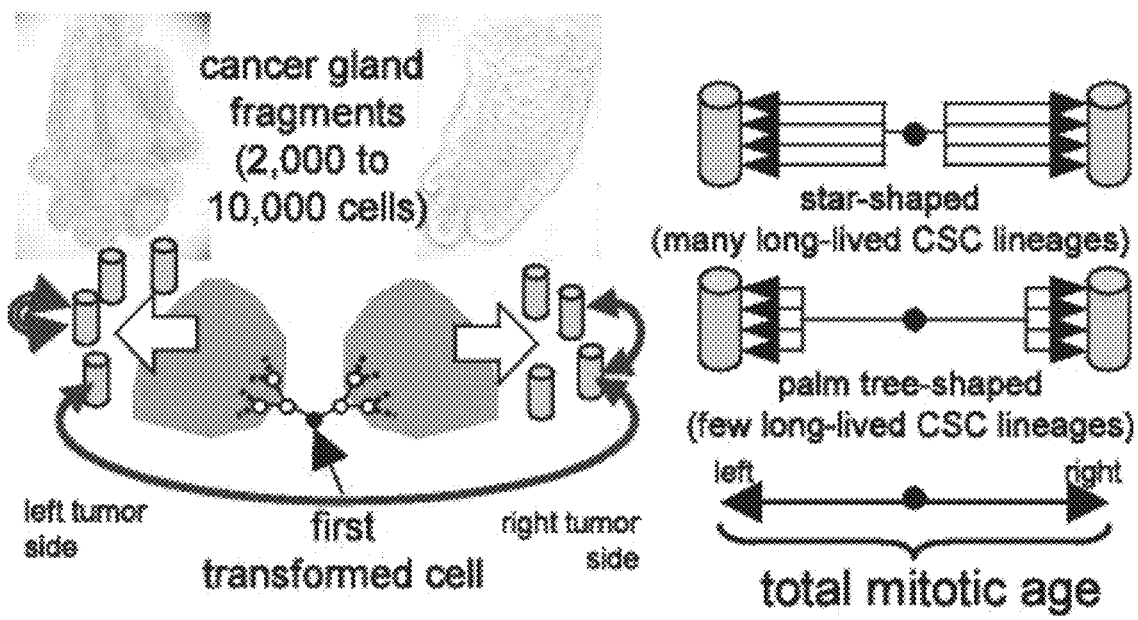
FIG. 16 illustrates space approach in tracing ancestry.

Methods described herein use space to infer time. Space is useful because in an inflationary scenario, cells physically located on opposite sides of tumor are likely to share a common ancestor around the time of transformation whereas cells closer together may be more closely related. In one embodiment, adjacent cancer cells from different parts of the same tumor are isolated to use space information to model and test the model (FIG. 16).

Many cancers such as colorectal cancers are constructed of tubular cellular structures called glands that subdivide a tumor so that daughter cells tend to remain nearby. These glands can be physically sampled (~10,000 cells) and analyzed. In one embodiment, a molecular clock is calibrated by comparing genomes from opposite cancer sides. Genomes from opposite cancer sides should have the maximum number of pairwise differences and represent the mitotic age of the cancer because these cells last shared a common ancestor around the time of transformation. In one embodiment, the pairwise distances between cells from opposite cancer sizes are compared with pairwise distances between adjacent cells within the same cancer gland. If pairwise distances within a gland are similar to the distances between cells from opposite cancer cells, then the cancer ancestry tree is essentially a star-shaped phylogeny with many long-lived cancer stem cell lineages (i.e., coalesces early as in FIG. 14). However, if pairwise distances between cells within a gland are much smaller than between opposite cancer sides, the phylogeny is palm tree-shaped with more infrequent cancer stem cell lineages (i.e., coalesces later in FIG. 14).

Figure 17:
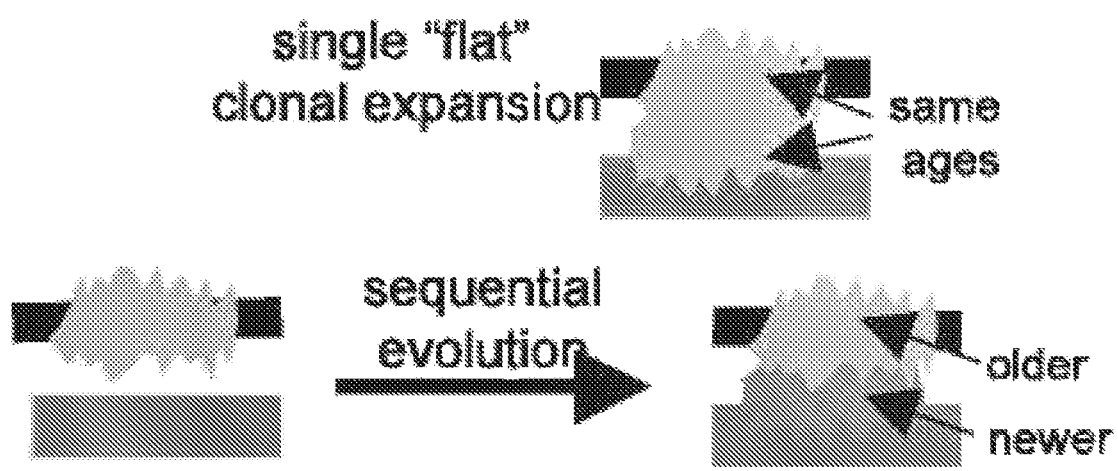
FIG. 17 illustrates flat or sequential expansion of cancer.

In one embodiment, a comparison is made for methylation patterns between opposite cancer sides and between adjacent cells within cancer glands. Depending on whether or not having similar mitotic ages or ancestries among the compared groups, cancer can be identified as originated from single clonal expansion (the flat expansion in FIG. 17) or as originated from different subclonal expansions as cancer cells acquire new capabilities during sequential progression (FIG. 17). A newer clonal expansion would have less diversity because fewer divisions separate its progeny from a common ancestor.

Figure 19:
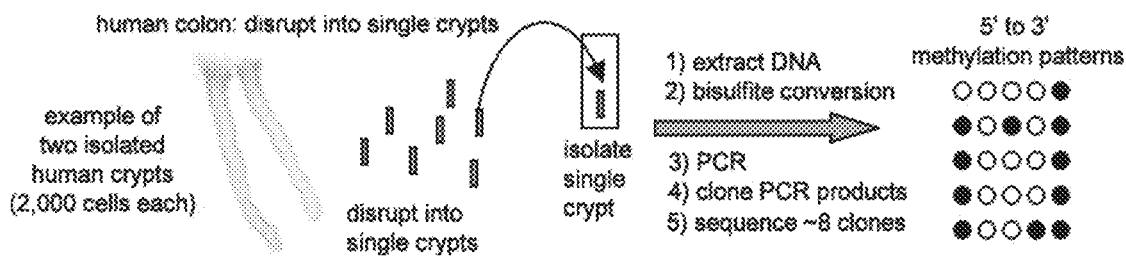
FIG. 19 illustrates an exemplary procedure for generating an epigenetic somatic cell clock from a human colon.

CpG methylations at certain CpG rich human genome sites are useful for epigenetic somatic cell clocks. In one embodiment, an epigenetic somatic cell clock is used to trace tumor ancestry. Examples of two different CpG rich regions that exhibit "clock-like" behavior are displayed in figure FIG. 18. In another embodiment, epigenetic somatic cell clock is produced for multiple normal human tissues. In one embodiment, an epigenetic somatic cell clock is produced from human colon. For example, a human colon is disaggregated into single crypt (clones of about 2,000 cells), bisulfite treated, and then amplified by PCR. The PCR products are cloned into bacteria, and individual clones are sequenced. This samples individual epialleles from the single crypt population (FIG. 19)

Figure 25:
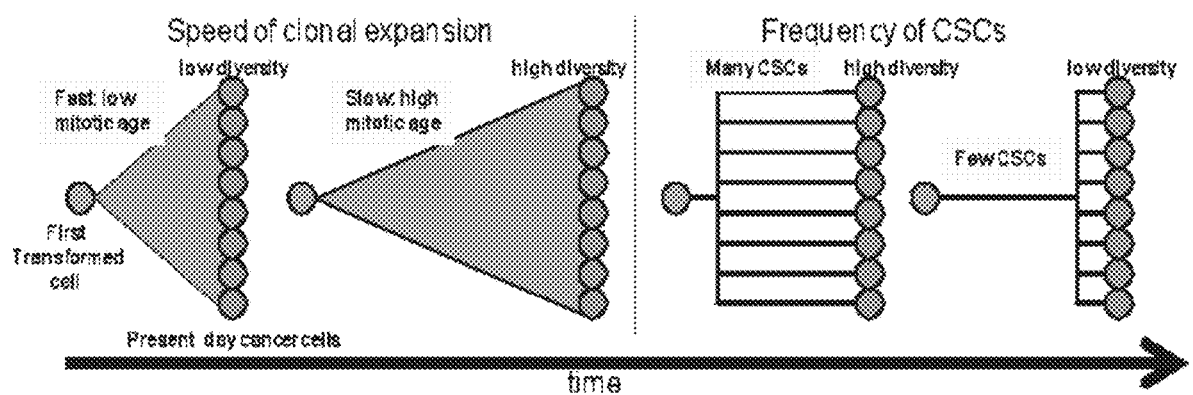
FIG. 25 illustrates speed of clonal expansion and frequency of cancer stem cells.

In one embodiment, the amounts of genomic diversity between present day tumor cells are measured to distinguish between these very basic ancestral trees. For example, FIG. 25 illustrates simple ancestries based on the speed of the clonal expansion and the frequencies of long lived cancer stem cell (CSC) lineages. An ancestral tree itself can be a "phenotype" of the present day tumor because it diagrams its long-term behavior. For example, a very rapid clonal expansion that occurs over several weeks implies a very aggressive tumor phenotype. A more indolent clonal expansion that occurs over several years implies a less aggressive tumor phenotype. The frequencies of long-lived CSC lineages have clinical implications. In one embodiment, a parameter utilized for the modeling comprises the frequency long-lived CSCs. In another embodiment, a parameter utilized for the modeling comprises rate of clonal expansion. In another embodiment, a parameter utilized for the modeling comprises tumor diversity. Table 6 illustrates various combinations of these parameters and potential phenotypic outcomes.

TABLE 6

Modeling parameters.

| Tumor | Clonal expansion | CSCs | Tumor diversity | Phenotype |
|---|---|---|---|---|
| A | Rapid | Few | Low | Aggressive, most tumor cells destined to die |
| B | Rapid | Many | Medium | Aggressive, most tumor cells propagate |
| C | Slow | Few | Medium | Indolent, most tumor cells destined to die |
| D | Slow | Many | High | Indolent, most tumor cells propagate |

Multiscale Cancer Modeling: From Cell Phenotypes to Cancer Spread and Response to Therapy Biophysical variables are incorporated to a modeling system to link molecular and cell-scale variations in the tumor and the microenvironment to the tumor's growth. In one embodiment, quantitative relationships between complex cancer phenomena at different scales are elucidated by coupling discrete (cell-scale) and continuum (tissue-scale) models. In one embodiment, intravital microscopy (IVM) time-course measurements of tumor growth, vascularization, and chemotherapy response are recorded. In another embodiment, data on animal shape model development is recorded. Precise measurements of key model parameters that uniquely constrain the model is considered and added to the system. Additional independent tests for model validation and testing are performed.

To build an integrative multiscale cancer model, physical principles governing tumor growth and therapeutic response across broad spatiotemporal scales (seconds to months and molecular to whole-organ) are investigated by methods and systems described herein. In one embodiment, an integrative modeling is used to incorporate these responses into a model. Integrative modeling is performed by, for example, doing experiments helpful for shaping model development and calibration. Calibrated simulations are performed to generate correlations and links between microenvironment, phenotype, and tumor dynamics. In various embodiments, the model is an MSCS. In some embodiments, the model is an acute myeloid leukemia (AML) model.

In one aspect of modeling, complex relationships between cancer phenomena at different scales are quantified. In one embodiment, a hybrid, multiscale framework is used to dynamically couple discrete (cell-scale) with continuum (tissue-scale) models. In one embodiment, this framework is integrated with intravital microscopy (IVM) time-course measurements of tumor growth, vascularization, and chemotherapy response. Direct integration is useful because it provides 1) animal data that shape model development; 2) precise measurements of key model parameters that uniquely constrain the model; 3) a platform for additional, independent tests for model validation and testing; and 4) an opportunity for integrative modeling. In one embodiment, an integrated model is used for calibrated in silico experiments. In another embodiment, an integrated model is used to generate to new biological themes that can be tested in follow-up experiments in mice.

In one aspect, integration comprises incorporating cell-scale model, molecular-scale signaling model, directly linking cell phenotype, microenvironment, and genetics to these models and incorporating tumor evolution model. Integrated model is useful for adding insights on the biophysical mechanisms linking molecular and cell-scale variations in the tumor and the microenvironment to the tumor's growth; developing techniques to rapidly incorporate experimental data into the multiscale framework and determine their impact on the tumor-microenvironment system; investigating and quantifying the spatiotemporal dynamics of tumor response to therapy; and improving the in vivo-in silico development feedback loop that forms the backbone of integrative modeling.

In various embodiments, the modeling variables for a virtual cancer model include, but are not limited to, pathobiology, tissue microarchitecture, mechanical characteristics of the tumor and host cells and tumor-microenvironment interactions. In some embodiments, the virtual cancer model mimics the growth and therapy response of lymphoma in a single lymph node. In another embodiment, a virtual cancer model mimics AML in the spleen.

Figure 28A:
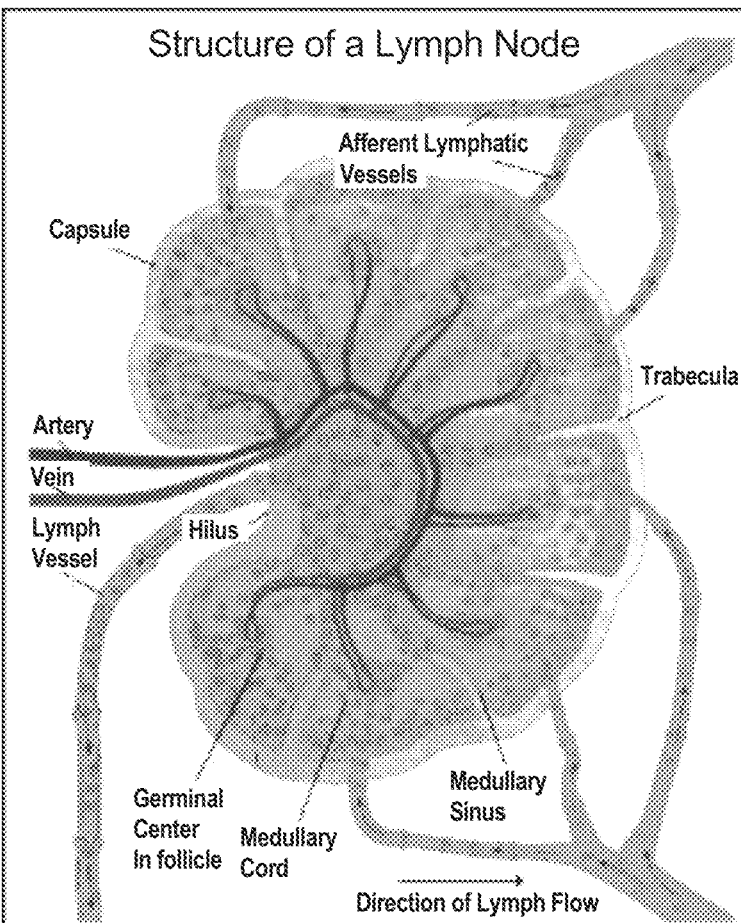
FIG. 28A and FIG. 28B illustrate the lymph node and the spleen.

The lymph node is a small organ consisting of a fibrous capsule that surrounds and supports the cortex and medulla (FIG. 28a). Lymph fluid enters the gland through afferent vessels that drain into the subcapsular sinus just inside the capsule. From there, lymph slowly filters through the cortex, into the medulla, collects in the medullary sinus, and exits through efferent vessels. The cortex consists of multiple nodular, relatively dense follicles that primarily contain B-cells, each surrounded by more diffuse lymph tissue and supported by trebeculae extending from the outer capsule. The medulla primarily contains T-cells (another lymphocyte type). The cortex and medulla are given extra support by the extracellular matrix (ECM) and a network of reticular fibers to which lymphocytes adhere via integrins. Both B and T-cells in the lymph gland exhibit heterophilic cell-cell adhesion, particularly between ICAM-1(CD54) and LFA-1 (CD11a/CD18).

Figure 28B:
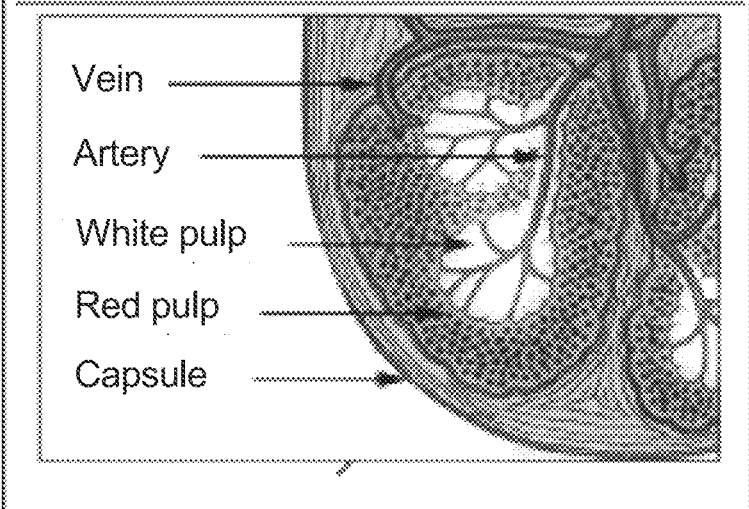

B-cells tend to express both LFA1 and ICAM-1 while inactive T-cells tend to express less ICAM1. Depending upon their immune activation, both B- and T-cells can migrate, in amoeboid fashion, and can exit the lymph node through efferent vessels. The spleen is similarly structured of an outer capsule containing red pulp (sinus-containing tissue similar to the lymph nodes' medulla), interspersed with nodular white pulp (similar to the follicles in the lymph node) containing primarily B-cells (FIG. 28b).

Lymphoma cells are known to retain cell-cell adhesion, with strength associated with the lymphoma's originating cell type (B- or T-cell). Both lymphoma and AML can secrete matrix metalloproteinases that lead to the degradation of the ECM. Both cancers are also well-known for cell migration, both within the organ and through the connecting lymph vessels. Hypoxia and subsequent angiogenesis are known in lymphoma. In AML, there is some evidence of angiogenesis (e.g., circulating VEGF-A). The presence of VEGF in AML may relate to proliferation and migration due to the common progenitor of endothelial cells and leukocytes.

In one aspect, intravital tumor and vascluartures are imaged and the image information is integrated into a model. In some instances, molecular imaging, animal imaging techniques, or intravital microscopy (IVM) is used either alone, or in combinations. Imaging can be regional or whole-body of an animal. Regional imaging can be coupled with intravital microscopy (IVM) to achieve much higher spatial resolution. In one embodiment, imaging data are turned to parameters reflecting in vivo dynamics of an animal. In one embodiment, nanoparticles are used to image specific sets of cells, matrices, or interactions within, between or among cells and matrices. In another embodiment, location information, dynamic movements or temporal movements of nanoparticles are monitored and quantified. In one embodiment, MSCS described herein are utilized to investigate effectiveness of nanoparticles in therapy. In one embodiment, biodistribution of nanoparticles throughout a tissue is measured.

In one aspect, murine studies are integrated with human studies by employing the same measurements made on the murine studies on the human specimen. In one embodiment, a murine study is a mouse leukemia study and a human specimen is a human AML specimen. In one embodiment, mouse protein and RNA measurements is performed on the human AML specimens. In one embodiment, levels of critical factors identified in the mouse studies are compared to human specimens. In one embodiment, specific sets of parameters identified as important in certain neoplastic phenotypes in the mouse AML models are measured in the human specimens. In one embodiment, a cellular parameter state identified in the mouse models is associated with specific ancestral histories (i.e., aggressive disease with frequent CSCs). In one embodiment, same translocations (e.g., AML/ETO and MLL fusion protein) in mouse and human AML are measured. In another embodiment, other conserved or shared events between mouse and human AML specimens are measured.

As solid tumors, adjacent lymphoma cells tend to remain physically in close proximity. Therefore, similar to the colorectal cancer studies, physical distances can be compared with pairwise methylation pattern differences. In one embodiment, lymphoma proliferation models are tested on other lymphomas, such as human lymphomas with MYC activation, for model's applicability. In one embodiment, the lymphoma is a high grade Burkitt's lymphoma. In one embodiment, cancer ancestry is reconstructed by measuring epiallele variation in different parts of a lymphoma microdissected on a microscope slide. In another embodiment, the mouse and human lymphomas are compared to find any similar proliferation phenotypes.

The mitotic age and ancestry of human AML can associate with specific clinical parameters. For example, certain AML subtypes can be associated with more acute or abrupt clonal expansions and clinical presentations. In one embodiment, molecular data such as routine clinical cytogenetics or CNV studies are associated with each human AML specimen. In another embodiment, specific alterations are associated with a particular ancestral phenotype.

Described herein is a tumor growth and therapy response model. The model can be an agent-based, cell-scale model of normal and cancerous cells or a multiscale continuum model of tumor growth angiogenesis and chemotherapy. The model can also be dynamic multiscale methods to couple these models. In one embodiment, 3D adaptive multi-grid solvers for fourth-order nonlinear problems are used to build a model. The agent model treats individual cells as physical objects acting under conservation laws with biology incorporated as constitutive relations. The continuum model treats tissue as a mixture of various cell species, water, and extracellular matrix (ECM); each component is subject to physical conservation laws with motion governed by Cahn-Hilliard-type equations. These models are non-symmetric and treat multiscale tumor evolution in 2D and 3D and dynamically couple growth, vascularization, and tissue biomechanics in heterogeneous tissue. In one embodiment, the cell-scale is tied to the tissue-scale models.

3D Continuum Model Capabilities

Figure 32:
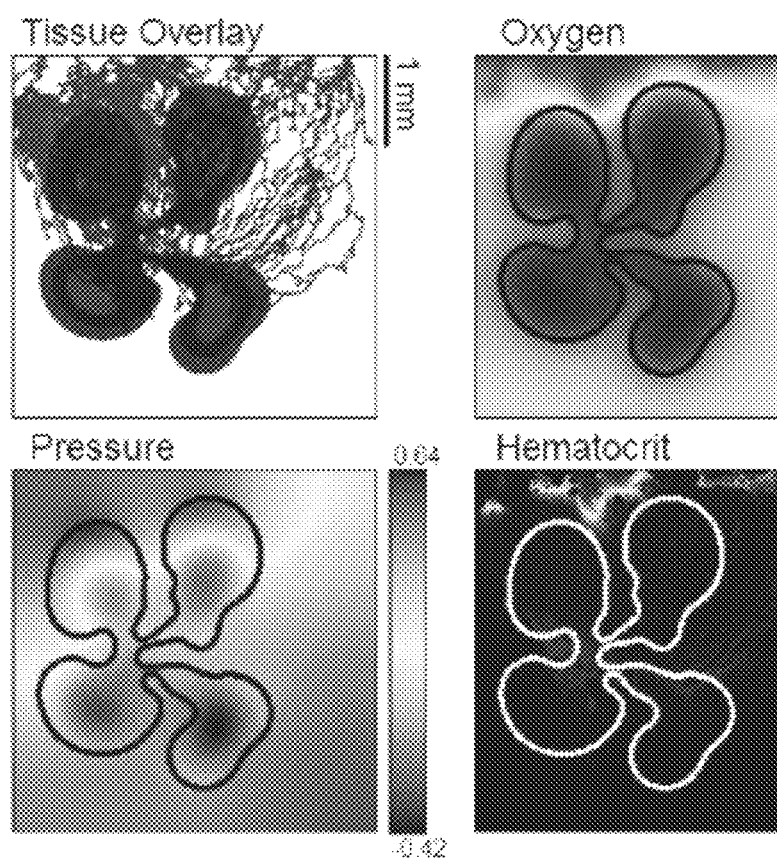
FIG. 32 illustrates Tumor-induced angiogenesis and vascular tumor growth.

In one aspect, a method of modeling comprises dynamic nonlinear links between the tumor and the microenvironment. In one embodiment, a tumor growth model is coupled with an angiogenesis model that grows in response to VEGF and other proteins released by hypoxic tumor cells. In another embodiment, the model accounts for non-Newtonian network blood flow with blood hematocrit data. In another embodiment, the model accounts for vascular network remodeling caused by wall shear stress and tumor-generated mechanical stress. For example, FIG. 32 shows nonlinear coupling of tumor growth and angiogenesis (top left), substrate transport (top right), mechanical stress (bottom left) and non-Newtonian microvascular blood flow (bottom right).

Tumor-generated stress can collapse vessels and disrupt extravasation, thereby affecting subsequent network remodeling, nutrient and drug delivery, and tumor response. In one embodiment, the virtual tumor alters the tissue biomechanics by secreting ECM and matrix metalloproteinases (MMPs) that degrade the ECM. This affects tissue mechanics and tumor cell motility (through altered ECM stiffness and integrin binding sites). Biochemical interactions affect angiogenesis by altering cell haptotaxis and tumor growth along paths of least resistance. In one embodiment, alterations are modeled through functional relationships between ECM density, tissue compliance, cell mobility, and cell taxis.

In one embodiment, heterogeneous tissue parameters are used to model complex tissue structures, such as white and gray matter and cranium in virtual brain cancer and lumen in breast cancer. In one embodiment, apoptosis is coupled to compartmental models of drug transport and cytotoxicity in tumor cells to rigorously calibrate tumor chemotherapy response. In another embodiment, such model is combined with models of drug extravasation transport through the tissue.

Agent-Based Cell-Scale Model

Described herein is an agent-based cell-scale model. In one embodiment, an agent is a cell. In another embodiment, an agent is a physical object in a biological system. In one embodiment, an agent is a normal or cancerous cell. In one embodiment, an agent-based system treats individual cancerous or non-cancerous cells as physical objects subject to conservation laws. In another embodiment, an agent-based model comprises molecular and cell-scale measurements. In one embodiment, each cell is modeled as a semi-deformable sphere with individual radius r, mass m, distribution of surface adhesion receptors $\mathcal{A}_{Ig}$ and $\mathcal{A}_{In}$ (immunoglobulin and integrin-type molecules for heterophilic cell-cell adhesion) and $\mathcal{A}_B$ (integrins for cell-BM adhesion), position x, velocity v, and phenotypic state S (proliferating P, apoptosing A, migrating M, quiescent Q, necrotic N, or calcified debris C). In one embodiment, each cell has an individual copy of the gene-protein signaling model that directly links the cell's phenotypic state to the local microenvironmental conditions (nutrient and growth factor levels, ECM density, or drug concentration). In one embodiment, the microenvironmental state is determined by the continuum model and the vasculature is given by a separate hybrid model. In one embodiment, cell agent is assigned a unique identifier embedding the agent into tumor ancestry history based upon these identifiers. In one embodiment, once the cell is committed to P, M, A, or N, a completion time is defined as $\beta_P^{-1}$, $\beta_M^{-1}$, $\beta_A^{-1}$, and $\beta_N^{-1}$, respectively.

In one embodiment, cells are assumed not able to leave P, M, or A prior to completion, except to enter N or A during therapy. In one embodiment, the cell's velocity is obtained by balancing the sum of forces acting upon it such as cell-cell adhesion and repulsion, cell-basement membrane (BM) adhesion and repulsion. In one embodiment, the net force of migration balances with interstitial fluid drag and cell-ECM adhesion by an inertialess assumption, allowing explicit determination of velocities for a cell i at positions $x_i$:

Here, φ is a family of potential functions (with parameters R representing maximum interaction distance and n controlling the shape of the potential) that model cell-cell and cell-BM interactions. In some embodiments the potential functions take the following form:

$$\phi(x; R, n) = -\frac{R}{n+2}\left(1 - \frac{\|x\|}{R}\right)^{n+2} \text{ if } \|x\| < R, \text{ and } \phi = 0 \text{ otherwise.}$$

In particular, $2r_{cca}$ represents a maximum interaction distance for cell-cell interaction, $2r_{ccr}$ represents a maximum distance for cell-cell repulsion and $r_i$ represents a maximum interaction distance for cell-BM adhesion or cell-BM repulsion, while $n_{cca}$, $n_{cba}$, $n_{ccr}$, and $n_{cbr}$ are power parameters controlling the shape of the potential for cell-cell adhesion, cell-BM adhesion, cell-cell repulsion, and cell-BM repulsion, respectively. In various embodiments, $\alpha_{cca}$, $\alpha_{cba}$, $\alpha_{ccr}$, and $\alpha_{cbr}$, are parameters modulating the relative contributions of the potential functions associated with cell-cell adhesion, cell-BM adhesion, cell-cell repulsion, and cell-BM repulsion, respectively, to the velocity function. In one embodiment, $F_{i,migration}$ represents the contribution of the migration force to the velocity.

The potential functions have compact support (i.e. are zero outside a closed, bounded region), thus enforcing realistic finite interaction distances.

Organ Geometry

Described herein is a lymph node model. In one aspect, to accommodate lymph node expansion, a model assumes moving tumor boundaries. In one embodiment, a lymph node is modeled as a capsule with moving boundaries. In one embodiment, the capsule is represented with a signed distance function d such that d>0 inside the organ, d=0 on the node boundary, and d<0 outside the organ. The gradient of the distance function d yields the normal vector n to the interior capsule surface.

Lymphoma and AML

Described herein is a lymphoma and AML model. In one embodiment, surface adhesion receptors are treated as uniformly distributed for relatively advanced lymphoma. In another embodiment where anisotropic adhesion is observed experimentally, model values comprise $\mathcal{A}_{Ig}(\varphi,0)$, $\mathcal{A}_{In}(\varphi,\theta)$, and $\mathcal{A}_B(\varphi,\theta)$, and an orientation p is introduced. p is updated by solving a balance of torque equation (similar to the balance of forces) for the angular velocity ω. x and v are maintained but cell-cell adhesion is not considered for lymphoma and AML models.

Continuum Tissue-Scale Model

Described herein is a model for 3D distribution of cell species. For modeling purpose, tissue is treated as a mixture of various cell species with individual (non-dimensionalized) densities (viable tumor cells $\rho_v$, apoptotic/necrotic cells $\rho_D$, and noncancerous host cells $\rho_H$), interstitial fluid and ECM. Cell-cell and cell-ECM mechanical interactions are modeled through a flux J which generalizes Fick's Law.

$$v_i = \alpha_{cca}\left(A_{Ig,i}\sum_{j\neq i}A_{In,j}\nabla\phi(x_i-x_j; 2r_{cca}, n_{cca}) + A_{In,i}\sum_{j\neq i}A_{Ig,j}\nabla\phi(x_i-x_j; 2r_{cca}, n_{cca})\right)^{\overbrace{}^{cell-cell\ adhesion}} + \overbrace{\alpha_{cba}A_{B,i}\nabla\phi(x_i; r_i, n_{cba})}^{cell-BM\ adhesion} - \overbrace{\alpha_{ccr}\sum_j\nabla\phi(x_i-x_j; 2r_{ccr}, n_{ccr})}^{cell-cell\ repulsion} - \overbrace{\alpha_{cbr}\nabla\phi(x_i; r_i, n_{cbr})}^{cell-BM repulsion} - F_{i,migration}$$

The rate of change in the density $\rho_i$ of cell species i is given throughout the computational domain by balancing cell advection ($\nabla \cdot (u_i \rho_i)$, where $u_i$ is the velocity of the cell species), cell-cell and cell-ECM interactions (adhesion, cell incompressibility, chemotaxis, and haptotaxis, incorporated in $J_i$), and net creation ($S_i$: proliferation minus apoptosis and necrosis), where t is time:

$$\frac{\partial \rho_i}{\partial t} + \nabla \cdot (u_i \rho_i + J_i) = S_i, \text{ for } i \in \{V, D, H\}$$

Described herein is a model for proliferation, apoptosis, and necrosis. Each species' density $\rho_i$ (V, D, or H) increases through proliferation and decreases through apoptosis and necrosis. For simplicity, it is assumed that these primarily affect tumor mass through the transport of water within the tissue and hence neglect their solid fraction. It is also assumed proliferation increases linearly with (nondimensionalized) nutrient substrate n above a threshold level $n_N$, resulting in the net creation of one cell by removing the equivalent water volume from the interstitium.

Apoptosis transfers cells from the viable tumor and host cell species to the dead cell species, where cells degrade and release their water content. In one embodiment, this models phagocytosis of apoptotic bodies by neighboring viable cells and the subsequent release of the lysed cells' water. Necrosis occurs when the nutrient substrate concentration falls below the threshold $n_N$ and ultimately releases cell's water content. In one embodiment, the resulting model is:

$$S_i = (\lambda_{M,i}(n-n_N) - \lambda_{A,i}) H[n-n_N] \rho_i - \lambda_{N,i} H[n_N - n] \rho_i, i \in \{V, H\}$$

$$S_D = H[n-n_N](\lambda_{A,V}\rho_V + \lambda_{A,H}\rho_H) + H[n_N - n](\lambda_{N,V}\rho_V + \lambda_{N,H}\rho_H) - \lambda_D \rho_D$$

where $\lambda_{M,i}$, $\lambda_{A,i}$, and $\lambda_{N,i}$ are mitosis, apoptosis, and necrosis rates, $\lambda_D$ is the cell degradation rate (varies due to the differences between apoptosis and necrosis), and H(x) is the Heaviside switch function.

Described herein is a model for cell-cell Interactions. Tumor and host cells adhere to one another but demonstrate preferential adhesion to like cells. This models: (i) the low host cell density in the stroma compared to the tumor; (ii) the observed degradation of the stroma surrounding the tumor by MMPs; and (iii) experimental evidence of cell sorting due to differential adhesion. Interface thickness depends upon the interaction of the physical forces. These effects are expressed by introducing a mechanical interaction potential function E that depends upon $\rho_V$, $\rho_N$, and $\rho_H$.

Described herein is a model for cell species velocity. The movement of cell species i is determined by the balance of proliferation-generated oncotic pressure p, cell-cell and cell-ECM adhesion, chemotaxis (due to substrate gradients), and haptotaxis (due to gradients in the ECM density f). The motion of cells and interstitial fluid through the ECM is modeled as a viscous, inertialess fluid flowing a porous medium. The variational derivative $\delta E/\delta \rho_j$ of the cell-cell interaction potential combined with the remaining contributions to J (due to pressure, haptotaxis, and chemotaxis), yields a generalized Darcy-type constitutive law for the cell motion:

$$\rho_i u_i + J_i = -k_i(\rho_i, f)\left(\nabla p - \sum_j \gamma_j \frac{\delta E}{\delta \rho_j} \nabla \rho_j\right) + \chi_n(\rho_i, f, n)\nabla n + \chi_h(\rho_i, f)\nabla f, i \in \{V, D, H\}$$

where $\gamma_j$ is the cell adhesion parameter, $\chi_n$ and $\chi_h$ are the chemotaxis and haptotaxis coefficients, and $k_i$ is the cellular mobility, which reflects the response to pressure gradients and cell-cell interactions by breaking integrin-ECM bonds and deforming the host tissue. For the host cells, it is assumed $\chi_n = \chi_h = 0$. It is assumed for simplicity that the interstitial fluid moves freely through the ECM (i.e., at a faster time scale than cells).

Described herein is a model for ECM-MMP kinetics and tissue biomechanics. The tumor cells secrete MMPs (non-dimensionalized m) that degrade the ECM (nondimensionalized f). MMPs are large macromolecules (about 100 kDa) that cannot diffuse through intact ECM, although they can diffuse through voids subsequent to tissue degradation. Cell mobility and taxis depend nonlinearly upon the ECM. Cells respond to pressure gradients by breaking integrin-ECM bonds (hence k decreases as f increases). Taxis requires that cells gain traction by forming focal integrin adhesions with the ECM. If the ECM density is too great, motile cells cannot effectively push through the ECM. Hence, k, $\chi_n$, and $\chi_h$ depend nonlinearly upon f. The model is expressed by:

$$\frac{\partial m}{\partial t} = \nabla \cdot (D_m(1-f)\nabla m) + \lambda_{m,S}\rho_V - \lambda_{m,D}m - \lambda_{m,R}mf$$

$$\frac{\partial f}{\partial t} = \lambda_{f,S}\rho_V - \lambda_{f,R}mf, \text{ and } \chi_i = \overline{\chi}_i f(1-f)$$

$$k_i = \frac{\overline{k}_i d}{c_0 + f}, i \in \{V, D, H\}$$

where $\lambda_{\cdot,S}$, $\lambda_{\cdot,D}$, and $\lambda_{\cdot,R}$ are secretion, decay, and reaction rates. In some embodiments, $D_m$ is the diffusion coefficient. In some embodiments, $c_o$ and d define the inverse relationship of $k_i$ and f. The ECM is treated as rigid (no viscoelasticity).

Described herein is model for evolution of the microvasculature. Tumor neovasculature is treated in 3D using a hybrid continuum discrete and lattice-free random walk model of tumor angiogenesis. The model generates vascular topology based on tumor angiogenic regulators, represented by a continuum variable that reflects the excess of pro-angiogenic regulators compared to inhibitory factors. In one embodiment, the effects of soluble isoforms of VEGF-A (e.g., VEGF-A165) secreted by the tumor cells are modeled. In another embodiment, transport equations are introduced to model for VEGF ($n_V$), as seen in the equation below. In one embodiment, endothelial cells near the sprout tips are modeled to proliferate and migrate by chemotaxis (in response to $n_V$) and haptotaxis. In one embodiment, leading endothelial cells are modeled according to the equation and trailing cells passively follow. In one embodiment, a vascular microarchitecture is captured via a set of rules. For example, a leading endothelial cell has a fixed probability of branching at each time step while anastomosis occurs if a leading endothelial cell crosses a vessel trailing path. In one embodiment, the age of the vessels ($a_{vessel}$, scaled by the time scale of vessel maturation) is tracked, which models the maturity of vessels as the endothelial cells tighten their junctions and become surrounded by basement membrane.

Described herein is a model for blood flow in the microvasculature. In one embodiment, the model is a lattice-free vasculature. In one embodiment, the model balance forces that determine the vessel radius including, but are not limited to, vessel blood pressure (directly tied to the flow rate), vessel wall elasticity due to VE-cadherin bonds between the endothelial cells, endothelial cell deformability, presence of the basement membrane; and external hydrostatic and mechanical pressure generated by the growing tumor. In another embodiment, these forces are balanced to derive equations for the vessel radius in all segments of the vasculature.

Described herein is a model for transport. In one embodiment, non-dimensionalized release of nutrients, n, in the vasculature is modeled that the nutrients diffuse through the tissue and are uptaken by cells during metabolism while tumor cells secrete VEGF in response to hypoxia. In one embodiment, drug, d, extravasates from the microvasculature and diffuses through the tissue. In one embodiment, on the time scale of tumor proliferation (days), the governing equations are assumed as quasi-steady. Hence:

$$0 = D_\sigma \nabla^2 \sigma + \delta_{vessel} \nu(a, u_b)(1-\sigma) - (\lambda_{\sigma,U,V}\rho_V + \lambda_{\sigma,U,H}\rho_H)$$
$$\sigma - \lambda_{\sigma,D}\sigma, \sigma \in \{n, d\}$$

$$0 = D_\sigma \nabla^2 n_V + \lambda_{n_V,S}\rho_V - \lambda_{n_V,D}n_V - \delta_{vessel}\lambda_{n_V,U}n_V$$

where $D_\sigma$ are diffusion constants, $\delta_{vessel}$ (Dirac delta function) gives the microvasculature position, v is the delivery rate (depends upon $a_{vessel}$ and $u_b$), and $\lambda_{\cdot,U,i}$, $\lambda_{\cdot,D}$, and $\lambda_{nV,S}$ are the uptake, decay, and secretion rates. In some embodiments, $u_b$ is the velocity of blood.

Described herein is a model for lymph gland and spleen geometry. In one embodiment, the model is a capsule with a 2D surface Γ that is stretched by the growing tumor, with membrane normal velocity proportional to the proliferation-generated pressure gradient. The tissue surrounding the organ is assumed to deform sufficiently to accommodate expansion. If P is the mechanical pressure generated by the proliferating tumor, then the motion of Γ is modeled by Inside the lymph node or spleen:

$$-\nabla \cdot (k\nabla P) = \frac{\sum_i \rho_i S_i}{\sum_i \rho_i}$$

On the lymph node or spleen boundary:

$$P = -\gamma\kappa \text{ and } v = -k\nabla P$$

where k is the mobility given above, γ is the membrane elasticity (may vary with position), and κ is the mean curvature.

Integrated Multi-Scale Analysis of Tumor and Host Response to Therapy

In one aspect, multiscale measurements of the host response to cancer and its therapy are performed. In one embodiment, host-level measurements records host immune response. In another embodiment, host-level measurements records cytokines that mediate intercellular communication. In one embodiment, systems-level measurements of the dynamics of the host immune response are obtained using a self-assembling high density protein microarray platform, and serum cytokine levels are monitored using a highly sensitive magneto nano protein chip technology. In one embodiment, time points and treatment conditions with tumor-level measurements is performed to acquire a dataset that tracks the progression of the tumor and the host. In one embodiment, this coordinated tumor/host (TH) dataset is used to develop a computational TH model of the functional interactions between tumor and host. In one embodiment, a TH model includes low dimensional subset of tumor/host variables needed to predict the future TH state based on its past condition. In one embodiment, a TH model is integrated with the molecular-cellular tumor model to produce a comprehensive MSCS. In one embodiment, the MSCS is used to predict the temporal evolution of the disease at the cell, tumor and host levels in response to specific molecular interventions. In one embodiment, the MSCS predictions are fed back to all modules to experimentally validate model predictions. In another embodiment, in silico prediction is followed up by in vivo mouse models using either a different tumor strain or RNAi to interfere with the appropriate tumor pathways that correspond to the phenotypic perturbations performed in silico. In one embodiment, genes are modified for validation purpose including, but are not limited to Arf, Tsc2, Akt, MMP, VEGF, and HIF-1α.

In one embodiment, a lymph flow model uses Darcy-type flow through the sinuses and porous cortex with sources and outflow in the afferent and efferent lymph vessels. The model is useful for investigating (i) how lymph flow affects drug delivery, (ii) how cells exit the lymph node during metastasis, and (iii) how incoming tumor cells lodge in the lymph node. In one embodiment, an AML combines an MSCS with literature models of radiotherapy. In one embodiment, an MSCS incorporates models of hematopoietic stem cells and their progeny to predict their impact on AML and its therapy response.

In one embodiment, a lymphatic metastasis model system is built by coupling whole-organ tumor model to a compartmental model of the lymphatics. In such system, each lymph node or the spleen is a compartment that uses an MSCS. In one embodiment, each compartment is coupled with estimated/simulated tumor cell transit times through the lymph ducts.

INCORPORATION BY REFERENCE

All publications, patents, and patent applications mentioned in this specification are herein incorporated by reference to the same extent as if each individual publication, patent, or patent application was specifically and individually indicated to be incorporated by reference.

EXAMPLES

Example 1

Immunostaing for Ki-67 of Ductal Carcinoma Cells

Figure 2A:
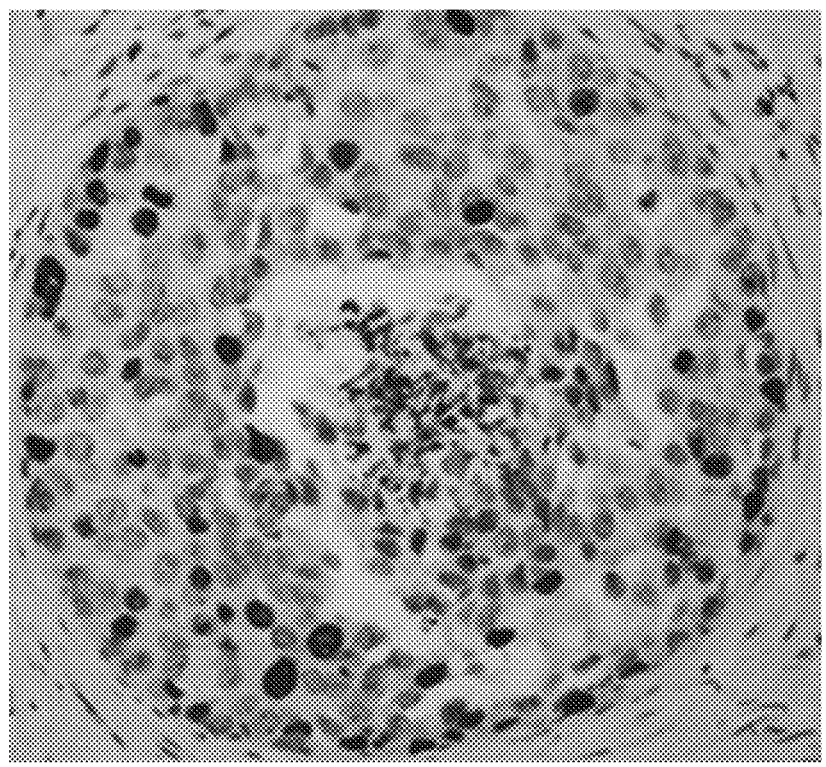
FIG. 2A and FIG. 2B illustrates Ki-67 immunohistochemistry for proliferating cells in breast cancer (top), with a Histogram of number of proliferating cells vs. distance from the duct wall, showing a clear correlation (bottom).
Figure 2B:
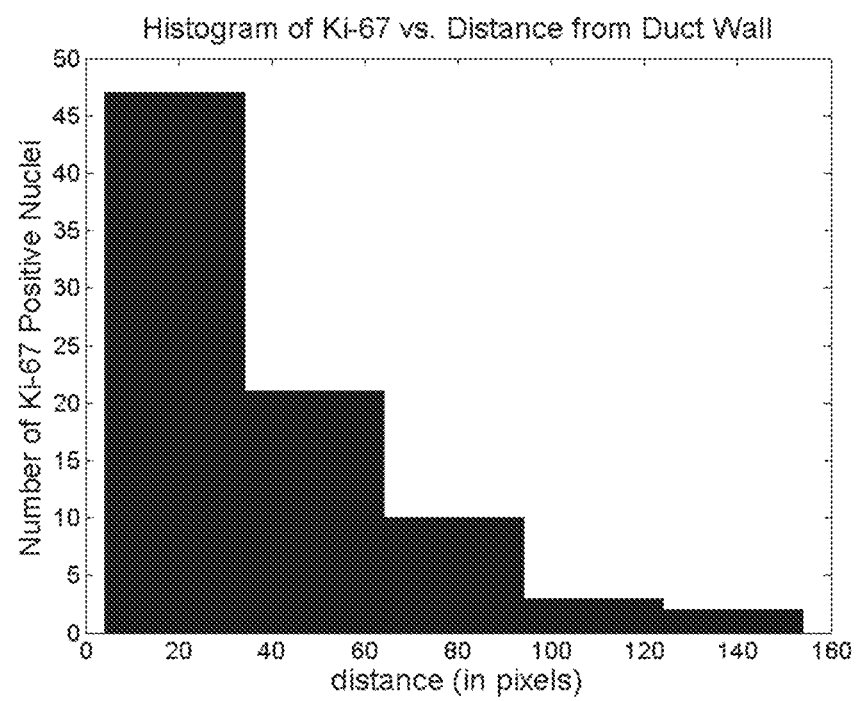

Samples of ductal carcinoma in situ in the breast from full mastectomies were immunostained for Ki-67 (a nuclear protein marker for cell proliferation) in ex vivo (FIG. 2). Proliferation occurred most frequently along the duct wall where nutrients and growth factors are most common. Much rarer proliferation was observed along the perinecrotic boundary towards the duct center where oxygen and nutrient levels were lowest (FIG. 2, top). To further quantify this, the distance between the duct wall and the Ki-67 positive nuclei were measured and plotted this as a histogram (FIG. 2, bottom). As seen in the graph, an excellent correlation between distance from the duct wall and the proliferation activity was observed, indicating a functional relationship between a microenvironmental quantity (e.g., oxygen), an intracellular protein (Ki-67), and cell phenotype (proliferation).

Figure 3:
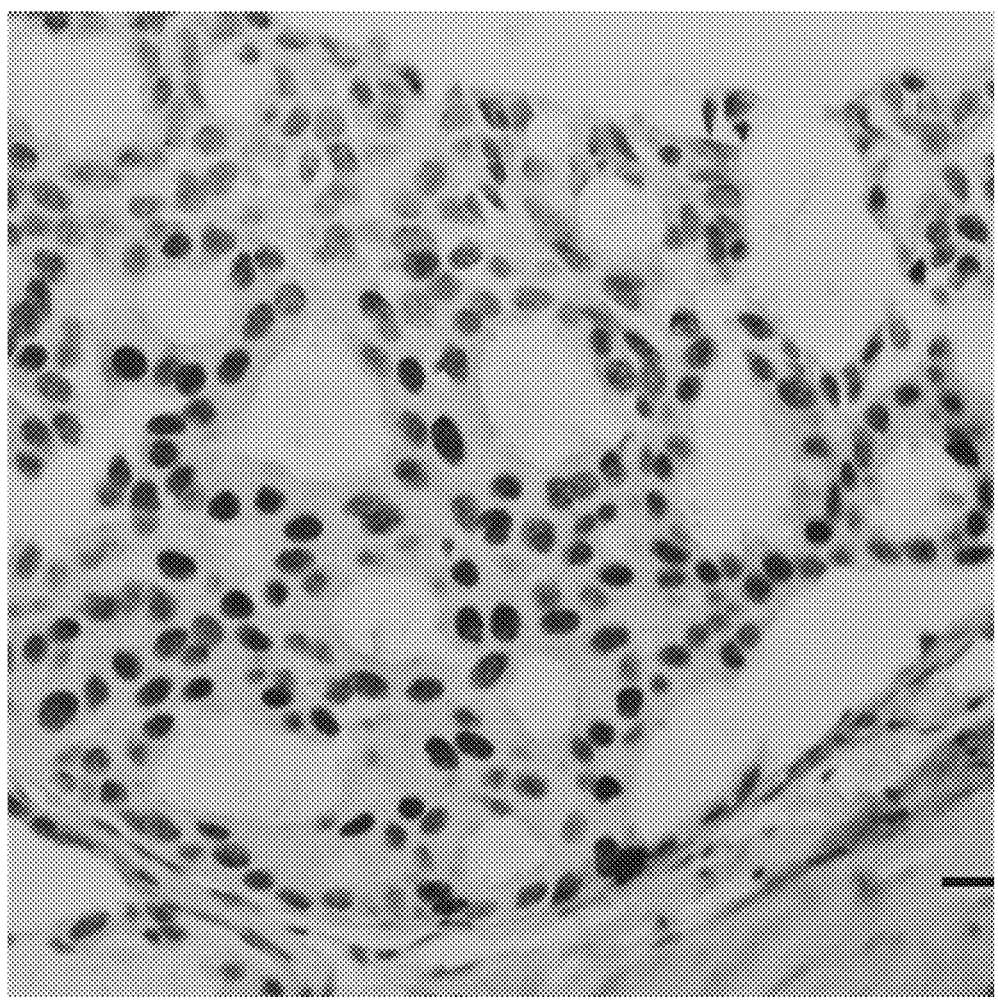
FIG. 3 illustrates nonlinear gradient in internalized estrogen receptor.

A similar correlation has been observed between internalized (i.e., activated) estrogen receptor (ER) and distance from the duct wall (FIG. 3). FIG. 3 shows nonlinear gradient in internalized estrogen receptor (ER) (dark red) with nearly all cells demonstrating ER activity near the duct wall (bottom side of photo). A shallow gradient in activity (little change in stain intensity) followed by a sharp drop-off in activity near the perinecrotic tumor boundary is evident in the photograph (top side of photo). All cells near the duct wall show an intense staining for activated ER near the duct wall, followed by a near-imperceptible gradient in staining intensity with increasing distance from the wall until a sharp-drop-off at a nearly uniform distance from the perinecrotic boundary. These together suggest sufficiently-mechanistic signaling models can demonstrate nonlinear relationships between microenvironmental variables (e.g., oxygen and growth factors), internal proteins (e.g., Ki-67), and cell phenotype (in this case, proliferation).

Example 2

Structural Model of an MSCS

RP1 module collects data on p53 activation in response to diverse forms of cellular stress to mediate a variety of anti-proliferative processes. Stress data include molecular events or extracellular stimuli associated with DNA damage, hypoxia, aberrant oncogene expression to promote cell-cycle checkpoints, DNA repair, cellular senescence, or apoptosis. Presence of anticancer agents activating p53 is recorded. Presence of agents promoting apoptosis or senescence is also recorded. Loss of p53 function is checked. RP2 module collects data on treatment with drug in p53 null system. The module checks if the loss causes decreased perturbation of pathways associated with cell death relative to ARF null. RP3 module analyzes treatment with drug in p53 null system to see if it has normal growth character. The module checks ARF level to see if it is increased. If increased, the module checks if there is correlation between increase apoptosis and increased drug access, or other variables such as differences in the distribution nutrient. RP3 module checks if ARF is non-functional or if its expression is heterogeneous within the population of cells. RP4, based on the data fed by RP1, RP2, and RP3, makes prediction that, for example, ARF-mediated increase of apoptosis leads to more shedding and larger immune response. Based on the formulated prediction, perturbations introduced to the virtual system illicit responses revealing changes in the host immune response to tumor/stroma associated antigens.

Example 3

Structural Model of an MSCS

First, a cell model is built based on known information on p53 pathways. Protein binding assays on p53 pathway components and proteins known or suspected to be proximal to the pathway are conducted to collect up-to-date data on the cellular model. Differences in phosphorylation states measured by phospho-flow from those expected in the p53 pathway are added to the model. Updated network/pathway components are introduced to the Inferelator and its predictions are validated by comparing predicted dynamics to be measured. The model's phenotypic predictions, such as growth rate and pathway activates, are incorporated as input to the tumor model. At tumor-level model, any differences in measured tumor growth, vasculature, necrosis, and heterogeneity are used to update the tumor model. Updated tumor model parameters (such as change in growth rate, physical and spatial characteristics of the cell, invasiveness and mobility, etc.) are extracted and are used to make new tumor-level predictions. Unexplained phenotypes may require new model mechanisms to be introduced. Lack of predictive ability may require increased level of detail beyond the anticipated reduced state space cell model to include, for example, more individual expression measurements. At host level model, the host model's parameters are updated based on the cell and tumor models to provide updated predictions of host response. Antigens and cytokine release predicted by the model based on the cell and tumor models' status which are not realized in the experimental system require explanation based on novel host mechanisms and/or an update to the upstream models. These modifications include refinements of antigen and cytokine co-expression models. Predicted host responses are fed back to the cell level model as updated microenvironmental conditions to refine cell level predictions. Prediction successes and failures at this stage are used to improved accuracy of prediction.

Example 4

Integrating Prior Information, Data and Public Data to Train Modules Prior to Network Reconstruction Algorithm cMonkey was designed with the goal of identifying co-regulated gene groupings. cMonkey is used for "pre-clustering" genes prior to learning regulatory influences. This reduces the dimensionality and computational cost of the downstream analysis and also aids in biological interpretation of the results. The integrated biclustering approach used in cMonkey groups genes and conditions into biclusters on the basis of 1) coherence in expression and proteomics data across subsets of experimental conditions, 2) co-occurrence of regulatory motifs in the regulatory regions of bicluster members and 3) the presence of highly connected sub-graphs in metabolic and functional association networks Example 4

Method for Network Dynamical Network Inference: the Inferelator

Algorithm for regulatory network inference is called Inferelator. The level of a gene (expression, protein, modification or interaction) or the mean level of a group of coregulated genes, y, is assumed to be influenced by the level of N other factors in the system: $X=\{x_1, x_2, x_N\}$. The relation between response y and predictors X is given by the kinetic equation:

$$\tau \frac{dy}{dt} = -y + g(\beta \cdot Z)$$

Figure 8:
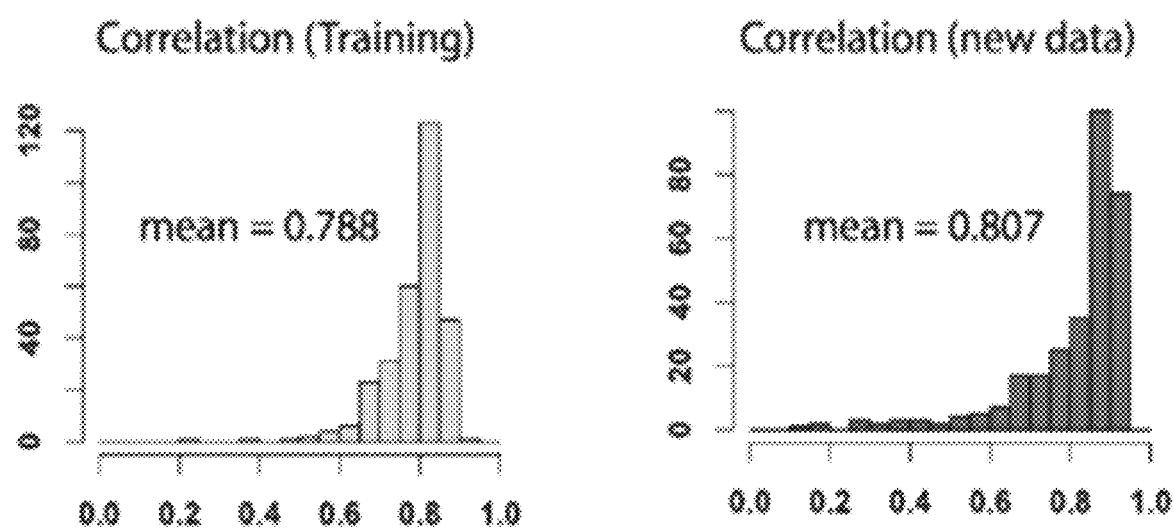
FIG. 8 illustrates an Infrelator algorithm's predictive performance on 130 conditions.

An encoding of interactions is used by allowing functions in Z to be either 1) the identity function of a single variable or 2) the minimum of two variables. This encoding results in a linear interpolation of (linearly smoothed approximation to) the desired Boolean function. This and other interactions (OR, XOR, AND), as well as interactions involving more than two components, can be fitted by this encoding. This scheme for encoding interactions is expected to capture many of the interactions between predictors necessary for modeling realistic regulatory networks in a readily interpretable form. Removal of the capability to model interactions in this way reduces the predictive power of the Inferelator on the newly collected validation data set. The function g, called the nonlinearity or link function, takes the form of a sigmoidal or logistic activation function. This form has been used successfully in models of developmental biology and is compatible with L1-shrinkage methods for enforcing model parsimony. This model encompasses essential elements required to describe gene transcription, such as control by specific transcriptional activators (or repressors), activation kinetics, and transcript decay, while at the same time facilitating access to computationally efficient methods for searching among an astronomically large number of possible regulators and regulator combinations. The network model is tested over additional measurements, collected after initial publication of an Inferelator-constructed model (FIG. 8), and validated by using ChIP-chip assay. The method has been applied to the learning of human regulatory networks which control TLR-5-mediated stimulation of macrophages of networks that mediate mouse T-cell differentiation, and of several other microbial networks. In FIG. 8, the Pearson correlation between predicted expression and measured expression over 300 biclusters for both training data (left) and 130 newly collected microarray experiments (right, blue) are shown. Each bicluster has on average 2.5 connections in the network. This level of parsimony, combined with the performance on newly collected data suggests the model is truly predictive of regulatory dynamics. Removing explicit treatment of dynamics significantly reduces predictive power over the conditions.

Example 5

Proteomics Discovery of Markers of Response to Therapy

Cell-surface and secretory proteomes in response to therapeutic intervention with gefitinib is measured. In addition to identifying proteins that changed in response to therapeutic intervention, a panel of protein markers with utility for predicting and/or monitoring response to HER-kinase axis targeted therapies is identified. The panel is identified by comparing protein expression patterns across lines known to have differential response to therapeutic intervention. Proteomic analysis of cell lines is performed by SILAC, a metabolic isotope-labeling technique, which enables quantitative analysis of protein changes in response to gefitinib treatment in three sub-proteomes. Several proteomic techniques are used to profile each of the cell compartments: a) intact protein fractionation followed by shotgun tandem mass spectrometry (MS/MS) to probe the intracellular proteome; b) biotin-capture-based cell-surface protein extraction, followed by intact protein fractionation and shotgun MS/MS to identify and quantitate constituents of the cell-surface proteome; and c) solid-phase extraction of glycoprotein (SPEG) profiling for the enrichment and subsequent study of the secretome. Xenograft tissue and serum studies used acrylamide labeling for quantitation.

Profiling of the A431-sensitive cancer cell line identifies 3,707 intracellular proteins, 1,276 cell surface proteins and 879 secreted proteins (peptide/protein prophet>0.9). 400 proteins show a statistically significant change in abundance following geftinib treatment. Immunologic methods are used to validate the protein level changes predicted by SILAC in vitro. Each protein with abundance changes is validated in vitro. Immunologic tests are performed on in vivo (xenograft) tissue and plasma samples. Ten potential cell-surface biomarkers show changes in abundance in response to therapy both in vitro and in vivo. An additional seven proteins show changes in the secretome and serum.

Example 6

Protein Arrays and Application to Protein-Interactions

Figure 9A:
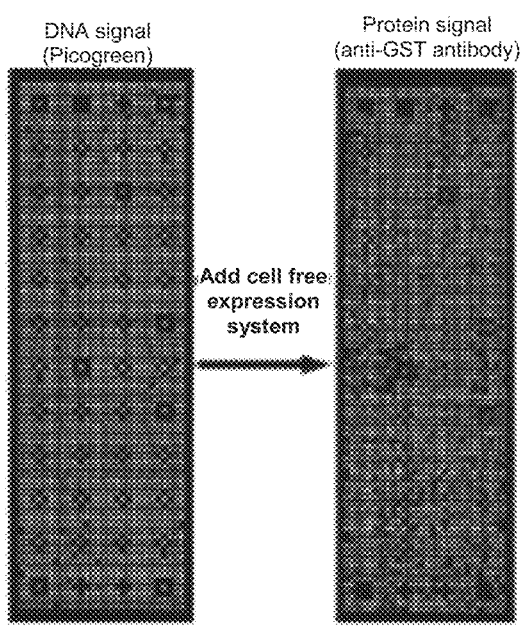
FIG. 9A, FIG. 9B, and FIG. 9C illustrate Protein display on NAPPA.
Figure 9B:
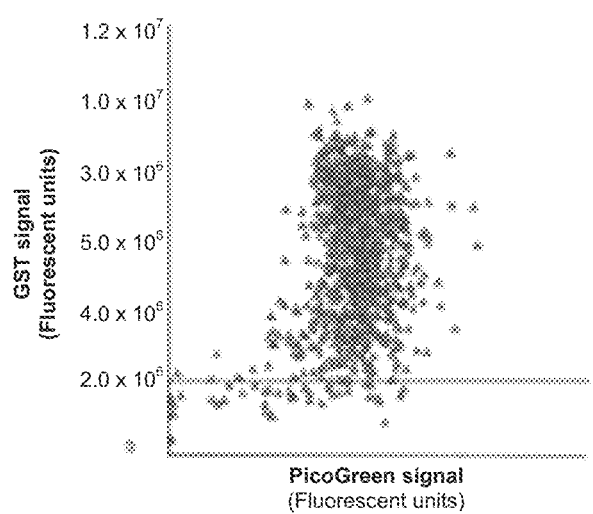
Figure 9C:
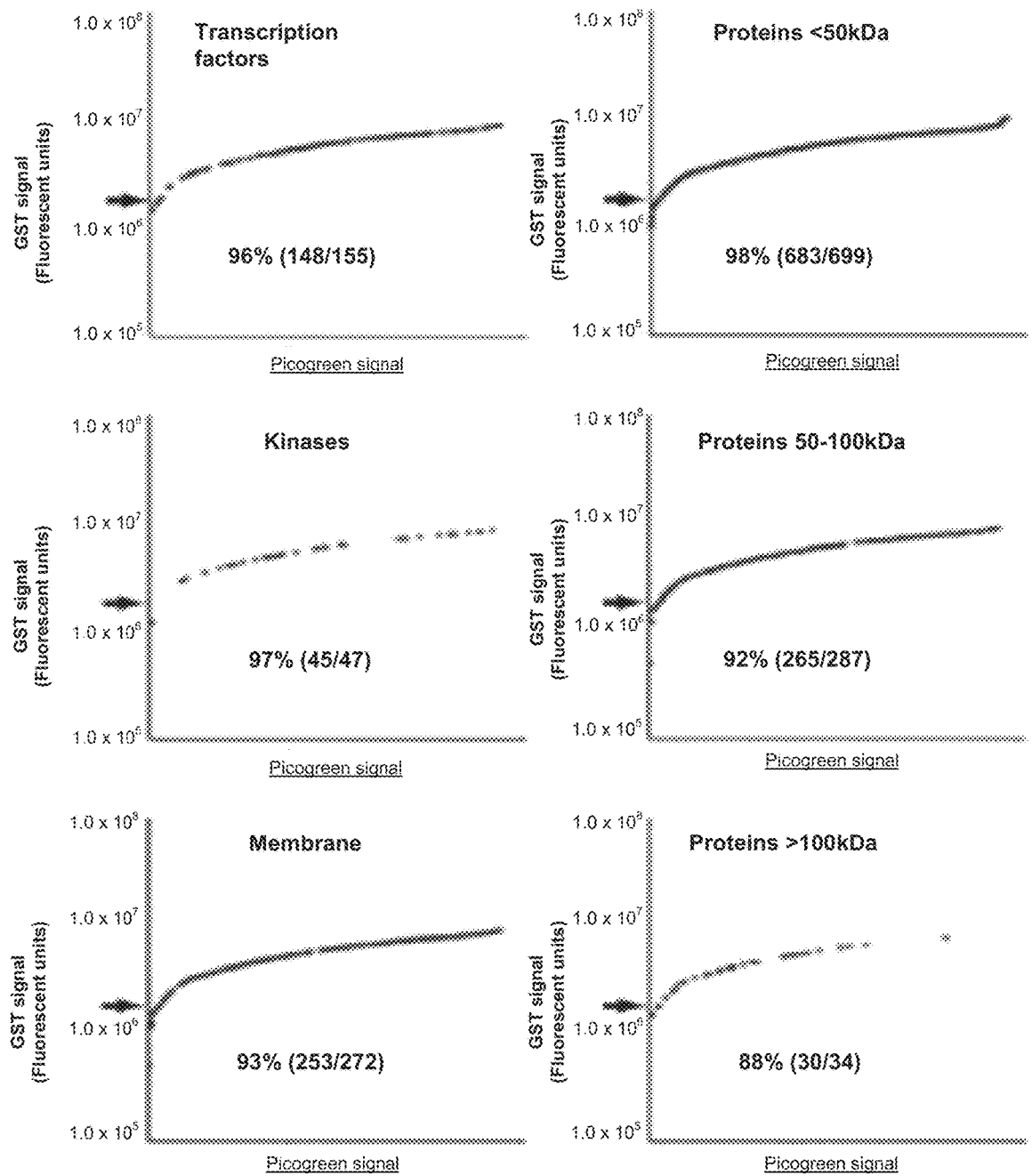

Nucleic Acid Protein Programmable Array (NAPPA) is used to collect protein data. NAPPA enables the display of freshly produced proteins from cloned copies of genes by in situ expression. Thus experiments are set up rapidly without requiring the cumbersome expression, purification and immobilization of proteins required by standard methods. NAPPA can monitor signals for over 10,000 human proteins per array. NAPPA has a 95% success rate for protein display. A high and consistent yield of proteins is displayed on the arrays with no protein type biases—both soluble and membrane proteins display efficiently (FIG. 9). FIG. 9 shows (A) Picogreen staining shows consistency of DNA printing and anti-GST antibody detects the common epitope tag on all proteins showing consistency of protein display; (B) plot of the two signals in (a) shows that all proteins are displayed at levels within a single log; (C) protein yields organized by protein type and size showing percent success. The black arrow indicates 3 SD above the background signal. More than 50 fmoles of protein is expressed per spot (~1000 fold more protein than conventional protein spotted arrays). Finally, coefficients of variation are low with average CVs under 10%. NAPPA is used for the high-throughput measurement of protein-protein interactions. To map the binary interactions, each protein is used as a query to probe a pair of duplicate arrays to generate a 30×30 protein interaction matrix. Of the gold standard interactions that had been demonstrated biochemically using purified proteins, 17 of 20 (85%) was detected with a significantly lower false negative rate than other interaction assays.

Example 7

Development of Methods for Real-Time Label-Free Detection by SPR

Figure 10:
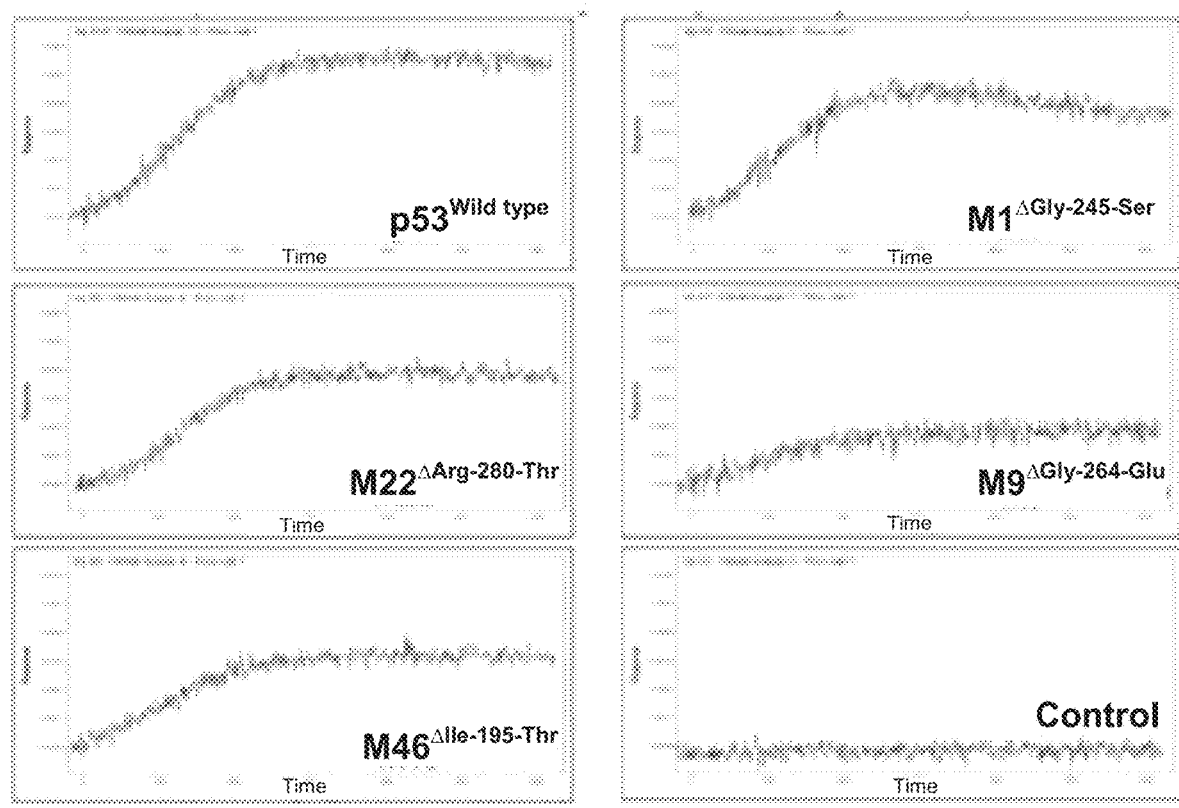
FIG. 10 illustrates Mutant p53 MDM2 binding.

To evaluate whether on-chip protein synthesis system would produce sufficient protein for SPR detection, three genes are printed with tag on the C terminus with GST (Jun, Fos, p53) in triplicate, as well as a series of controls. The proteins were expressed using NAPPA protocol and then placed on the SPR device. A fluidics system is used to inject antibody directed at p53; binding was immediately detected at all three of the p53 spots but not at the other protein spots nor at any of the negative controls spots. Similarly, antibodies directed at Fos and Jun detected the relevant spots, indicating the protein produced by coupling NAPPA to the SPR device yields sufficient protein for detection. To determine if this configuration of NAPPA and SPR can detect protein interactions in a clinically relevant manner, a series of clinically defined point mutations in the p53 protein are tested for binding to MDM2, a known interactor. As shown in FIG. 10, purified MDM2 binds to the different p53 mutants and to wild-type p53 with different kinetics and affinities. From these data, on rates ($k_{on}$), off rates ($k_{off}$) and affinity constants ($K_D$) were computed. These proteins on the arrays can be phosphorylated or otherwise modified with post-translational modifications to determine the effects of such modifications on protein interactions.

Example 8

Signaling in Human Lymphoma Cells Stratifies Patient Outcomes

A signaling network profiles was used to identify subsets of cells within samples of live, primary follicular lymphoma (FL) obtained prior to treatment. Altered B cell receptor (BCR) signaling was shown to distinguish between cancerous and non-malignant B cells within FL samples. In some cases, the patient's sample at diagnosis was composed of at least three cancer cell subsets distinguished by differences in response to BCR stimulation. In addition, the T cells infiltrating these samples failed to phosphorylate Stat5 when stimulated with IL-7. Patients with this signaling profile had a significantly worse response to initial chemotherapy ($p<0.002$) and lower overall survival ($p<0.02$) than patients whose at-diagnosis sample was composed of a more uniform lymphoma B cell population and T cells with intact signaling responses.

Figure 12A:
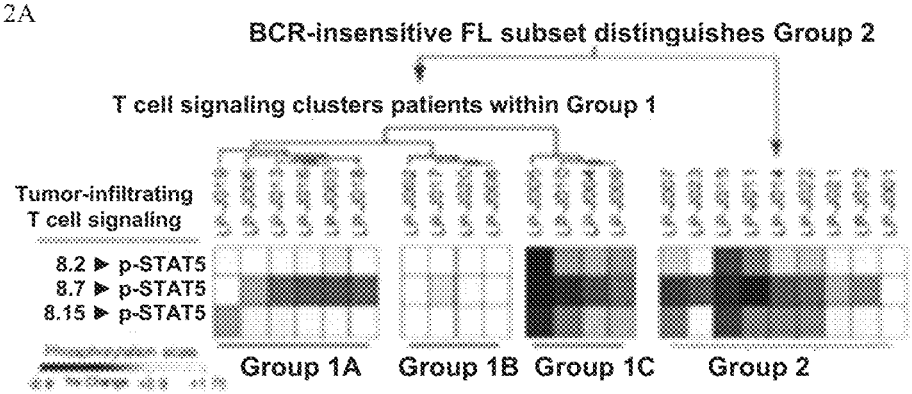
FIG. 12A, FIG. 12B, and FIG. 12C illustrate Tumor-infiltrating T cell signaling stratifies survival of patients lacking a BCR-insensitive lymphoma cell subset.
Figure 12B:
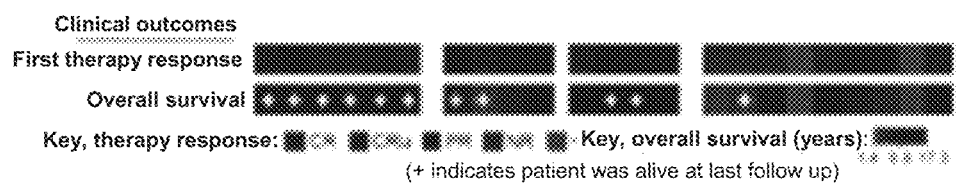
Figure 12C:
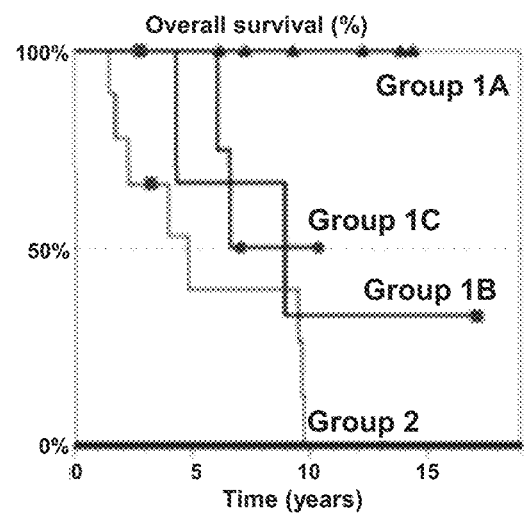

Analysis of p-SFK, p-Stat5, and p-Syk identified two subsets of FL cells in patients (Subset 1 and Subset 2) which expressed different amounts of Bcl-2 and CD20c. Flow cytometry analysis of BCR signaling in FL tumor cell subsets is shown for patients representing these two contrasting signaling profiles in FIG. 11. FIG. 11 shows (A) Histogram plots of phosphorylated SFKs, Stat5, Syk, Erk1/2 and Akt are shown in FL tumor B cells stimulated by BCR crosslinking plus H2O2 for 4, 15, or 45 minutes or left unstimulated. FIG. 11(B) is flow cytometry heatmap plots showing signaling in FL tumor samples left unstimulated or stimulated for 4 minutes by BCR crosslinking plus H2O2. The z-axis heatmap color compares p-SFK, p-Stat5, p-Syk, p-Erk1/2, or p-Akt signaling with Bcl-2 expression (y-axis) and CD20c expression (x-axis). FIG. 11(C) is modeling of FL cell subsets based on BCR signaling in the presence of H2O2. The cells with a significant response to 45 minutes of BCR crosslinking plus H2O2 were identified on cont plots of Bcl-2 vs. CD20c (red). In cells from patient LP-J013, signals appeared to be uniform across the population, with the majority of the signaling occurring in the central core. In patient LP-J007, a population with only moderate Bcl-2 over-expression was detectable within the tumor specimen (Subset 2). Following BCR crosslinking of LP-J007, Subset 2 was the only population that activated p-SFK, p-Stat5, and p-Syk. Tumor-infiltrating T cell signaling was then used to further cluster patients. Three major clusters were defined by IL-7, IL-2, and IL-15 mediated STAT5 phosphorylation. Clustering in Group 1 (patients where no BCR-insensitive subset was observed) is shown in FIG. 12A. FIG. 12A shows Clustering of T cell responses stratify patient outcomes to reveal both survival and time to remission. Heatmap color indicates the fold increase in p-STAT5 following IL-2, IL-7, and IL-15 stimulation. A central outcome was the identification of a subpopulation of lymphoma cells whose presence at the time of diagnosis is associated with poor patient clinical outcomes: failure to respond to the first round of therapy and shorter overall survival (FIG. 12B, Correlation of group to outcome from poor (red) to the median (black) to good (blue)). In order to find this lymphoma cell subset, flow cytometry was used to measure signaling in individual lymphoma B cells within primary samples of patients' tumors. This single cell view was critical, in that it revealed the heterogeneity within the lymphoma samples and exposed a population of cells that existed only in the aggressive cases of follicular lymphoma. Results showed the description of outcome-stratifying contributory signaling in the tumor infiltrating T cells, providing that both lymphoma cells and immune T cells contain complementary signaling profiles linked to clinical outcome (FIG. 12C, Overall survival of FL patient groups defined by tumor-infiltrating T cell signaling combined with BCR signaling heterogeneity). These results indicate therapeutic modulation of the immune system should be combined with therapies that directly target aggressive subpopulations of cancer cells.

Example 9

Collection of Mass Spectrometry Datasets

Cells are grown in DMEM media (Invitrogen) containing 1% of dialyzed fetal bovine serum (FBS) (Invitrogen) and either 12C or 13C lysine for 7 passages according the standard SILAC protocol. The same batch of cells is used for mRNA analysis, extraction of cell surface proteins, analysis of conditioned media, and analysis for whole cell lysate proteins & phosphoprotein. Cells are harvested at each of 5 time points (spanning 1 minute to 48 hrs) selected for diversity of therapeutic/perturbant impact on cell dynamics. For MS experiments, heavy and light populations are mixed with a reference time 0 state.

To isolate cell surface proteins from the treated and control lines, about $2\times10^8$ cells are biotinylated in a culture plate after PBS rinsing with 10 ml of 1 mg/ml of Sulfo-NHS-SS-BIOTIN (Pierce™) in PBS supplemented with 1 mM Mg/Ca at 4° C. for 20 min. Following quenching, protein extraction is then performed by cell disruption by sonication followed by centrifugation. Biotinylated proteins are chromatographically isolated by affinity chromatography into an OG solution.

Solid-phase extraction of secreted glycoproteins is performed. Briefly, secreted proteins are oxidized with 10 mM sodium periodate in oxidation buffer for 1 h at room temperature in darkness. The proteins are desalted and resuspended and coupled to hydrazide resin overnight. N-linked glycopeptides are released by addition of 1 U/μl PNGase F post digestion. Cell surface, conditioned media and total extract are fractionated into 20 fractions by reversed-phase chromatography, using 500 μg, 1 mg and 1 mg of total protein, respectively. All the cell extracts are reduced and alkylated with iodoacetamide prior to chromatography. Separation is performed in a POROS R1/10 column (4.6×50 mm, Applied Biosystems™) at 2.7 ml/min using a linear gradient of 10 to 80% of organic solvent over 30 minutes.

Example 10

Protein Identification and Quantification by LC-MS/MS

Protein digestion and identification by LC-MS/MS are performed. Briefly, fractions are individually analyzed by LC-MS/MS in a LTQ-FTICR or LTQ-Orbitrap mass spectrometer (Thermo-Finnigan™) with a 90-minute linear gradient. Acquired data are automatically processed using the Computational Proteomics Analysis System (CPAS). Tandem mass spectra are compared to version 3.13 of the human IPI database. A fixed modification of 6.020129 mass units is added to lysine residues for database searching to account for incorporation of the heavy lysine isotope. All identifications with a PeptideProphet™ probability greater than 0.9 are submitted to ProteinProphet and the subsequent protein identifications filtered at a 1% error rate. Spectral counting method is used to estimate protein enrichment for each compartment. A quantitative approach that employs differential labeling of proteins in culture with lysine isotopes (heavy or light) is employed. Quantitative information is extracted using a script designated "Q3." Only peptides with a minimum of 0.90 PeptideProphet score are considered in the analysis. Statistical significance of the protein quantitative information is obtained for those proteins with multiple peptides quantified; a p-value for the mean log-ratio, which has mean zero under the null hypothesis, are calculated using one-sample t-test.

Example 11

Preparing a Series of Known Clinical Mutations in the Genes for Relevant Proteins of Interest Bioinformatics tools were used to identify known clinical variations for the target protein(s). Mutants were generated using a combination of targeted DNA primers with the intended mutation, in vitro DNA polymerization and methylation sensitive bacteria. All of mutants were verified by DNA sequencing. All of the ORFs were introduced into Gateway Entry vector, pDONR221. These clones, totaling about 40,000 clones, were in that vector and it is compatible with NAPPA protein expression vectors.

Example 12

Transferring of Mutants into the Protein Array

As each collection of mutant ORFs is produced, the ORFs are transferred using standard LR Cloning into pANT7GST-K coil vector. This vector supports the in vitro transcription/translation (IVTT) of proteins using reticulocyte lysate. The vector appends a carboxyl terminal tag to the end of the ORF that includes both a GST moiety and the K coil tag. The K coil tag supports capture of the protein via a printed K-coil tag on the array surface and the 26 kDa GST moiety holds the protein slightly off the array surface, making it more accessible to interaction and provides a convenient means for confirming protein expression and capture (with an anti-GST antibody). DNA for the target genes are produced using standard large-scale DNA preparative methods. The DNA is then combined with amide-activated K coil peptide and printed onto thiol activated gold-coated glass slides. Key controls include peptide alone, DNA alone, water and relevant purified proteins. Each gene is printed in duplicate or triplicate on the arrays. The arrays is printed with Genetix Qarray™ printer at Rh 60% at room temperature, dried after printing and stored in Lock-n-Lock boxes at room temperature with a silica packet. In addition to the gold-coated slides, a small number of standard glass slides is printed with the same chemistry for quality control.

At the time of the experiment, slides are rehydrated in PBS and blocked with a polyanion blocker (sulfate dextran) to neutralize the charges. Proteins are then expressed using IVTT mix (TNT kit, Promega™) according to published methods. After washing, the slides are mounted on the ProteomicProcessor™ for further analysis. The printed slides are tested with Picogreen™ for DNA binding to confirm consistent printing. And similarly, printed glass slides are expressed and tested with anti-GST antibody followed by fluorescently tagged anti-mouse IgG to confirm protein expression. Finally, one of the gold-coated printed slides is expressed, placed on the ProteomicProcessor™ and probed with anti-GST and/or anti-bodies directed at the target protein.

Example 13

Building Epigenetic Somatic Cell Clock and Investigating Tumor Ancestry

Epigenetic somatic cell clock is produced from normal glands from human colon, small intestines, endometrium, hair follicles, and hematopoietic cells (neutrophils, B-lymphocytes, T-lymphocytes) from different aged individuals. Briefly, each clock was produced by following the procedures outlined in FIG. 19: tissue is disaggregated into single crypt (clones of about 2,000 cells), bisulfite treated, and then amplified by PCR. The PCR products are cloned into bacteria, and individual clones are sequenced. The somatic cell ancestries inferred from methylation patterns in these cell types were generally consistent with their biology. For example, human colon crypts exhibited age related increases in clock methylation (the clocks, like most CpG rich non-repetitive regions of the human genome are initially unmethylated at birth), different crypts from the same colon had different methylation patterns (random drift), and crypt diversities were consistent with the stem cell niches that are thought to maintain mammalian epithelium.

Figure 20A:
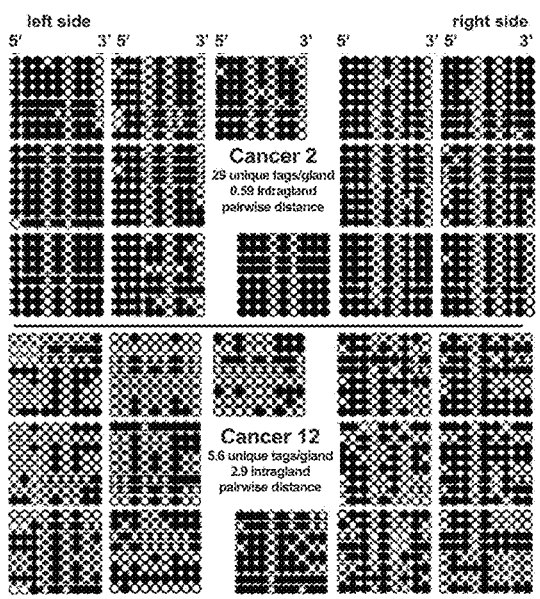
FIGS. 20A and 20B illustrate sample data from 12 colorectal cancers.
Figure 20B:
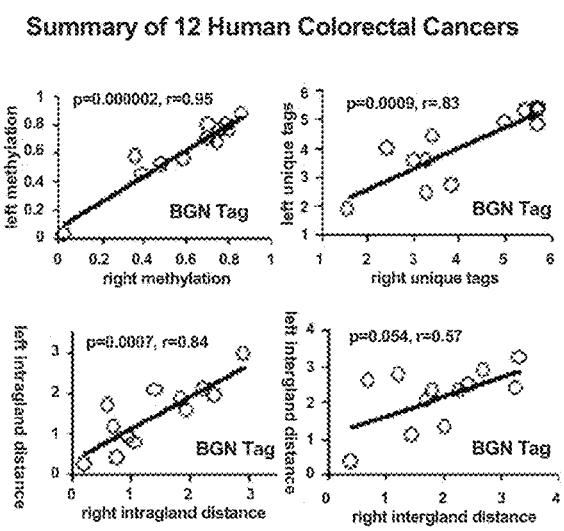

A total of 12 human colorectal cancer samples were analyzed by sampling different parts of the same tumor by the strategy outlined in FIG. 16. Sample data are illustrated in FIG. 20. On the left is data for the BGN clock (9 CpG sites arranged horizontally in a 5' to 3' order). Each of the two cancer had 14 cancer glands sampled (7 from the left side, and 7 from the right side). From each gland, eight epialleles were sequenced after bisulfite treatment, PCR, and cloning the PCR products into bacteria. Each cancer gland can be characterized by: 1) percent methylation (average of methylated sites); 2) diversity or the average pairwise distances between epiallele comparisons within a gland (intragland distances); 3) diversity by the number of unique patterns found after sampling eight epialleles.

Figure 21:
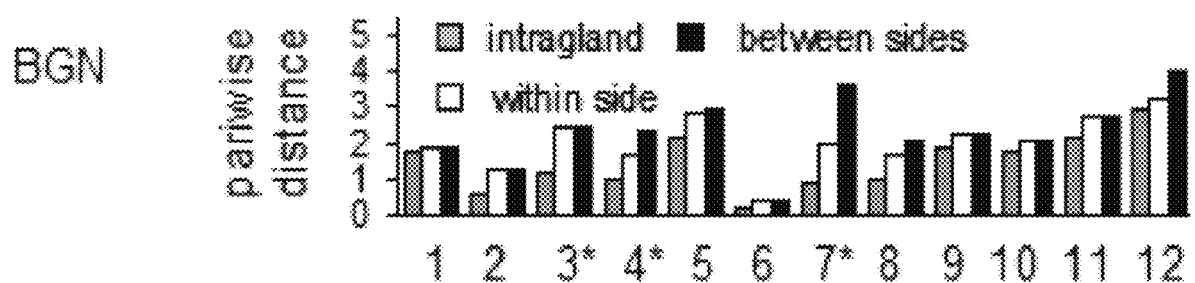
FIG. 21 illustrates measurement of pair-wise distance between glands either from the same side or intergland distances.

Pairwise distances between glands either from the same side or between sides (intergland distances) are measured and shown in FIG. 21. Data were collected from fresh cancer glands that were isolated at random from each cancer side. Expected order of average diversity was found: epialleles from opposite cancer sides are more different than within a side, and smallest within a cancer gland. Human colorectal cancers appeared to be flat clonal expansions. The right and left sides of the same cancer have similar average epiallele methylation and diversity, indicating that the ancestries of different parts of the same cancer are similar (FIG. 8, right panels).

Figure 22:
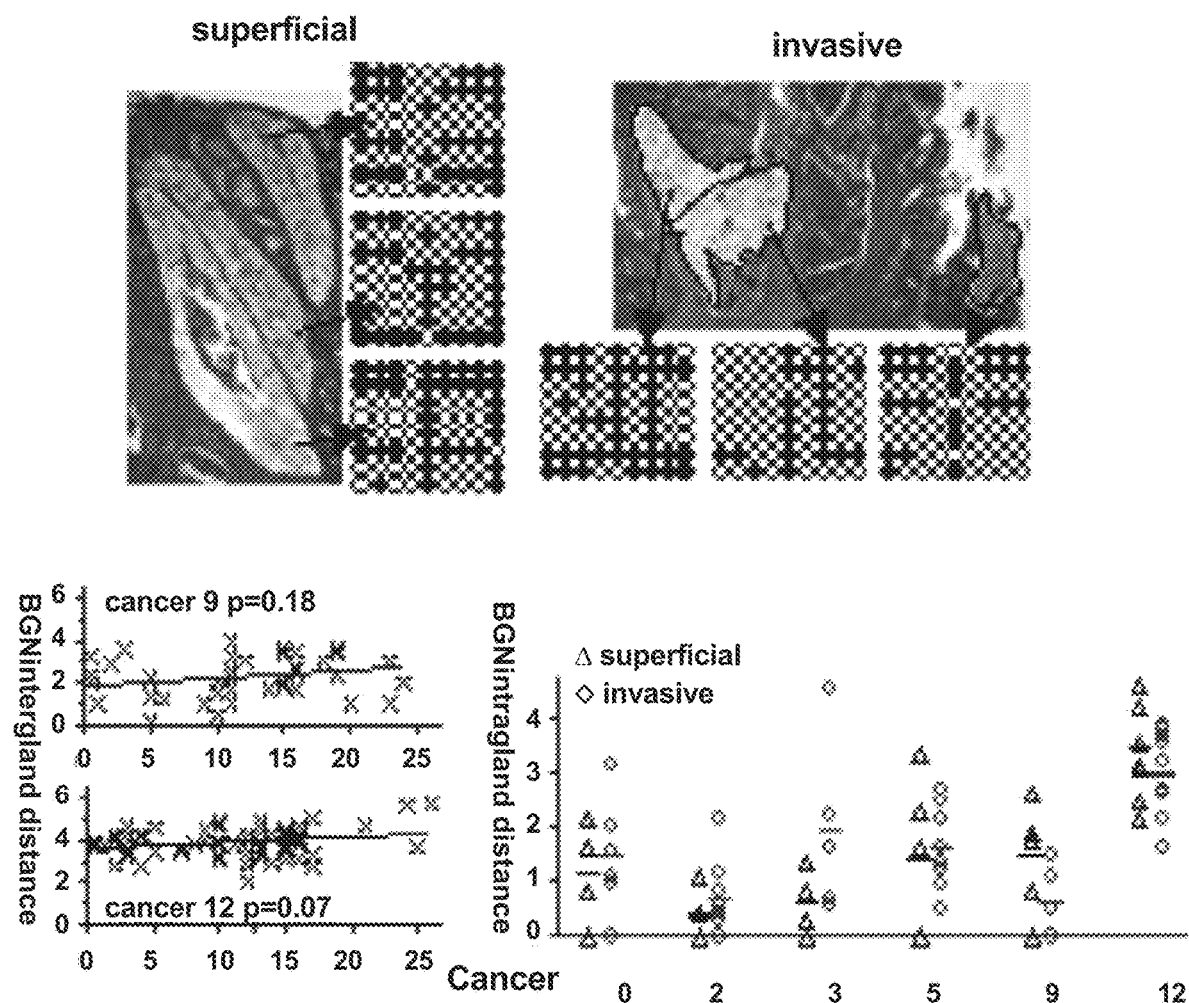
FIG. 22 illustrates measurement of physical distances among different parts of the same cancer using laser capture microscopy.

Using laser capture microscopy (LCM), sample space was specifically captured by microdissecting cancer glands from different parts of the same cancer. The actual physical distances between glands and their phenotypes (superficial or invasive) were measured (FIG. 22). FIG. 22 shows the eight epialleles sampled from each cancer gland region after LCM. The first graph in FIG. 22 shows pairwise distances between glands are similar regardless if glands are sampled nearby or many centimeters away, albeit there is a slight trend for greater intergland distances as physical distances increases. The second graph in FIG. 22 shows that there are no significant differences in intragland diversity whether cancer glands are isolated from superficial regions or from the invasive border. The data are consistent with the idea that human colorectal cancers are flat clonal expansions because the amount of diversity is similar throughout the tumor, consistent with a rapid growth scenario immediately after transformation. This observation simplifies simulations, because for example, a single set of rules can be applied to every gland. Accordingly, all of the 12 epialleles per cancer measured in FIG. 20 can coalesce back in time to a single pattern.

Example 14

Figure 23:
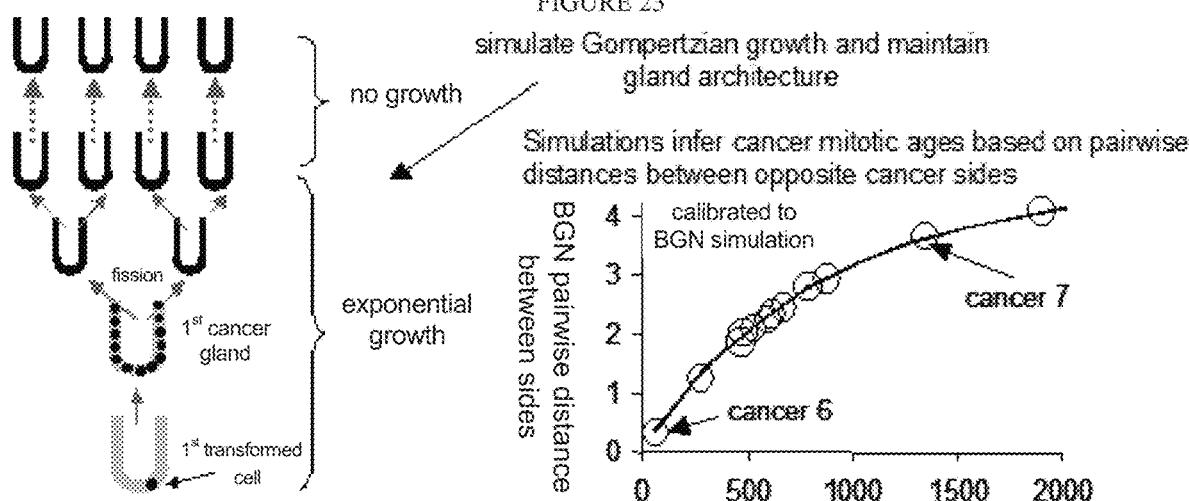
FIG. 23 illustrates forward simulation of human tumor growth using the Gompertzian, or initially exponential assumption.

Forward Simulation of Human Tumor Growth Using the Gompertzian, or Initially Exponential Assumption In FIG. 23, a forward simulation for human tumor growth was performed. Simulation was started with the first transformed cell, which expands to fill a cancer gland. This cancer gland splits into two glands. This process is repeated for about 32 doublings to get a visible tumor containing four billion cells. Subsequently growth stops and cell division is balanced by cell death. Instead of simulating an entire billion cell tumor, a few glands were simulated. FIG. 23 graph illustrates that one can infer the mitotic age of each cancer based on average pairwise distances between epialleles from opposite cancer sides. (Mitotic age is not a linear function of pairwise distance because backward changes also may occur.)

Figure 24:
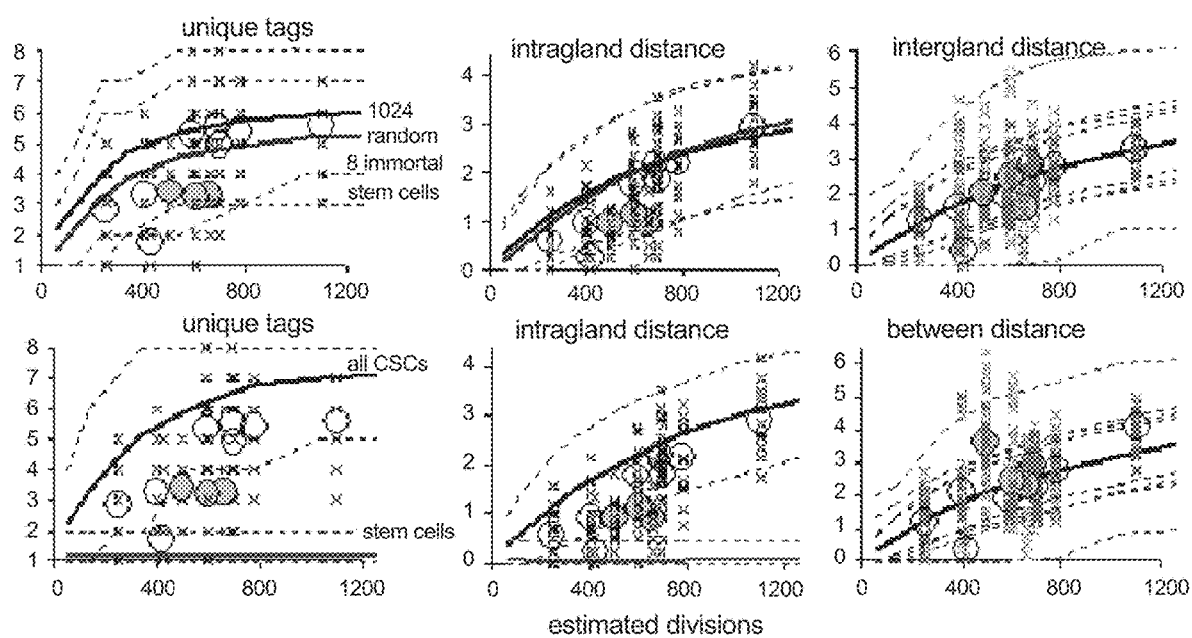
FIG. 24 illustrates simulation results for matching various cancer stem cell scenarios with experimental data.

Epiallele distances within glands compared to between opposite cancer sides can be used to infer numbers of long-lived cancer lineages (cancer stem cells (CSCs)) that maintain individual cancer glands. As a first approximation, glands that are almost as diverse as their tumors contain many CSCs whereas glands with very little diversity contain much fewer CSCs. One can simulate which CSC scenarios match the experimental data (FIG. 24). Experimental data are represented by circles (average values) and x's (individual cancer gland values). Simulations are represented by solid lines (average values), and dotted lines (95% simulation intervals for gland values). The extreme scenarios (one CSC per gland (pink lines), or all cancer cells are CSC (blue lines)) are less consistent with the data compared to intermediate numbers of CSCs per gland. The likely outcomes of the simulations are present in Table 7.

TABLE 7

Colorectal Cancers: p values for right versus left cancer comparisons

| Cancer | Age | Size | Stage | MSI+ | estimated mitotic age | CSCs/gland * |
|---|---|---|---|---|---|---|
| 1 | 65 | 3 | A | N | 590 | 16, 1024 |
| 2 | 79 | 4 | A | N | 250 | 8, 1024 |
| 3 | 46 | 4.5 | B | Y | 600 | 4, 64 |
| 4 | 50 | 4.5 | A | Y | 660 | 4, 128 |
| 5 | 53 | 4.5 | C | N | 690 | 8, 1024 |
| 6 | 51 | 5.5 | C | N | 420 | 8, 512 |
| 7 | 43 | 5.5 | C | Y | 1130 | 4, 256 |
| 8 | 98 | 6 | B | N | 400 | 4, 256 |
| 9 | 85 | 7.5 | D | N | 700 | 16, 1024 |
| 10 | 61 | 7.5 | C | N | 380 | 8, 128 |
| 11 | 83 | 8 | B | N | 780 | 8, 1024 |
| 12 | 44 | 9 | C | N | 1100 | 8, 1024 |

* estimated numbers of CSCs per gland with either deterministic divisions (always asymmetric, lower number) or stochastic survival (asymmetric or symmetric divisions, higher number)

Example 15

Methylation Pattern Heterogeneity

Figure 26A:
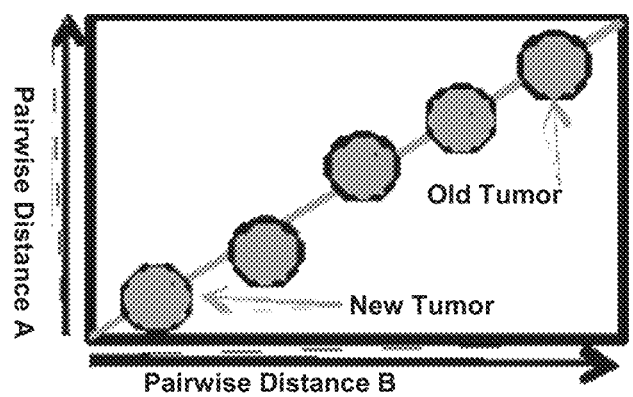
FIG. 26A and FIG. 26B illustrate correlative or non-correlative relations of clock-like behaviors between two paired loci.
Figure 26B:
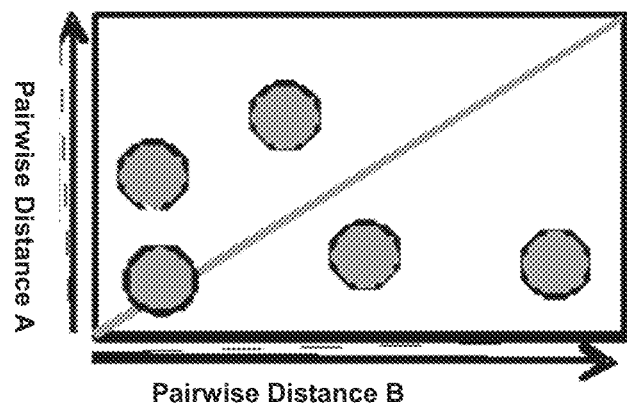

To examine a wide variety of CpG rich regions, regions appear to function as reliable somatic cell clocks are empirically determined. Pairwise distances between epialleles at different genomic regions are correlated in different tumors (FIG. 26). In FIG. 26, clock-like behaviors for locus A and B are plotted. FIG. 26A shows equally polymorphic correlations in different tumors because clock locus variation is a function of mitotic age. FIG. 26B shows no correlation between the loci in different tumors, indicating that either locus A or B does not have clock-like properties. Bulk tumor DNA is isolated from leukemia cells purified by flow cytometry. The DNA is sheared into 200 to 500 bp fragments, sequencer linkers are added, and enriched for CpG rich regions using a microarray from NimbleGen™ that contains all annotated human CpG islands (28,226 different loci, probe length: 50-75mer, with 385,000 probes per array). Bisulfite treatment is performed and the target regions of enriched DNA are sequenced.

With microarray enrichment, about 70% of the sequences are from the targeted regions. A single Solexa™ sequencing run generates about 80 to 100 million different ~75 by reads. Thus, two human AML specimens are analyzed per Solexa run and obtain on average about 990 to 1,200 sequences per CpG rich loci per tumor. This represents about 74,000 to 90,000 base per CpG rich locus. These sequence reads are aligned and pairwise differences are calculated and compared between loci. A total of six human AML specimens are analyzed with Solexa sequencing during the first two years of the proposal.

The high throughput of Solexa sequencing allows for the screening of all human CpG islands for clock-like behaviors. Through screening, CpG rich regions in which methylation patterns randomly drift with genome replication are identified. The top 20 candidate clock loci identified are further analyzed in multiple human leukemias to test for mitotic age concordance. The top clock loci are defined as loci whose average pairwise methylation pattern differences are similar within a leukemia specimen yet differ between AML specimens. In this way a set reliable somatic cell clock loci that can be used to reconstruct the ancestry of any human tumor are developed.

Example 16

Copy Number Variation at High Resolution Using a Dense-SNP Array

DNA copy number variation (CNV) is characterized with a SNP array. CNVs (amplifications or deletions) tend to occur in important tumor suppressor genes or oncogenes and therefore provide information on selective or driver mutation evolution. These clonal CNVs are identified using the Illumina one million SNP Array™ (a SNP about every 3,000 bases). A patient's normal germline (measured from his normal lymphoid cells) is compared with the tumor genome for leukemia specific loss of heterozygosity or amplification at adjacent polymorphic loci.

CNVs are useful to follow and characterize relapse after therapy because the genome of the relapsed clone often has different CNVs (usually one or two additional changes or even the loss of a CNV). Some of the chromosome breakpoint alterations are characterized by screening with inverse PCR and sequencing. PCR primers are designed such that the presence or absence of a specific CNV at past or future time points can be determined with high sensitivity.

Example 17

Developing Suitable Somatic Cell Molecular Clocks

Data from methylation, CNVs, or other experiments are used to develop somatic cell molecular clocks by identifying different genomic regions that appear to record similar ancestries. Coalescent is used to trace methylation patterns back to the first transformed cell. For more formal analysis of cancer ancestry, more data such as epialleles from multiple clock loci are used. By doing so, the mitotic age of each leukemia is estimated that the greater the methylation pattern variation, the greater the mitotic age of the leukemia. Because replication errors are stochastic and may vary along a chromosome, multiple (about 20) genomic regions are used to estimate mitotic age.

To specifically analyze clock loci by bisulfite sequencing, PCR primers of the clock-like regions are produced. The clock regions are about 100 to 200 base pairs in length and contain from eight to 20 CpG sites. Human leukemias tend to be near diploid so each leukemia cell has two epialleles per genome. PCR is designed to include common polymorphic SNPs so that maternal and paternal alleles are distinguished in appropriate heterozygotes.

From each leukemia specimen, bisulfite sequencing is performed for about 40 epialleles at the 20 informative clock epiallele regions. With bisulfite treatment of the AML DNA, PCR of each clock locus is performed, followed by cloning of the PCR products into bacteria, and conventional DNA sequencing of 40 different clones from each clock locus.

Example 18

Figure 27:
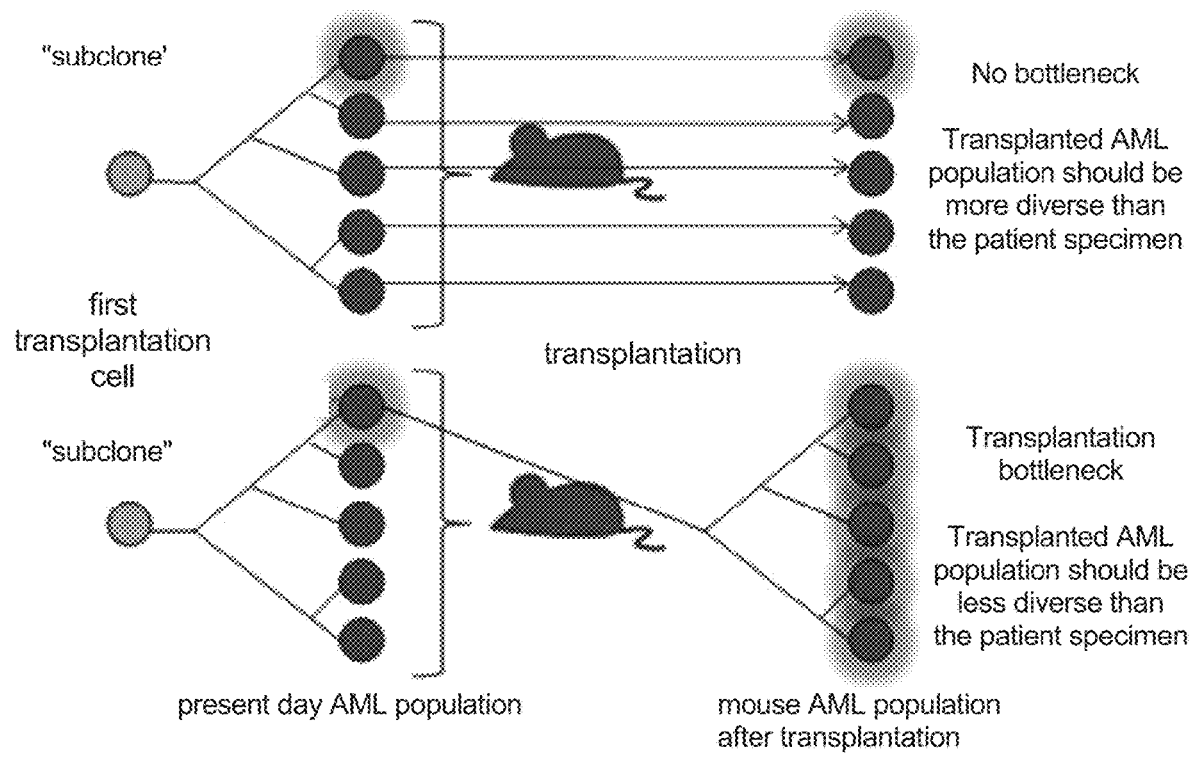
FIG. 27 illustrates modes of transplantation.

Sequential Clock Measurements on Serial Cultures of the Leukemia in NOD/SCID Mice Somatic cell molecular clocks are experimentally validated by examining a leukemia population at serial time points during culture in mice. Human AML specimens are serially propagated in immunocompromised mice. Transplantation is performed after sublethal irradiation by injecting leukemic cells (i.v. or i.p.). Transplantation scenarios are diagramed in FIG. 27. After engraftment, the human AML cells comprising a few percent to the majority of hematopoietic cells in the recipient mice, serving as a starting point of observation. After two to four months, the human AML cells are purified by flow cytometry and then reinjected several more times to serially propagate the leukemia, allowing serial examination of the human AML population through time.

To control for any bottleneck effect imposed by a particular animal model, AML cells are marked with a retroviral GFP vector. Retroviral integration of the engrafted AML cells is monitored with Southern blot analysis For example, the presence of a single retroviral integration indicates a severe bottleneck (i.e., most engrafted AML cells originate from a single clone) whereas a polyclonal Southern blot (many different retroviral integration sites) indicates a minimal bottleneck. These observations are reflected to the methylation clocks in a corresponding manner. To check whether or not the CNV genotype is maintained after passage in the NOD/SCID mice, high density SNP mapping is used.

Example 19

Dynamic Tumor Imaging and Quantitation of Imaging Data

Figure 29:
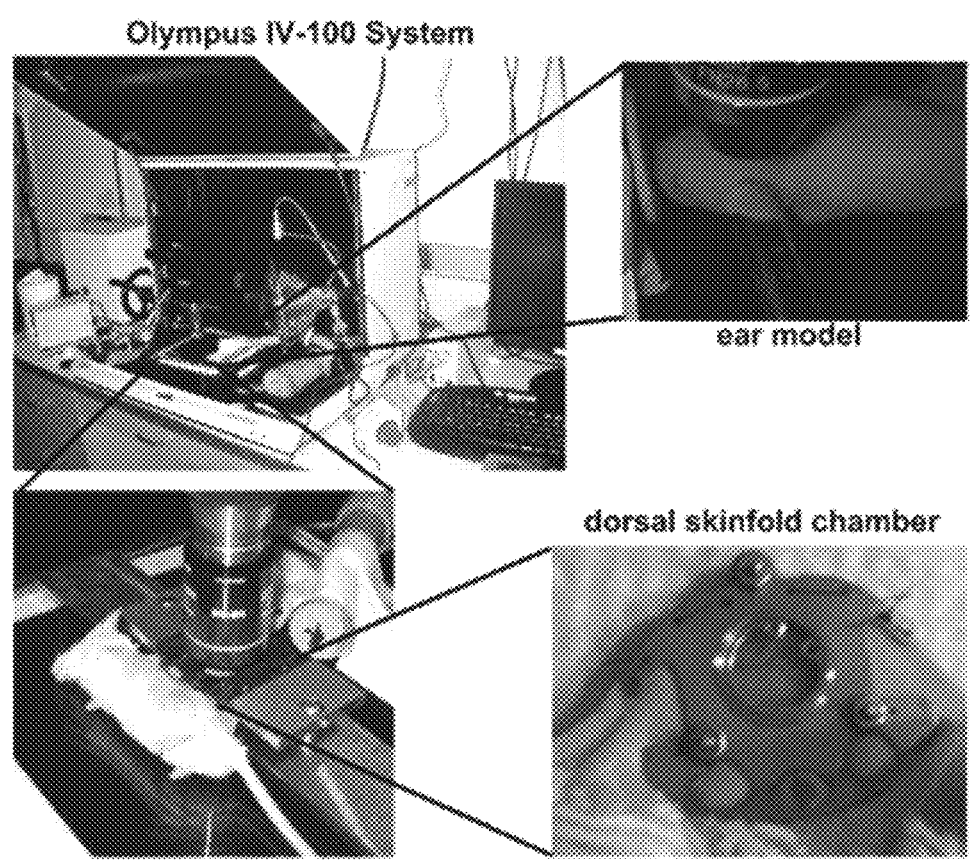
FIG. 29 illustrates a system to visualize nanoparticles in tumor.

Nanoparticles were used to directly image a tumor within the mouse ear, the dorsal skinfold chamber (DSC), and the cranial window chamber. Using an Olympus IV-100 instrument, specific binding of nanoparticles to tumor neovasculature, extravasation of nanoparticles (related to blood vessel permeability), and binding of targeted nanoparticles to tumor cells were observed. Olympus IV-100 instrument setting was as follows: up to four simultaneous input lasers of 488 nm, 561 nm, 633 nm, and 748 nm and three simultaneous output channels with an assortment of filters were employed. In addition to nanoparticles, larger particles (microbubbles) were used to image the tumor. For example, quantum dots (qdots) were conjugated to RGD, a peptide sequence recognizing an integrin over-expressed on tumor blood vessels and on some tumor cell membranes. RGD-qdot binding to tumor neovasculature was quantified in an SKOV-3 based tumor in the nude mouse ear (FIG. 29). FIG. 29 upper left panel shows Olympus IV-100 system used to visualize nanoparticles in tumor. Upper right shows the ear model, grown in nude mice, is displayed while imaging a nude mouse. Lower right panel shows DSC showing visible blood vessels in the window. Lower left panel shows mouse with a DSC held still with custom-designed stage and imaged with the IV-100.

Qdots are injected via tail vein, visualizing the influx in the tumor circulation. RGD-qdots bound to tumor neovasculature in a statistically significant manner compared to controls. Controls were as follows: RAD peptide on qdots, bare qdots, block of integrins on the endothelial cell surface using Cy5.5-RGD prior to RGD-qdot administration, and injection of RGD-qdots into a non-tumorigenic mouse.

Figure 30:
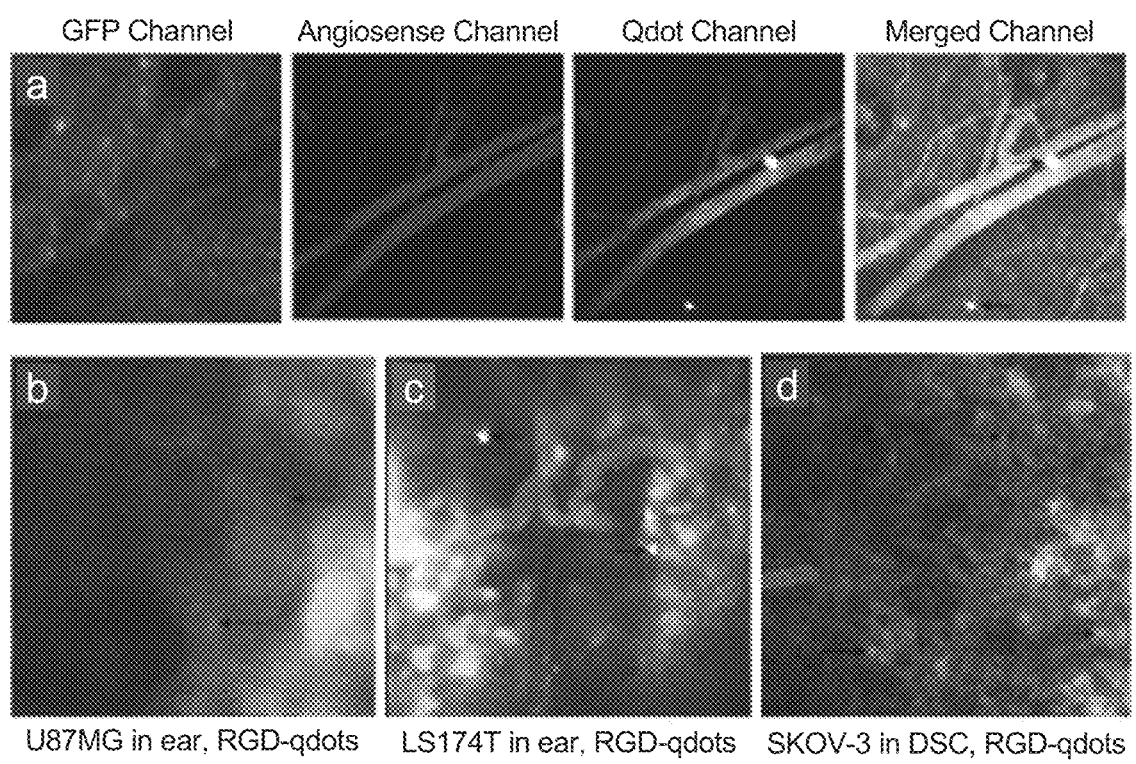
FIG. 30 illustrates Displays the direct visualization of RGD-qdot aggregates binding to tumor vasculature in mouse ear and the dorsal window chamber.

As shown in FIG. 30, aggregates rather than individual qdots bound to neovasculature. Aggregation was also observed in two other tumor models U87MG and LS174T. FIG. 30 displays the direct visualization of RGD-qdot aggregates binding to tumor vasculature in mouse ear and the dorsal window chamber. Panel (a) displays the three simultaneous output channels, including the GFP channel (left), angiosense channel (second from left), near-infrared Qdot channel (second to right), and the merged image of tumor and blood vessels (right) as labeled. Individual tumor cells were visible on the left GFP image (circular green spots). The near-infrared channel shows qdots still in vessels, and the binding events are visible by reference to the bright white areas, which are indicated by black arrows in the merged image. (b-d) show only the merged images of various tumors with colors as in (a). Panel (b) shows U87MG tumor in mouse ear with 2 binding events. Panel (c) shows tumor with particularly tortuous blood vessels in mouse ear with 2 binding events. Panel (d) shows SKOV-3 tumor in a dorsal window chamber with 4 binding events.

Figure 31:
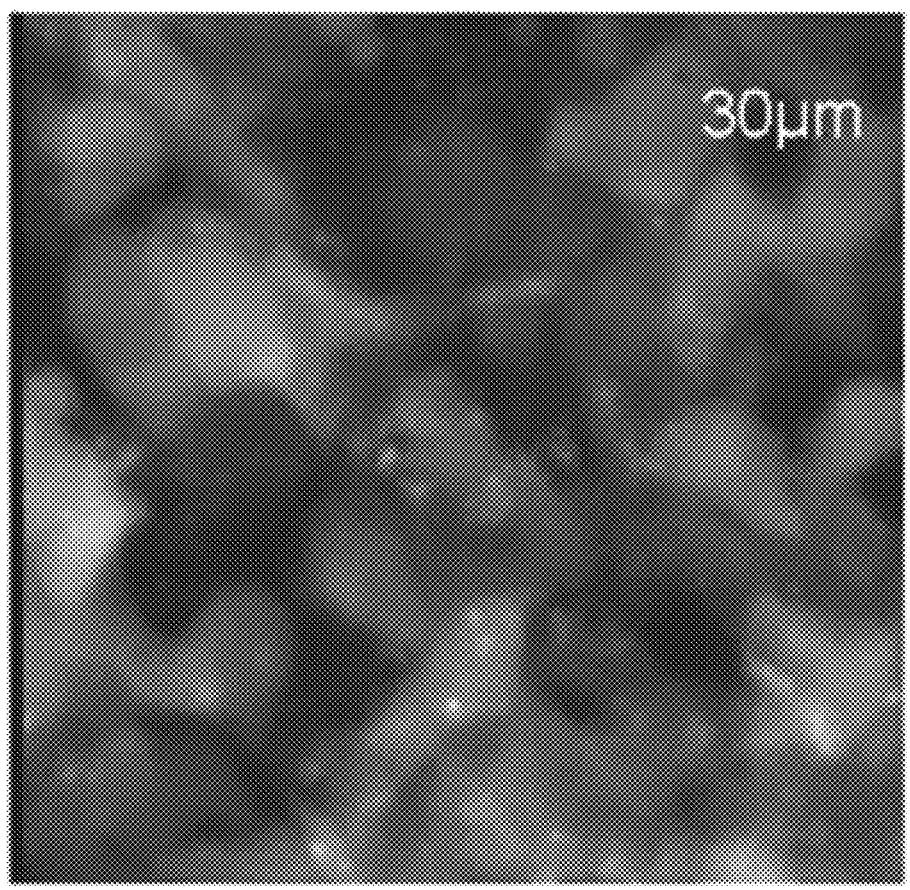
FIG. 31 illustrates shows an area of tumor interstitium in which RGD-SWNTs are bound to individual tumor cells 12 days after SWNT injection.

RGD and Cy5.5 were conjugated to single-walled carbon nanotubes (SWNTs). RGD-SWNTs were observed and quantified binding to tumor neovasculature, extravasating from tumor blood vessels, and eventually binding to tumor cells over a period of weeks to months. FIG. 31 shows an area of tumor interstitium in which RGD-SWNTs are bound to individual tumor cells 12 days after SWNT injection. Individual tumor cells were clearly visible and their dynamics were visualized over a period of hours. In FIG. 31, a merged image was captured 12 days after injection of RGD-SWNTs in the tumor of a live mouse. Single tumor cells (green) were visible with SWNTs bound to them (gray). RGD-SWNTs have clearly bound to and been taken up by individual tumor cells in the living mouse 12 days post-injection.

Example 20

Model Predictivity

One of the models described herein was used to conduct detailed parameter studies to investigate the links between cell adhesion, tissue invasion, and microenvironmental substrate gradients. It was found that across broad ranges of phenotypic parameters such as proliferation, apoptosis, and adhesion, microenvironmental substrate gradients could increase tissue invasion by promoting tumor fragmentation. Anti-invasive and vascular normalizing therapies could reverse this effect. These findings were confirmed in vitro after calibrating to human glioblastoma multiforme.

Figure 33:
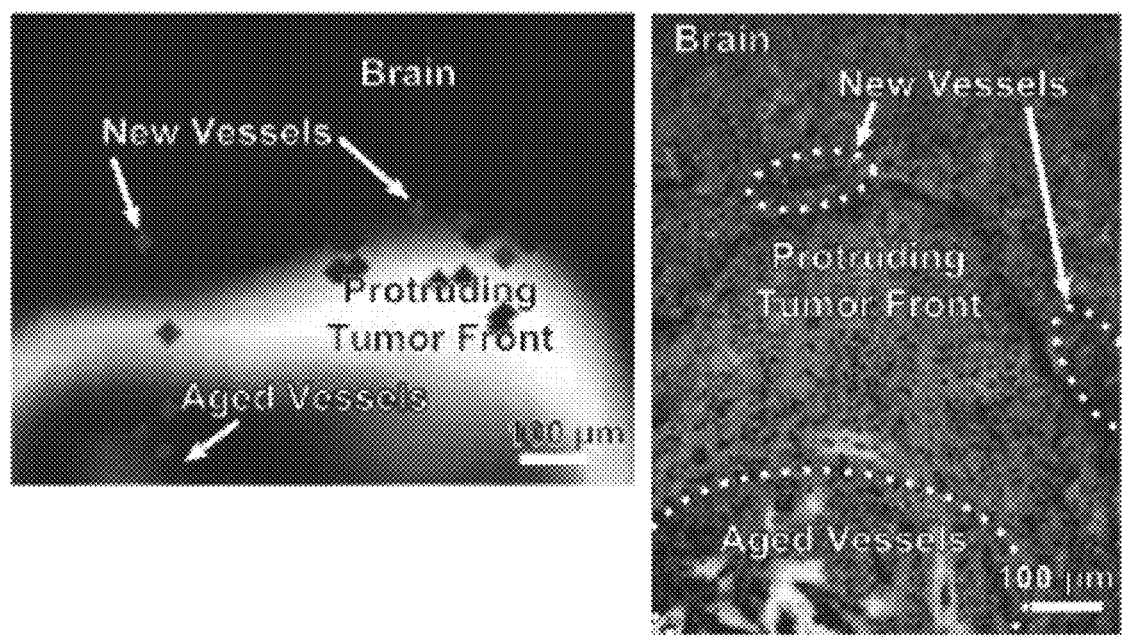
FIG. 33 illustrates model predictivity.

After further model training with human glioma, parameter values that were consistent with typical experimental observations in the literature were obtained and used in the model to predict 3D brain tumor evolution in vivo. When the model's virtual histopathology was compared to in vivo data, excellent agreement was observed in spatiotemporal evolution of the tumor morphology, size and shape of invasive tumor protrusions, and the distribution of new (FIG. 33). FIG. 33 shows comparing virtual histopathology slices from 3D simulator (left) with in vivo histopathology (right) after calibration to in vitro brain cancer data. The calibrated model successfully predicted independent 3D histopathologic details, demonstrating the predictive capability of rigorously-calibrated mechanistic models.

Figure 34:
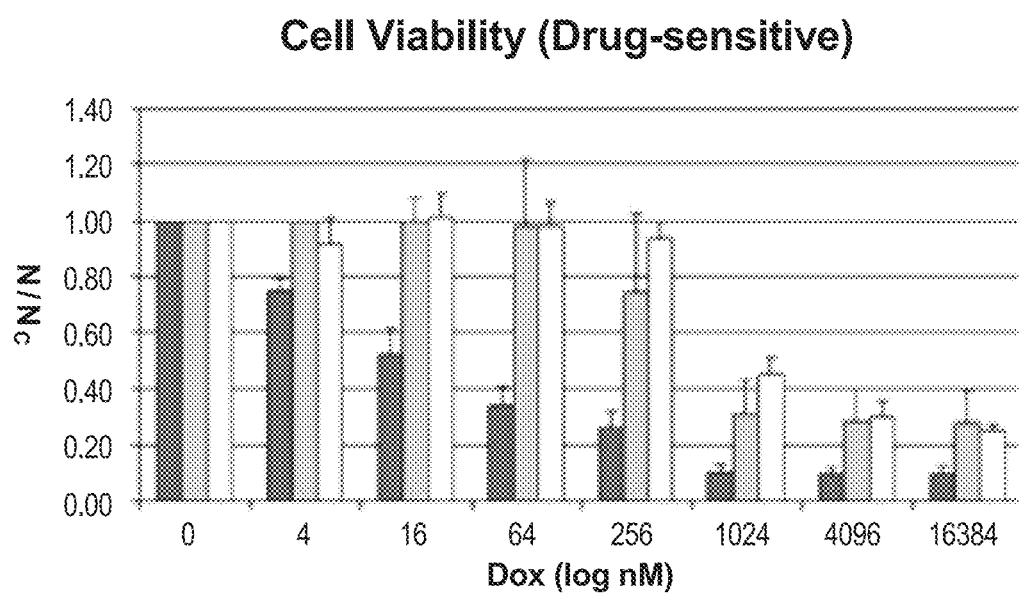
FIG. 34 illustrates therapy response predictions.

Tumor response to doxorubicin was calibrated using 2D in vitro monolayers of MCF-7 breast cancer cell lines. The calibrated model was used to predict therapy response in 3D tumor spheroids. Excellent agreement was obtained with in vitro experiments, highlighting the nonlinear interactions between cell phenotype and substrate and drug gradients in determining the success of therapy (FIG. 34). FIG. 34 shows therapy response predictions. After calibrating to 2D monolayers (dark gray) of MCF7 breast cancer cells, 3D response was simulated (light gray) and compare to tumor spheroid experiments (white).

Figure 35:
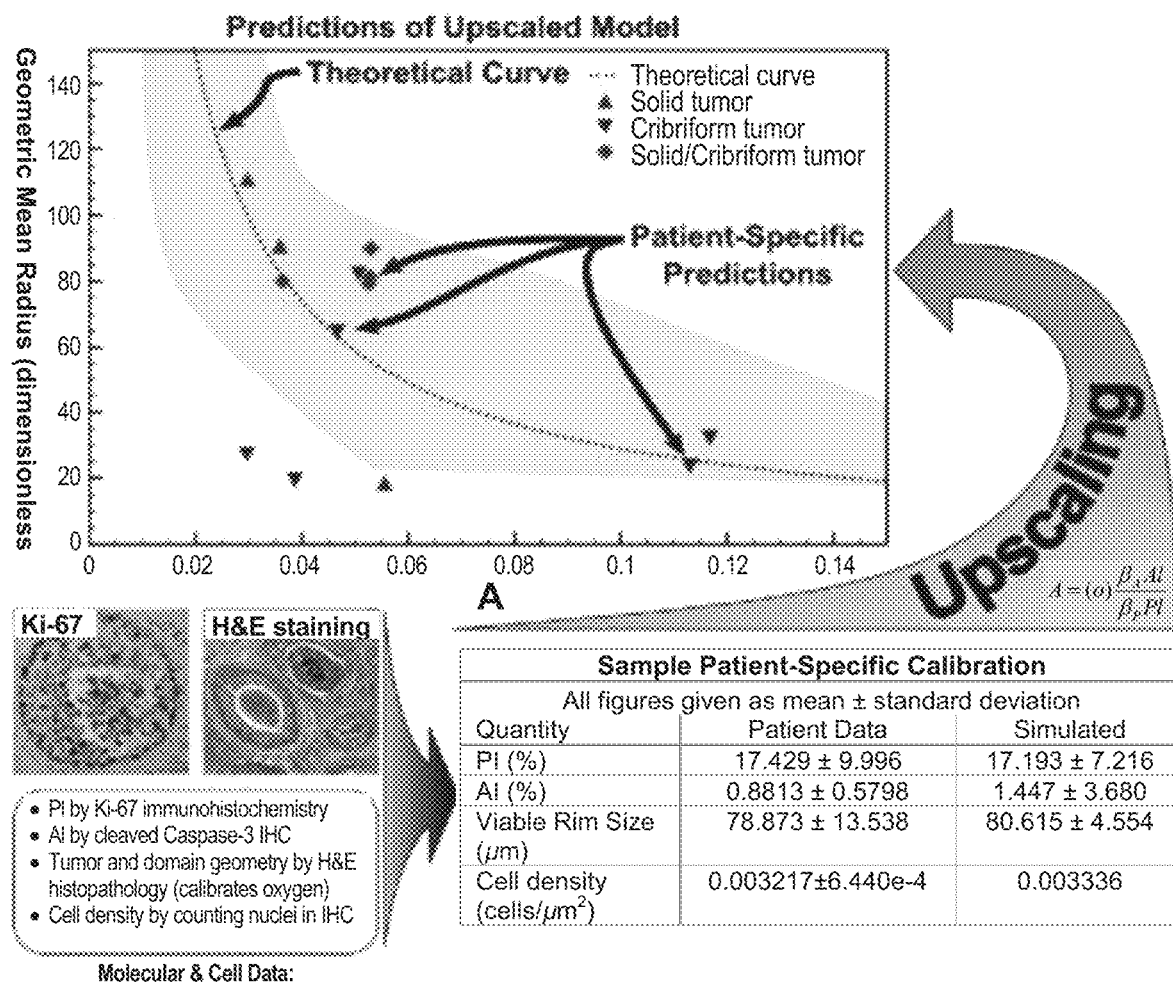
FIG. 35 illustrates Multiscale Model Calibration.

A multiscale framework was used to calibrate agent-based model to ductal carcinoma in situ of the breast. Calibration was performed with data from ex vivo immunohistochemistry (IHC) for proliferation (Ki-67) and apoptosis (cleaved Caspase-3), histopathologic measurements of tumor viable rim thickness, and cell density. The continuum model was up-scaled to be calibrated by volume averaging. As shown in FIG. 35, the framework predicted the tumor size versus the balance between tumor apoptosis and mitosis (represented by a nondimensional parameter A). Excellent agreement for most of our index cases was found with respect to post-mastectomy measurements of the tumor size. In FIG. 35, bottom left panel shows multiscale model calibration by up-scaling patient-specific IHC and histopathology data, applied to breast cancer. The table verifies the cell-scale calibration, and the curve (top) compares tissue-scale predictions to patient outcomes with excellent agreement. These modeling data illustrate our ability to develop and calibrate models that not only recapitulate the in vivo tumor microenvironment, but yield quantitative, testable predictions of tumor microenvironment dynamics.

Example 21

Information Flow Across Scales and Calibration

Figure 36:
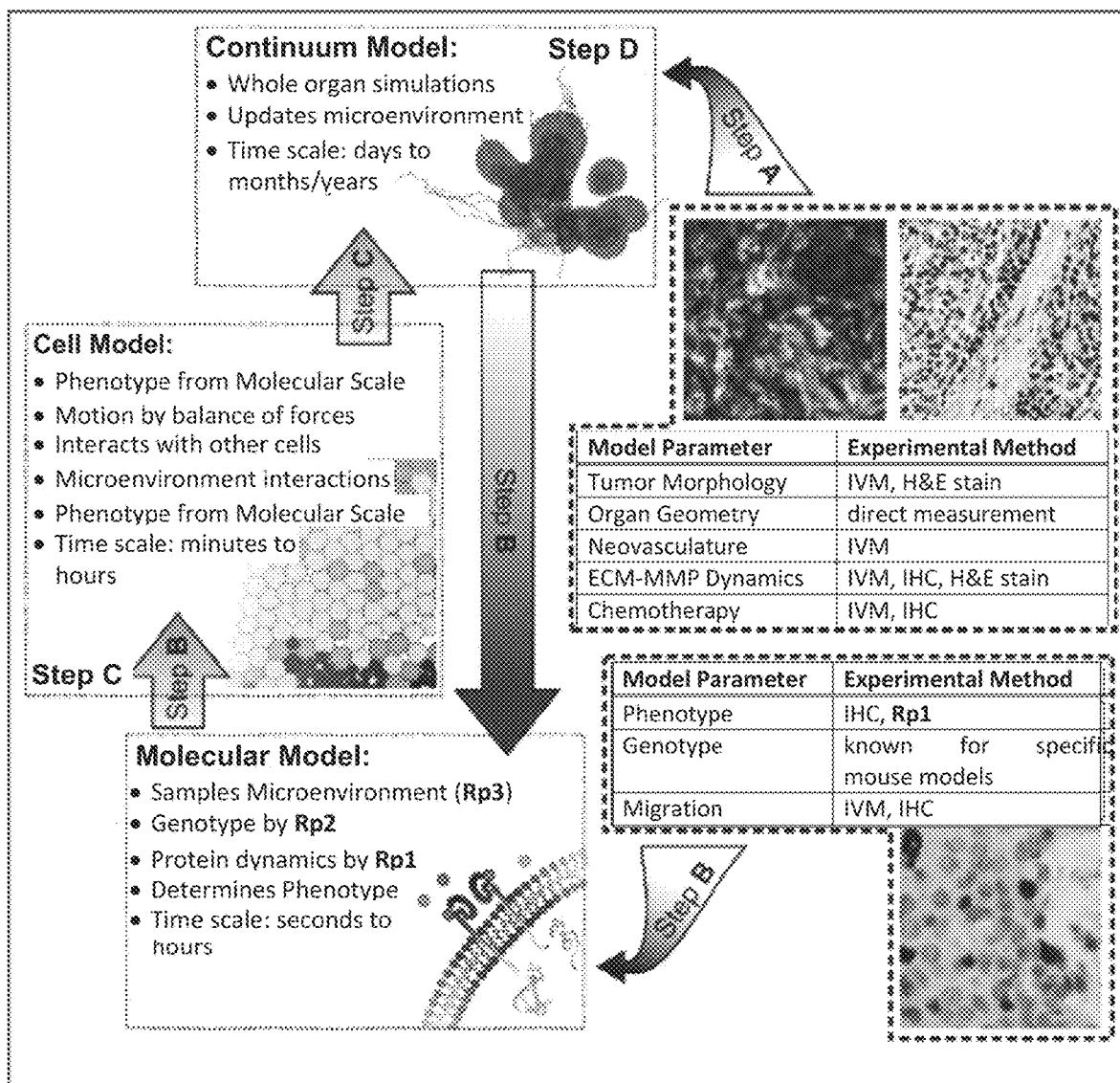
FIG. 36 illustrates Multiscale workflow incorporating data flow across scales.

As in FIG. 36, better model constraint is obtained by continuously occurring processes and dynamically improving the integration of measurements across many scales. These processes include: 1) a rigorous subcellular signaling model, such as RP1 as described herein, that mechanistically determines cell phenotype; 2) tissue-scale parameters obtained dynamically through the cell-scale model; 3) mechanistically tying macroscopic behavior to a rigorous signaling model; and 4) information flowing bi-directionally using up- and downscaling with data incorporated at the appropriate scales. To build a model, the following steps (A)-(D) are taken.

Step A. Tissue-scale initialization is performed as follows. The tumor and neovasculature is initialized by IVM data with lymph node/spleen size estimated by direct measurements taken of removed organs at various time points. Standardized organ histology, such as cortex, medulla, follicles, fluid, capsule, and trabeculae are mapped onto the measured organ dimensions and randomly place the tumor into this structure. IVM host cell and ECM measurements partially constrain tumor placement. The effects of tumor placement error are investigated via simulation. Mechanical and vascular properties are mapped onto the virtual organ based upon the ECM and vascular (density, radius, morphology, and tortuosity) IVM measurements. Dead cell density is seeded to match IHC measurements of the necrotic core as a percentage of total tumor volume. Model is solved for the initial substrate distributions for this geometry, and use the $n=n_N$ nutrient contour to further constrain the necrotic tumor morphology. Standardized mouse histology atlases may be used.

Step B. Agent model is calibrated as follows. The signaling pathways are imported from RP1. Tissue-scale ECM densities and substrate distributions are interpolated from (A) to seed the cell-scale microenvironment. Data are combined to uniquely initialize the cell-scale model.

Step C. Tissue-scale cell properties: After running the cell-scale model for a short burst of time under 1 day of simulated time, the cell positions are upscaled to update the tissue-scale cell densities. The cell-scale proliferation and apoptosis rates and motility parameters are upscaled to calibrate the continuum scale.

Step D. Whole-organ tissue evolution: Tissue-scale code is ran for several simulated days to update the neovasculature, transport, cell densities, tissue biomechanics, and lymph node/spleen expansion. By (B)-(C), the biological parameters (cell birth and death, motility) are spatially heterogeneous with automatic incorporation of the cell response to the microenvironment.

After completing steps (A)-(D), all molecular, cell, and tissue-scale data are fully integrated to calibrate and constrain the multiscale framework. Steps (B)-(D) are looped to simulate the entire lesion and the surrounding microenvironment while efficiently incorporating the finer spatiotemporal dynamics into the evolution.

Equation-free approach (EFA) is applied in select patches where molecular-to-cell-scale dynamics are expected to be important to drive the link between the discrete and continuum models. The EFA accelerates the discrete cell-scale code in the selected patches using coarse time projection/integration methods. The result is a hybrid, multiscale tumor simulator which benefits from the efficiency of the continuum model while dynamically applying the discrete model where cell-scale effects are most important.

Example 22

Intravital Tumor and Vasculature Measurement Methods

IVM techniques are employed to visualize, analyze, and quantify tumor growth parameters to provide input data, both prior and subsequent to incorporating RP1 signaling model. Other small animal imaging modalities such as macroscopic bioluminescence and fluorescence systems, MRI, PET-CT, SPECT, Ultrasound, Raman, or photoacoustic are utilized to demonstrate precise localization and geometry of tumor within the lymph node structure.

Vascular properties such as density, size, and morphology, cellular migration, cellular proliferation, MMP and adhesion molecule expression, and vessel permeability are quantified using a two-photon microscope for deep tissue imaging with up to ~500 μm penetration and second harmonic imaging. For consistency across projects from molecular events through cellular, tissue, and organismal levels in modeling and experiment, the appropriate sites in the orthotopic lymphoma and AML models are repeatedly and dynamically imaged. Measurements are preceded by tail-vein injection of a long circulating dye such as dextran-rhodamine or Angiosense™ to visualize the vasculature. Vascular properties such as density, morphology, or radius are measured with dyes. High statistical levels over many time points across many mice are achieved by compiling a large set of vascular properties data. Long-circulating dyes are used as reference tools for visualizing blood vessels as an intrinsic fiducial marker by which to return to the same field of view (FOV) day after day. Photo switchable proteins can be used for collecting the data.

Example 23

Visualization of Lymphoma and Leukemia

Blood vessel properties for lymphoma and leukemia are visualized and measured using the optical sectioning capability of the IVM instrument to provide three-dimensional spatial information. First, intravital microscopy sites are chosen as follows. For each experiment, 2 groups of n=4 mice are used (one experimental lymphoma, and one normal control). Fluorescent-labeled mice are used for visualization. For lymphoma, IVM-visualization is performed on the inguinal lymph node. For AML, the spleen is used for visualization. A mouse strain labeled with a fluorescent marker in a bicistronic construct (MSCV-oncogene-IRES-marker) is used. Imaging is repetitively performed and statistically treatment is performed on the image data to ensure measurement consistency over various vascular properties such as density, morphology, and size of the sites.

Vascular property measurements are combined with blood flow measurements. For lymphoma model, drug-sensitive Eμ-myc mice are used. A normal, no tumor mice strain is used as control. Fluorescently outlined vasculature within the context of the lymph node region of interest are imaged and a minimum of 10 field of views (FOVs) per animal at 10×-20× magnification are three-dimensionally acquired. From these images, the following are quantified: blood vessel density (percentage of FOV occupied by blood vessel, number of vessel segments per FOV), vessel branching (number of branch points per vessel segment per FOV), size (mean vessel radius per FOV), and morphology (raw image showing vessel distribution). Within the same animals at identical time points, fluorescent polystyrene microparticles of specific weight similar to blood are injected through tail-vein. Time series in small FOVs are acquired to increase video frame rate, yielding more accurate quantification of blood flow rate. Blood flow rate is measured using particle image velocimetry. The average spatial displacement of a particle within the blood vessel flow between two or more are applied to yield particle velocity.

The rate and geometry of doxorubicin extravasation from the blood vessels is quantified to provide these data as input for the mathematical model of vascular permeability. Agent size is varied as necessary to simulate differently sized drugs. To do so, PEG chains of discrete chain length (e.g., 2,000, 5,000, and 10,000 molecular weight) are used to model different-sized drugs while fluorescence is held constant. The spatiotemporal drug distribution is followed from entry into the tumor bed until it is no longer visible (hours to days). Concurrently, dynamic imaging and quantitation is performed to record the effect of the drug on spatial tumor cell distribution.

The migration of tumor cells within the tumor microenvironment is visualized on our system using minimal laser power. Time series in ~3-4 fields of view are acquired over approximately 1 hour. Tumor cell migration are quantified as an average velocity using an algorithm similar to that used for particle velocimetry in which the average spatial displacements of each cell are determined with maximum statistical cross-correlation integrated over many frames. The number of tumor cells migrating out of the total number of tumor cells within the field of view as well as their velocities, and their motile persistence (temporal) are collected and used as inputs to a model.

To measure proliferation rate, IVM is employed to visualize tumor cells in a single field of view to image them consecutively over a period of ~4 hours. Minimal laser power is used to minimize the impact of the energy delivered. Ma magnification of 4× is used to maintain many cells visible in a single FOV. To ensure statistical significance, many cells are simultaneous visualized while performing digital zoom to enable improved cellular discrimination. The number of actively dividing cells is quantified by using of a cell counting software.

Glucose distribution is monitored as a marker for tumor cell proliferation. Microscale IVM and a fluorescent glucose analogue are used for the measurement. The fluorescent glucose analogue is injected via tail vein, 24 hours prior to imaging, and the spatial probe distribution is mapped. The gradients of the analogue are quantified as a function of the distance from the blood vessels and from the tumor surface.

Two-photon microscopy is used to measure ECM density. Second harmonic generation (SHG) is applied to visualize periodic, highly polarizable biological structures such as collagen. Using SHG, a measure of ECM density is derived by correlation with the collagen density within the tumor bed. A map of the ECM density distribution within the tumor is then generated. The map is dynamically followed over a period of weeks and is used to help calibrate the model. Cell density is concurrently measured with vascular measurements, to account for its potential impact on molecular diffusion.

MMP Expression is imaged using MMPSense™, which facilitates simultaneous measurements of the activity of MMP 2, 3, 9, and 13 by the unquenching of dyes attached to cleaved peptides. The distribution of MMP activity captured both qualitatively and quantitatively (e.g., gradient of intensity as a function of distance from blood vessels and in terms of the depth in the tumor) are combined with ECM density measurements to model a state of the MMP-ECM.

Integrin expression is followed as a proxy measure of the maturity of vessel age. IntegriSense™ is used to quantify the abundance of integrin $\alpha_V\beta_3$ expressed on many blood vessels via fluorescent intensity and distribution. The distribution data are used to yield a measure of vessel age for the mathematical model.

Animals at various time points (e.g., 24 and 72 hours, 7, 10, and 14 days after tumor has been detected via intravital interrogation) are taken for IVM experiments. For IHC, tumor is removed, fixed, and prepared. Hematoxylin and Eosin (H&E) staining is performed as well as for staining for a number of antigens for cell migration (uPA), Ki-67, proliferation adhesion antigens (e.g., integrins, ICAM-1, LFA-1), apoptosis (TUNEL assay and cleaved Caspase-3), hypoxia (HIF-1α), and vessel presence (density, CD31). The spatial distributions, densities, and variability of these features are extracted using standard image analysis software and statistical techniques. Extracted data are input to the model for training and calibration. A Proliferation Index (PI) is defined as the fraction of Ki-67-positive cell nuclei in a FOV, and is integrated with a similarly-defined apoptotic index (AI) into the model.

Methods described for collecting data on mouse tumor are used to collect data on human histological specimens of lymphoma and AML. Comparisons between murine and human histological specimens are made to account for the difference between the two systems and used as input to mathematical models for human disease.

Example 24

Integrative In Vivo/In Silico Investigations of Cancer Biophysics

The spatiotemporal evolution of lymphoma and AML is modeled by linking variations in phenotype, ECM/RN-MMP dynamics, and vascularization across the tumors and in time. To capture many facets of longitudinal tumor evolution by imaging at many time points, doxorubicin-sensitive Eµ-myc lymphoma model and the AML1/E09a+NRAS AML model, which are slowly-growing tumor animal models, are used for collecting in vivo data. Detailed time-course measurements of the tumor morphology, vascular morphology and age, tumor cell migration, proliferation, and apoptosis, ECM-MMP dynamics, and glucose transport are obtained using the IVM and IHC techniques.

A tumor model for lymphoma and AML are initialized using the in vivo data. First, unmodified tumor system is created with spatial maps of variations in the cell phenotype, microvasculature, nutrient distribution, and microenvironment (ECM/RN density and MMP distribution), and VEGF distribution. The system is then perturbed by altering (i) proliferation response to nutrient, (ii) VEGF secretion in response to hypoxia, (iii) MMP secretion, (iv) cell-cell adhesion, (v) cell-ECM adhesion, and (vi) cell motility. The impact on the spatial distribution of phenotype and tumor evolution is then observed. To validate, the simulation (calibrated based upon early time data time points) is compared to later time points in the same mice, checking for matching tumor morphology, growth rate, and vascular properties. As extra model constraint and validation, IHC data are compared at these later time points. The model is modified to account for differences detected in the validation process to achieve a sufficient match.

To generate predictions, virtual perturbations are introduced to the tumor-microenvironment system and changes in the tumor and microvascular evolution are observed. Perturbations such as decreasing cell-cell adhesion in lymphoma or interfering with VEGF signaling are introduced. Genetic changes or silencing with RNAi are introduced. Once the virtual model is fully trained on the Eµ-Myc lymphoma model, the model is modified to account for other genetic changes such as p53-null genotype using the ER-myc/p53−/− model. In silico prediction is followed up by in vivo mouse models using either a different tumor strain or RNAi to interfere with the appropriate tumor pathways that correspond to the phenotypic perturbations performed in silico.

To model for other factors affecting tumor behavior, the model is perturbed for hypoxia, such as silencing HIF-1α, and other angiogenic and hypoxic pathways in AML.

To model for spatiotemporal evolution of lymphoma and AML in response to chemotherapy, both Eµ-Myc/Arf−/− (chemosensitive) and Eµ-Myc/p53−/− (chemoresistant) lymphoma tumor models are imaged and quantified using doxorubicin (intrinsically fluorescent) at a statistical level of n=4 per group. For AML, the AML1/ETO9a+Nras (chemosensitive) and MLL/AF9+Nras (chemoresistant) mouse models are used with doxorubicin.

A chemotherapy response model is initialized based upon the transport measured in vivo and the cell kill responses. The virtual system is perturbed by altering (i) cell-scale drug response by simulating the chemoresistant mouse models, and (ii) vessel permeability. The system is observed for the impact on the spatial distribution of phenotype (including apoptotic response) and tumor evolution. To validate, the simulation (calibrated based upon early time data time points) is compared to later time points in the same mice, checking for matching the tumor morphology, growth rate, drug distribution, cell kill, and vascular properties.

To model for combined-therapy, the model is perturbed by combining RNAi and chemotherapy or multiple drugs. The impact of perturbations on tumor evolution and therapy response, such as synergistic effects of drug combination treatment, is then recorded. Predictions are generated on how to combine various therapies to affect tumor biology in a dynamic, synergistic manner.

While preferred embodiments of the present invention have been described herein, such embodiments are provided by way of example only. Numerous variations, changes, and substitutions are available without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of predicting cancer emergence in a first subject in need thereof, said method comprising:
   (a) obtaining a sample from the first subject;
   (b) obtaining
      (i) a molecular-scale measurement from the sample,
      (ii) a cellular scale measurement from the sample,
      (iii) an organ-scale measurement from the first subject, and
      (iv) an organism-scale measurement from the first subject;
   (c) providing the measurements obtained from step (b) to a computer comprising a computer executable code for running a state-evolution simulation model of cancer emergence, wherein the measurements are used by the computer executable code as an initial parameter of the state-evolution simulation model, wherein the state-evolution simulation model comprises:
      (i) a molecular-scale simulation model of the cancer,
      (ii) a cellular-scale simulation model of the cancer,
      (iii) a tissue-scale simulation model of the cancer,
      iv) an organism-scale simulation model of the cancer, and
      (v) instructions for refining the molecular-scale simulation model, the cellular-scale simulation model, the tissue-scale simulation model, and the organism-scale simulation model based upon output from the molecular-scale simulation model, cellular-scale simulation model, the tissue-scale simulation model, and the organism-scale simulation model;
   (d) using the computer, running the state-evolution simulation model to produce an output comprising a prediction of cancer state at the molecular-scale, cellular-scale, tissue-scale and organism-scale level;
   (e) comparing the output of the model to outputs obtained for results of at least one of each of (i) molecular-scale measurement, (ii) cellular-scale measurement, (iii) organ-scale measurement, and (iv) organism-scale measurement from a second subject of known cancer status;
   (f) based upon the state-evolution simulation model output of (d) and the comparison of (e), generating a prediction of emergence of the cancer in the first subject;
   (g) selecting a treatment to ameliorate symptoms associated with the prediction of emergence of the cancer in the first subject; and
   (h) administering the treatment to the first subject.

2. The method of claim 1, wherein said cancer emergence is selected from acute myelogenous leukemia (AML) emergence, non-Hodgkins lymphoma (NHL) emergence, and primary follicular lymphoma emergence.

3. The method of claim 1, wherein said method includes at least one thousand data points or measurements from said first subject.

4. The method of claim 1, wherein said cellular-scale or molecular-scale measurements are taken from a tumor, and said cancer emergence is modeled with at least one parameter for cell adhesion, tissue invasion, or microenvironmental substrate gradients.

5. The method of claim 4, wherein said cellular-scale measurements are selected from at least one of epigenetic somatic cell clock data, cell history patterns, or microenvironmental conditions.

6. The method of claim 5, wherein said microenvironmental conditions are selected from oxygen levels, nutrient levels, and growth factor levels.

7. The method of claim 1, wherein said organ-scale measurements are selected from at least one of vasculature structure, three-dimensional physical parameters of an organ, blood flow rate, ECM degradation rate, ECM secretion rate, tissue density, drug extravasation rate, spatial distribution of cells within a tumor, statistical distribution of cells within a tumor, tumor size, or response of a cancer to treatment.

8. The method of claim 7, wherein said cancer for which response to treatment is measured is selected from acute myelogenous leukemia (AML), non-Hodgkins lymphoma (NHL), and primary follicular lymphoma.

9. The method of claim 7, wherein said organ measured for three-dimensional physical parameters is a lymph node.

10. The method of claim 1, wherein said organism-scale measurements are selected from at least one of dietary history, individual medical history, family medical history, geographic history, body-mass index, environmental exposure history, educational history, economic history, or behavioral history.

* * * * *

SEQUENCE LISTING

<160> NUMBER OF SEQ ID NOS: 2

<210> SEQ ID NO 1
<211> LENGTH: 107
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 1
ggagatttag gaacttttt tgttttacgc gcgtttgttt ttgcgtacgg gagagtttgt      60
ggcggcgatt atgtagcgtg taatgagtga ttttgtagtt tggtgtt                 107

<210> SEQ ID NO 2
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
tttaggagtg agtagttgtt ttcggttcgt cggatatatc ggatagatag acgtgcggac     60
ggtttattat tttagttcgt taattagtta gtttgcgttt ggcgtttttt tttttaggt    120 agggttggt                                                          129
```